(12) United States Patent
Waetzig et al.

(10) Patent No.: US 11,999,744 B2
(45) Date of Patent: Jun. 4, 2024

(54) CRYSTALLINE FORMS OF (S)-1-(4-FLUOROPHENYL)-1-(2-(4-(6-(1-METHYL-1H-PYRAZOL-4-YL)PYRROLO[2,1-F][1,2,4]TRIAZIN-4-YL)PIPERAZINYL)-PYRIMIDIN-5-YL)ETHAN-1-AMINE AND METHODS OF MAKING

(71) Applicant: Blueprint Medicines Corporation, Cambridge, MA (US)

(72) Inventors: Joshua D. Waetzig, Cambridge, MA (US); Gordon Wilkie, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 18/543,793

(22) Filed: Dec. 18, 2023

(65) Prior Publication Data
US 2024/0132510 A1 Apr. 25, 2024

Related U.S. Application Data

(60) Division of application No. 17/153,727, filed on Jan. 20, 2021, which is a continuation of application No. PCT/US2020/027724, filed on Apr. 10, 2020.

(60) Provisional application No. 62/990,269, filed on Mar. 16, 2020, provisional application No. 62/844,575, filed on May 7, 2019, provisional application No. 62/833,527, filed on Apr. 12, 2019.

(51) Int. Cl.
*C07D 487/04* (2006.01)
*A61P 17/00* (2006.01)
*A61P 35/00* (2006.01)

(52) U.S. Cl.
CPC ............ *C07D 487/04* (2013.01); *A61P 17/00* (2018.01); *A61P 35/00* (2018.01); *C07B 2200/13* (2013.01)

(58) Field of Classification Search
CPC .................................................. C07D 487/04
See application file for complete search history.

(56) References Cited

U.S. PATENT DOCUMENTS

| | | |
|---|---|---|
| 6,982,265 B1 | 1/2006 | Hunt et al. |
| 7,244,733 B2 | 7/2007 | Hunt et al. |
| 8,609,672 B2 | 12/2013 | Russu et al. |
| 8,802,697 B2 | 8/2014 | Bifulco, Jr. et al. |
| 9,126,951 B2 | 9/2015 | Bifulco, Jr. et al. |
| 9,200,002 B2 | 12/2015 | Hodous et al. |
| 9,334,263 B2 | 5/2016 | Hodous et al. |
| 9,340,514 B2 | 5/2016 | Bifulco, Jr. et al. |
| 9,434,700 B2 | 9/2016 | Bifulco, Jr. et al. |
| 9,499,522 B2 | 11/2016 | DiPietro et al. |
| 9,688,680 B2 | 6/2017 | Hodous |
| 9,695,165 B2 | 7/2017 | Bifulco, Jr. et al. |
| 9,884,861 B2 | 2/2018 | Hodous et al. |
| 9,944,651 B2 | 4/2018 | Hodous et al. |
| 9,994,552 B2 | 6/2018 | DiPietro et al. |
| 9,994,575 B2 | 6/2018 | Hodous et al. |
| 10,000,490 B2 | 6/2018 | Bifulco, Jr. et al. |
| 10,000,496 B2 | 6/2018 | Hodous et al. |
| 10,017,512 B2 | 7/2018 | Wenglowsky et al. |
| 10,030,005 B2 | 7/2018 | Brubaker et al. |
| 10,035,789 B2 | 7/2018 | Brubaker et al. |
| 10,202,365 B2 | 2/2019 | Brooijmans et al. |

(Continued)

FOREIGN PATENT DOCUMENTS

| | | |
|---|---|---|
| CN | 102040494 A | 5/2011 |
| CN | 105658652 A | 6/2016 |

(Continued)

OTHER PUBLICATIONS

Akin et al., Pioneer: A Randomized, Double-Blind, Placebo-Controlled, Phase 2 Study of Avapritinib in Patients with Indolent or Smoldering Systemic Mastocytosis with Symptoms Inadequately Controlled with Standard Therapy. American Academy of Allergy Asthma and Immunology Annual Meeting. 19 pages, Mar. 16, 2020.

(Continued)

*Primary Examiner* — Golam M Shameem
(74) *Attorney, Agent, or Firm* — McCarter & English, LLP; Wei Song

(57) ABSTRACT

Crystalline Forms of Compound (I):

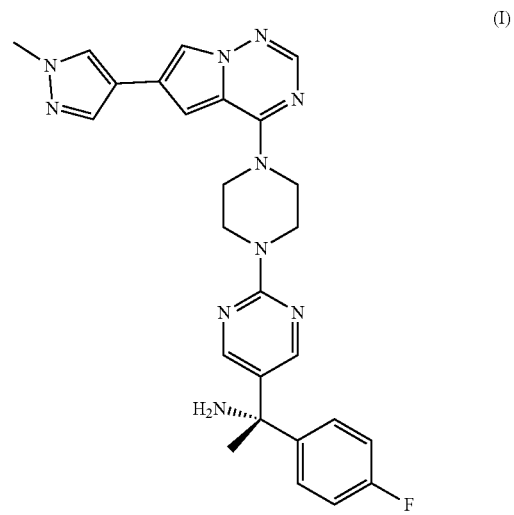

pharmaceutically acceptable salts thereof and solvates of any of the foregoing are disclosed. Pharmaceutical compositions comprising the same, methods of treating disorders and conditions associated with oncogenic KIT and PDGFRA alterations using the same, and methods for making Compound (I) and crystalline forms thereof are also disclosed.

14 Claims, 14 Drawing Sheets

(56) References Cited

U.S. PATENT DOCUMENTS

| | | |
|---|---|---|
| 10,227,329 B2 | 3/2019 | Brubaker et al. |
| 10,584,114 B2 | 3/2020 | Brubaker et al. |
| 10,807,985 B2 | 10/2020 | Hodous et al. |
| 11,046,697 B2 | 6/2021 | Wenglowsky et al. |
| 11,827,642 B2 | 11/2023 | Hodous et al. |
| 2004/0186140 A1 | 9/2004 | Cherney et al. |
| 2006/0211695 A1 | 9/2006 | Borzilleri et al. |
| 2014/0187559 A1 | 7/2014 | Miduturu |
| 2016/0031892 A1 | 2/2016 | Hodous |
| 2016/0102097 A1 | 4/2016 | Hodous et al. |
| 2017/0022206 A1 | 1/2017 | Hodous et al. |
| 2017/0029409 A1 | 2/2017 | DiPietro et al. |
| 2017/0066773 A1 | 3/2017 | Wenglowsky et al. |
| 2017/0066812 A1 | 3/2017 | Bifulco, Jr. et al. |
| 2017/0119760 A1 | 5/2017 | Moussy et al. |
| 2017/0121312 A1 | 5/2017 | Brubaker et al. |
| 2017/0145018 A1 | 5/2017 | Wenglowsky et al. |
| 2017/0174652 A1 | 6/2017 | Bifulco, Jr. et al. |
| 2017/0204104 A1 | 7/2017 | Hodous et al. |
| 2017/0253593 A1 | 9/2017 | Bifulco, Jr. et al. |
| 2017/0267661 A1 | 9/2017 | Kim et al. |
| 2017/0298069 A1 | 10/2017 | Brooijmans et al. |
| 2018/0022731 A1 | 1/2018 | Brooijmans et al. |
| 2018/0022732 A1 | 1/2018 | Brubaker et al. |
| 2018/0362613 A1 | 12/2018 | Bifulco, Jr. et al. |
| 2019/0119280 A1 | 4/2019 | Hodous et al. |
| 2020/0024280 A1 | 1/2020 | Hodous et al. |
| 2021/0147433 A1 | 5/2021 | Waetzig et al. |
| 2023/0124801 A1 | 4/2023 | Mar |
| 2023/0271971 A1 | 8/2023 | Waetzig et al. |

FOREIGN PATENT DOCUMENTS

| | | |
|---|---|---|
| CN | 108191874 A | 6/2018 |
| CN | 110938077 A | 3/2020 |
| CN | 110950872 A | 4/2020 |
| EP | 0200968 A1 | 11/1986 |
| JP | 2005-503372 A | 2/2005 |
| JP | 2006-519205 A | 8/2006 |
| JP | 2007-535558 A | 12/2007 |
| JP | 2008-504366 A | 2/2008 |
| JP | 2009-514882 A | 4/2009 |
| JP | 2009-542814 A | 12/2009 |
| JP | 6446040 B2 | 12/2018 |
| RU | 2331640 C2 | 8/2008 |
| WO | WO-2000/071129 A1 | 11/2000 |
| WO | WO-2001/025220 A1 | 4/2001 |
| WO | WO-2003/010158 A1 | 2/2003 |
| WO | WO-2003/090912 A1 | 11/2003 |
| WO | WO-2004/071460 A2 | 8/2004 |
| WO | WO-2004/076450 A1 | 9/2004 |
| WO | WO-2005/117909 A2 | 12/2005 |
| WO | WO-2006/004636 A2 | 1/2006 |
| WO | WO-2006/028524 A2 | 3/2006 |
| WO | WO-2007/056170 A2 | 5/2007 |
| WO | WO-2007/065100 A1 | 6/2007 |
| WO | WO-2007/085188 A1 | 8/2007 |
| WO | WO-2008/005956 A2 | 1/2008 |
| WO | WO-2009/015254 A1 | 1/2009 |
| WO | WO-2009/117157 A1 | 9/2009 |
| WO | WO-2010/002095 A2 | 1/2010 |
| WO | WO-2010/022055 A2 | 2/2010 |
| WO | WO-2010/144345 A1 | 12/2010 |
| WO | WO-2011/005119 A1 | 1/2011 |
| WO | WO-2011/103196 A1 | 8/2011 |
| WO | WO-2012/027495 A1 | 3/2012 |
| WO | WO-2014/039714 A2 | 3/2014 |
| WO | WO-2014/100620 A2 | 6/2014 |
| WO | WO-2014/160521 A1 | 10/2014 |
| WO | WO-2015/057873 A1 | 4/2015 |
| WO | WO-2015/058129 A1 | 4/2015 |
| WO | WO-2016/022569 A1 | 2/2016 |
| WO | WO-2017/019442 A1 | 2/2017 |
| WO | WO-2018/049233 A1 | 3/2018 |
| WO | WO-2018/183712 A1 | 10/2018 |
| WO | WO-2019/034128 A1 | 2/2019 |
| WO | 2019/152719 A1 | 8/2019 |
| WO | WO-2020/102095 A1 | 5/2020 |
| WO | WO-2020/210669 A1 | 10/2020 |
| WO | WO-2021/004895 A1 | 1/2021 |
| WO | WO-2021/079134 A1 | 4/2021 |

OTHER PUBLICATIONS

Akin, Pioneer: A Randomized, Double-Blind, Placebo-Controlled, Phase 2 Study of Avapritinib in Patients with Indolent or Smoldering Systemic Mastocytosis with Symptoms Inadequately Controlled with Standard Therapy. 61st American Society of Hematology (ASH) Annual Meeting and Exposition. Poster 2950, 1 page, Dec. 7-10, 2019.

Antonescu, What lessons can be learned from the GIST paradigm that can be applied to other kinase-driven cancers. J Pathol. Jan. 2011;223(2):251-261.

Bennett et al., Cecil Textbook of Medicine, 20th Edition, vol. 1, W.B. Saunders Company, Philadelphia. pp. 1004-1010, (1996).

Blueprint Medicines, 2020 Blueprint global business strategy. 32 pages, Jan. 7, 2019.

Blueprint Medicines, Blueprint Medicines Announces Part 1 Results from PIONEER Trial Showing Broad Activity of Avapritinib Across Measures of Mast Cell Burden, Clinical Outcomes and Quality of Life in Indolent Systemic Mastocytosis. Press Release, Blueprint Medicines Corporation, 10 pages, Mar. 16, 2020.

Blueprint Medicines, Precision That Moves™ Staying one step ahead of disease. J.P. Morgan Healthcare Conference, 35 pages, Jan. 13-16, 2020.

Broesby-Olsen et al., Kit D816V mutation burden does not correlate to clinical manifestations of indolent systemic mastocytosis. J Allergy Clin Immunol. Sep. 2013;132(3):723-728.

Caira, Crystalline Polymorphism of Organic Compounds. Topics in Current Chemistry. Design of Organic Solids. Springer. E. Weber (Ed.). Volume 198, pp. 163-208, Jan. 1998.

Cairoli et al., Prognostic impact of c-KIT mutations in core binding factor leukemias: an Italian retrospective study. Blood. May 1, 2006;107(9):3463-8.

Cohen, The development and therapeutic potential of protein kinase inhibitors. Curr Opin Chem Biol. Aug. 1999;3(4):459-65.

Dermer, Another Anniversary for the War on Cancer. Bio/Technology. Mar. 1994;12:320.

Drummond et al., Preliminary Safety and Activity in a Phase 1 study of BLU-285, a Potent, Highly-Selective Inhibitor of Kit D816V in Advanced Systemic Mastocytosis (SM). American Society of Hematology Annual Meeting. 19 pages, Dec. 4, 2016.

Evans et al., A precision therapy against cancers driven by KIT/PDGFRA mutations. Sci Transl Med. Nov. 1, 2017;9(414):eaao1690, 12 pages.

Freshney, Culture of Animal Cells, a Manual of Basic Technique. Alan R. Liss, Inc. pp. 1-6, (1983).

Gotlib et al., Avapritinib, a Potent and Selective Inhibitor of Kit D816V, Improves Symptoms of Advanced Systemic Mastocytosis (AdvSM). American Society of Hematology Annual Meeting. 18 pages, Dec. 2, 2018.

Heinrich et al., Preliminary safety and activity in a first-in-human Phase 1 study of BLU-285, a potent, highly selective inhibitor of KIT and PDGFRalpha activation loop mutants in advanced gastrointestinal stromal tumor (GIST). EORTC-NCI-AACR Molecular Targets and Cancer Therapeutics Symposium. 17 pages, Dec. 1, 2016.

Hilfiker et al., Relevance of Solid-state Properties for Pharmaceutical Products. Polymorphism: in the Pharmaceutical Industry. Wiley-VCH Verlag Gmbh & Co. Chapter 1, pp. 1-19. Feb. 6, 2006.

InvivoChem—Material Safety Data Sheet (MSDS). Retrieved online at: https://www.invivochem.com/avapritinib.html. 6 pages, Apr. 21, 2017.

Lee et al., Correlation of imatinib resistance with the mutational status of KIT and PDGFRA genes in gastrointestinal stromal tumors: a meta-analysis. J Gastrointestin Liver Dis. Dec. 2013;22(4):413-8.

(56) References Cited

OTHER PUBLICATIONS

Paschka et al., Adverse prognostic significance of KIT mutations in adult acute myeloid leukemia with inv(16) and t(8;21): a Cancer and Leukemia Group B Study. J Clin Oncol. Aug. 20, 2006;24(24):3904-11.
Quintela et al., A Ready One-pot Preparation for Pyrrolo[2,1-f]-[1,2,4]triazine and Pyrazolo[5,1-c]pyrimido[4,5-e]-[1,2,4]triazine Derivatives. Tetrahedron. 1996;52(8):3037-3048.
Schnittger et al., KIT-D816 mutations in AML1-ETO-positive AML are associated with impaired event-free and overall survival. Blood. 2006;107:1791-1799.
Selleckchem, Safety Data Sheet. Retrieved online at: https://www.selleckchem.com/products/blu-285.html. 6 pages, Jan. 16, 2019.
Shallal et al., Discovery, synthesis, and investigation of the antitumor activity of novel piperazinylpyrimidine derivatives. Eur J Med Chem. Jun. 2011;46(6):2043-57.
Wu et al., Avapritinib: A Selective Inhibitor of KIT and PDGFR? that Reverses ABCB1 and ABCG2-Mediated Multidrug Resistance in Cancer Cell Lines. Mol Pharm. Jul. 1, 2019;16(7):3040-3052.
Zhang et al., Design and pharmacology of a highly specific dual FMS and KIT kinase inhibitor. Proc Natl Acad Sci U S A. Apr. 2, 2013;110(14):5689-94.
Indian Office Action for Application No. 201617009956, dated Nov. 26, 2019, 7 pages.
International Search Report and Written Opinion for Application No. PCT/US2014/027008, dated Jul. 24, 2014, 11 pages.
International Search Report and Written Opinion for Application No. PCT/US2014/060746, dated Dec. 17, 2014, 8 pages.
International Search Report and Written Opinion for Application No. PCT/US2014/061211, dated Dec. 10, 2014, 9 pages.
International Search Report and Written Opinion for Application No. PCT/US2015/043624, dated Oct. 6, 2015, 7 pages.
International Search Report and Written Opinion for Application No. PCT/US2016/043301, dated Oct. 17, 2016, 10 pages.
International Search Report and Written Opinion for Application No. PCT/US2018/025193, dated May 30, 2018, 10 pages.
International Search Report and Written Opinion for Application No. PCT/US2020/027724, dated Sep. 23, 2020, 18 pages.
Japanese Office Action for Application No. 2018-224481, dated Mar. 30, 2020, 7 pages.
Lubke et al., Inhibitory effects of midostaurin and avapritinib on myeloid progenitors derived from patients with Kit D816V positive advanced systemic mastocytosis. Leukemia. May 2019;33(5):1195-1205.
Pardanani, Systemic mastocytosis in adults: 2019 update on diagnosis, risk stratification and management. Am J Hematol. Mar. 2019;94(3):363-377.
Vaes et al., Targeted Treatment Options in Mastocytosis. Front Med (Lausanne). Jul. 20, 2017;4:110, 12 pages.
U.S. Appl. No. 17/070,556, filed Oct. 14, 2020, 2021-0284645, Abandoned.
U.S. Appl. No. 18/382,727, filed Oct. 23, 2023, Pending.
U.S. Appl. No. 17/292,965, filed May 11, 2021, 2022-0010382, Published.
U.S. Appl. No. 17/766,200, filed Apr. 1, 2022, Pending.
U.S. Appl. No. 17/773,447, filed Apr. 29, 2022, 2022-0370465, Published.

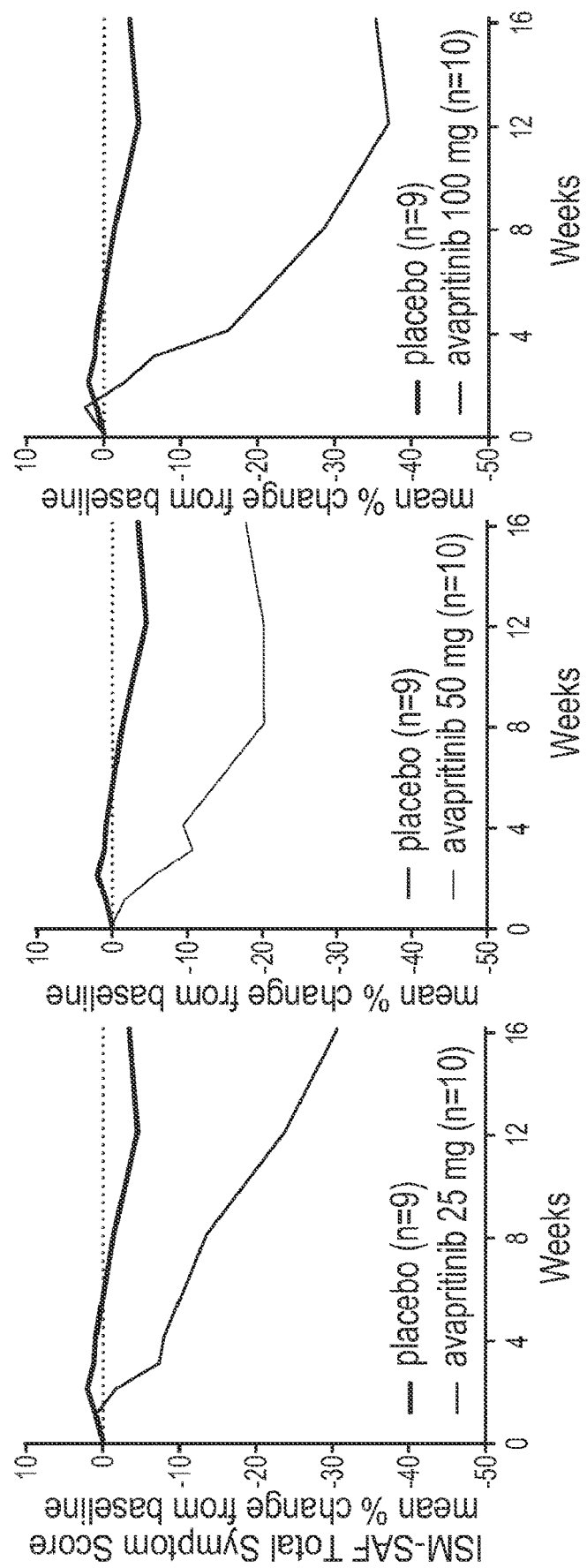

CRYSTALLINE FORMS OF (S)-1-(4-FLUOROPHENYL)-1-(2-(4-(6-(1-METHYL-1H-PYRAZOL-4-YL) PYRROLO[2,1-F][1,2,4]TRIAZIN-4-YL) PIPERAZINYL)-PYRIMIDIN-5-YL)ETHAN-1-AMINE AND METHODS OF MAKING

This application is a divisional application U.S. patent application Ser. No. 17/153,727, filed Jan. 20, 2021, which, in turn, is a continuation application of International Application No. PCT/US2020/027724, filed Apr. 10, 2020, which claims priority from U.S. Provisional Application No. 62/990,269, filed Mar. 16, 2020; U.S. Provisional Application No. 62/844,575, filed May 7, 2019; and U.S. Provisional Application No. 62/833,527, filed Apr. 12, 2019. The entire contents of each of the aforementioned applications are incorporated herein by reference.

Disclosed herein are crystalline forms of (S)-1-(4-fluorophenyl)-1-(2-(4-(6-(1-methyl-1H-pyrazol-4-yl)pyrrolo[2,1-f][1,2,4]triazin-4-yl)piperazin-yl)pyrimidin-5-yl)ethan-1-amine (Compound (I)), pharmaceutically acceptable salts thereof, and solvates of any of the foregoing compositions comprising the same, methods of using the same, and processes for making the Compound (I), including its crystalline forms. The crystalline forms of Compound (I) may be selective inhibitors of KIT, including exon 17 mutant and/or PDGFRα exon 18 mutant proteins.

The enzyme KIT (also called CD117) is a receptor tyrosine kinase expressed on a wide variety of cell types. The KIT receptor protein belongs to the class III receptor tyrosine kinase (RTK) family that also includes the structurally related proteins PDGFRα (platelet-derived growth factor receptor A), PDGFRβ, FLT3 (FMS-like tyrosine kinase 3), and CSF1R (colony-stimulating factor 1 receptor). The KIT molecule contains a long extracellular domain, a transmembrane segment, and an intracellular portion. The ligand for KIT is stem cell factor (SCF). Normally, stem cell factor (SCF) binds to and activates KIT by inducing dimerization, autophosphorylation, and initiation of downstream signaling. In several tumor types, however, somatic activating mutations in KIT drive ligand-independent constitutive activity.

KIT mutations generally occur in the DNA encoding the juxtumembrane domain (exon 11). KIT mutations also occur, with less frequency, in exons 7, 8, 9, 13, 14, 17, and 18. Mutations make KIT function independent of activation by SCF, leading to a high cell division rate and possibly genomic instability. Mutant KIT has been implicated in the pathogenesis of several disorders and conditions, e.g., mastocytosis, gastrointestinal stromal tumors (GIST), acute myeloid leukemia (AML), melanoma, and seminoma.

The structurally related platelet-derived growth factor receptors (PDGFR) are cell surface tyrosine kinase receptors for members of the platelet-derived growth factor (PDGF) family. PDGF subunits –α and –β regulate cell proliferation, cellular differentiation, cell growth, and cellular development. Alterations in PDGF subunit –α and –β (e.g., mutations) are associated with many diseases, including some cancers. For example, an exon 18 PDGFRα D842V mutation has been found in a distinct subset of GIST, typically from the stomach. The D842V mutation is also associated with tyrosine kinase inhibitor resistance. In addition, other exon 18 mutations such as PDGFRα D842I and PDGFRα D842Y are associated with ligand-independent, constitutive activation of PDGFRα. In GIST, gain of function mutations (such as, e.g., PDGFRα D842I, D842V, and D842Y) that confer ligand-independent constitutive activation of PDGFRα signaling have been identified as drivers of disease.

Compound (I), pharmaceutically acceptable salts thereof, and solvates of any of the foregoing may inhibit KIT and/or PDGFRα and be useful in the treatment of mast cell disorders such as mastocytosis, and disorders and conditions associated with oncogenic KIT and PDGFRα alterations. Compound (I) is disclosed in Example 7 of WO 2015/057873 and has the following structure:

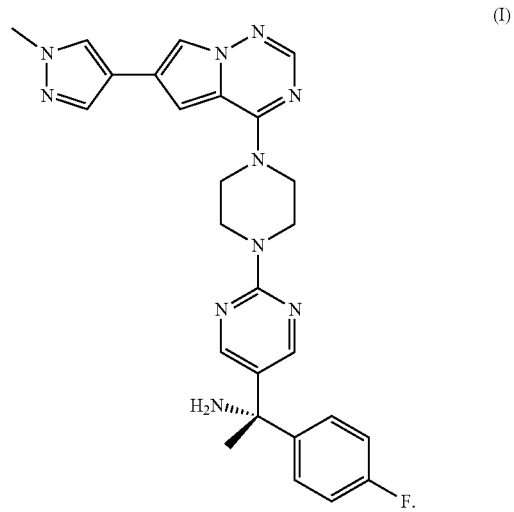 [SMILES: Cn1cc(-c2cc3c(N4CCN(c5ncc([C@@](C)(N)c6ccc(F)cc6)cn5)CC4)ncnn3c2)cn1]

(I)

The procedure described in WO 2015/057873 to produce Compound (I) uses chiral supercritical fluid chromatography (SFC) to separate the enantiomers in the final step. In general, chromatographic separations are not desirable for large-scale manufacturing processes. Furthermore, trace amounts of impurity were observed in the $^1$H NMR of Compound (I) obtained by the procedure described in WO 2015/057873.

Crystalline forms of bioactive compounds, such as Compound (I), pharmaceutically acceptable salts thereof, and solvates of any of the foregoing, are of interest in the pharmaceutical industry, where crystalline forms may be desirable or even required for pharmaceutical development. Crystalline forms occur where the same composition of matter crystallizes in different lattice arrangements, resulting in different thermodynamic properties and stabilities specific to each crystalline form. Each unique crystal form is known as a "polymorph." Crystalline forms may also include different solvates (e.g., hydrates) of the same compound. While polymorphs of a given substance have the same chemical composition, they may differ from each other with respect to at least one physical, chemical, and/or pharmaceutical property, such as solubility, dissociation, true density, dissolution, melting point, crystal habit or morphology, compaction behavior, particle size, flow properties, and/or solid state stability.

The solid state form of a bioactive compound often determines its ease of preparation, ease of isolation, hygroscopicity, stability, solubility, storage stability, ease of formulation, rate of dissolution in gastrointestinal fluids, and in vivo bioavailability. For example, if an unstable crystalline form is used during large-scale manufacturing, crystal morphology may change during manufacture and/or storage, resulting in quality control problems and formulation irregularities. Unstable crystalline forms may affect the development of a pharmaceutical for human use. Therefore, any change to the solid state of a bioactive compound that improves its physical or chemical stability may impart a significant advantage over less stable forms of the same compound.

Furthermore, it is critical that crystalline forms that are to be used as active pharmaceutical ingredients (APIs) in therapeutic compositions are substantially pure. Specifically, substantially pure crystalline forms are free from reaction impurities, starting materials, reagents, side products, unwanted solvents and/or other processing impurities arising from the preparation and/or isolation and/or purification of the particular crystalline form.

It is not yet possible to predict whether a particular compound, salt, or hydrate of a compound will form a crystalline form, how many different crystalline forms there will be, whether any such crystalline forms will be suitable for commercial use in a pharmaceutical composition or which crystalline form or forms will display desirable properties. Because different crystalline forms may possess different properties, reproducible processes for producing a substantially pure crystalline form, i.e., not a mixture of forms, including large-scale manufacturing processes are also desirable for bioactive compounds intended to be used in pharmaceuticals.

Accordingly, there is a need for novel crystalline forms which are useful for treating mast cell disorders associated with mutant/oncogenic KIT and PDGFRA, including mastocytosis, and disorders and conditions associated with mutant/oncogenic KIT and PDGFRA alterations, e.g., Compound (I), pharmaceutically acceptable salts thereof, and solvates of any of the foregoing.

Disclosed herein are novel crystalline forms of Compound (I), pharmaceutically acceptable salts thereof, and solvates of any of the foregoing, compositions comprising the same, and methods of using and making the same. Importantly, the crystalline forms of Compound (I) for pharmaceutical use are substantially free of impurities. In some embodiments, the novel crystalline forms disclosed herein have properties that are useful for large-scale manufacturing, pharmaceutical formulation, and/or storage. In some embodiments, the novel crystalline forms disclosed herein consist of one crystalline form. The crystalline forms are substantially pure. Also disclosed herein are novel methods of making Compound (I).

Some embodiments of the disclosure relate to a pharmaceutical composition comprising: a pharmaceutically acceptable excipient; and at least one crystalline form which is chosen from crystalline forms of Compound (I), pharmaceutically acceptable salts thereof, and solvates of any of the foregoing. In some embodiments, the at least one crystalline form is crystalline Form A of Compound (I). In some embodiments, the at least one crystalline form is crystalline Form B of Compound (I). In some embodiments, the at least one crystalline form is crystalline Form C of Compound (I). In some embodiments, the at least one crystalline form is crystalline Form O of Compound (I). In some embodiments, the at least one crystalline form is crystalline Form T of a tosylate salt of Compound (I). In some embodiments, the at least one crystalline form is crystalline Form Tr of a tartrate salt of Compound (I). In some embodiments, the at least one crystalline form is crystalline Form H of a hydrochloride salt of Compound (I).

Some embodiments of the disclosure relate to methods of treating a patient in need of a KIT or PDGFRα inhibitor by administering a therapeutically effective amount of at least one crystalline form chosen from crystalline forms of Compound (I), pharmaceutically acceptable salts thereof, and solvates of any of the foregoing. In some embodiments, the at least one crystalline form is crystalline Form A of Compound (I). In some embodiments, the at least one crystalline form is crystalline Form B of Compound (I). In some embodiments, the at least one crystalline form is crystalline Form C of Compound (I). In some embodiments, the at least one crystalline form is crystalline Form O of Compound (I). In some embodiments, the at least one crystalline form is crystalline Form T of a tosylate salt of Compound (I). In some embodiments, the at least one crystalline form is crystalline Form Tr of a tartrate salt of Compound (I). In some embodiments, the at least one crystalline form is crystalline Form H of a hydrochloride salt of Compound (I).

In some embodiments, the patient in need of a KIT or PDGFRα inhibitor is suffering from a disorder or condition associated with at least one oncogenic KIT and/or PDGFRA alteration. In some embodiments, the patient in need of a KIT or PDGFRα, inhibitor is suffering from PDGFRA exon 18 positive unresectable or metastatic GIST. In some embodiments, the at least one oncogenic KIT and/or PDGFRA alteration is a genetic mutation in Exon 18 of PDGFRA. In some embodiments, the at least one oncogenic KIT and/or PDGFRα alteration is a D842V mutation in PDGFRA protein. In some embodiments, the at least one oncogenic KIT and/or PDGFRα alteration is a D842I mutation in PDGFRA protein. In some embodiments, the at least one oncogenic KIT and/or PDGFRα alteration is a D842Y mutation in PDGFRA protein.

In some embodiments, the at least one oncogenic KIT and/or PDGFRA alteration is a non-D842 alteration in Exon 18 of PDGFRα. In some embodiments, the at least one oncogenic KIT and/or PDGFRA alteration is an indel in PDGFRA protein. In some embodiments, the at least one oncogenic KIT and/or PDGFRA alteration is D842-H845 in PDGFRA protein. In some embodiments, the at least one oncogenic KIT and/or PDGFRA alteration is DI842-843V in PDGFRA protein. In some embodiments, the at least one oncogenic KIT and/or PDGFRA alteration is a genetic mutation in Exon 17 of KIT. In some embodiments, the at least one oncogenic KIT and/or PDGFRA alteration is d557-558 in KIT protein. In some embodiments, the at least one oncogenic KIT and/or PDGFRA alteration is V560G in KIT protein. In some embodiments, the at least one oncogenic KIT and/or PDGFRA alteration is V560G/D816V in KIT protein. In some embodiments, the at least one oncogenic KIT and/or PDGFRA alteration is V560G/N822K in KIT protein. In some embodiments, the at least one oncogenic KIT and/or PDGFRα alteration is a D816 mutation in KIT protein. In some embodiments, the at least one oncogenic KIT and/or PDGFRα alteration is a D816V mutation in KIT protein. In some embodiments, the at least one oncogenic KIT and/or PDGFRA alteration is D816E in KIT protein. In some embodiments, the at least one oncogenic KIT and/or PDGFRA alteration is D816F in KIT protein. In some embodiments, the at least one oncogenic KIT and/or PDGFRA alteration is D816H in KIT protein. In some embodiments, the at least one oncogenic KIT and/or PDGFRA alteration is D816I in KIT protein. In some embodiments, the at least one oncogenic KIT and/or PDGFRα alteration is D816Y in KIT protein. In some embodiments, the at least one oncogenic KIT and/or PDGFRα alteration is D820E in KIT protein. In some embodiments, the at least one oncogenic KIT and/or PDGFRα alteration is D820Y in KIT protein. In some embodiments, the at least one oncogenic KIT and/or PDGFRα alteration is Y823D in KIT protein. In some embodiments, the disorder or condition associated with at least one oncogenic KIT and/or PDGFRA alteration is gastrointestinal stromal tumor (GIST). In some embodiments, the patient is refractory to treatment with imatinib. In some embodiments, the patient has been treated with at least 3 prior lines of therapy. In some embodiments, the patient is refractory to treatment with imatinib, sunitinib, and/or regorafenib. In some embodiments, the patient has unresectable GIST. In some embodiments, the patient has metastatic GIST. In some embodiments, the disorder or condition associated with at least one oncogenic KIT and/or PDGFRA alteration is acute myeloid leukemia.

In some embodiments, the disorder or condition associated with at least one mutant/oncogenic KIT and/or PDGFRA alteration is mastocytosis. In some embodiments, the mastocytosis is chosen from cutaneous mastocytosis (CM) and systemic mastocytosis (SM). In some embodiments, the systemic mastocytosis is chosen from indolent systemic mastocytosis (ISM), smoldering systemic mastocytosis (SSM), and advanced systemic mastocytosis (AdvSM). AdvSM includes aggressive systemic mastocytosis (ASM), SM with associated hematologic non-mast cell lineage disease (SM-AHNMD), and mast cell leukemia (MCL). In some embodiments, the systemic mastocytosis is indolent systemic mastocytosis (ISM). In some embodiments, the systemic mastocytosis is advanced systemic mastocytosis (AdvSM). In some embodiments, the systemic mastocytosis is smoldering systemic mastocytosis (SSM). In some embodiments, the systemic mastocytosis is aggressive systemic mastocytosis (ASM). In some embodiments, the systemic mastocytosis is SM with associated hematologic non-mast cell lineage disease (SM-AHNMD). In some embodiments, the systemic mastocytosis is mast cell leukemia (MCL).

Disclosed herein are improved methods for treating indolent systemic mastocytosis (ISM) and smoldering systemic mastocytosis (SSM) in patients with Compound (I). In some embodiments, the disclosure provides dosing regimens of Compound (I) for the treatment of ISM and SSM. More specifically, the disclosure provides methods for treating ISM and SSM in patients identified as having moderate-to-severe symptoms based on a minimum mean Total Symptom Score (TSS) as accessed by the Indolent Systemic Mastocytosis-Symptom Assessment Form (ISM-ASF) by administering Compound (I) at a once daily dose of 10 to 100 mg.

There are no approved treatments for ISM and SSM. Symptoms are managed with symptom-directed therapies, such as antihistamines. Thus, there is a need for safe, effective treatments for ISM and SSM. Furthermore, since ISM and SSM patients have lower disease burden than AdvSM patients and are expected to remain on treatment for long periods of time, there is a need for low doses, if efficacious.

The FDA approved dose for Compound (I) (AYVAKIT™ or avapritinib) for the treatment of adults with unresectable or metastatic GIST harboring a PDGFRA exon 18 mutation, including PDGFRA D842V mutations is 300 mg orally QD. A Phase 2 clinical trial is currently evaluating the efficacy and safety of Compound (I) doses at 200-300 mg orally QD in patients with advanced systemic mastocytosis (AdvSM). According to the latest clinical study as shown in the example provided herein, it has now been found that 25 mg of Compound (I) dosed once daily in patients with ISM or SSM shows improvement across all three aspects of its clinical profile, including reduction in mast cell burden, improvement of disease symptoms, and improvement in quality of life. Specifically, 25 mg of Compound (I) dosed once daily has a statistically significant reduction in ISM-SAF TSS and each symptom in the total domain score at 16 weeks. Surprisingly, the 25 mg dose provided similar mean improvements in TSS as the higher doses of 50 mg and 100 mg and better tolerability. For example, similar to the 50 mg QD dose and 100 mg QD dose, the 25 mg QD dose shows significant reduction in blood KIT D816V allele fraction. Moreover, 25 mg of Compound (I) dosed once daily in patients has a favorable safety profile in patients with ISM. For example, 95% of patients remain on the clinical study, with no discontinuations for adverse effects (AEs). No grade≥3 AEs occurred in the 25 mg once daily cohort. Patients have improvements in quality of life (QoL), as measured by MC-QoL overall score and all domain scores, at week 16.

Also disclosed herein are methods of preparing at least one crystalline form chosen from crystalline forms of Compound (I), pharmaceutically acceptable salts thereof, and solvates of any of the foregoing. Some embodiments of the disclosure are directed to said methods, wherein the at least one crystalline form is crystalline Form A of Compound (I). Some embodiments of the disclosure are directed to said methods, wherein the at least one crystalline form is crystalline Form B of Compound (I). Some embodiments of the disclosure are directed to said methods, wherein the at least one crystalline form is crystalline Form C of Compound (I). Some embodiments of the disclosure are directed to said methods, wherein the at least one crystalline form is crystalline Form O of Compound (I). Some embodiments of the disclosure are directed to said methods, wherein the at least one crystalline form is crystalline Form T of a tosylate salt of Compound (I). Some embodiments of the disclosure are directed to said methods, wherein the at least one crystalline form is crystalline Form Tr of a tartrate salt of Compound (I). Some embodiments of the disclosure are directed to said methods, wherein the at least one crystalline form is crystalline Form H of a hydrochloride salt of Compound (I).

BRIEF DESCRIPTION OF THE DRAWINGS

FIG. 14A shows ISM-SAF Total Symptom Score reduction from base line (the dotted line) in patients administered 25 mg once daily Compound (I). The top line represents placebo, the bottom line represents Compound (I) 25 mg once daily dose. FIG. 14B shows ISM-SAF Total Symptom Score reduction from base line (the dotted line) in patients administered 50 mg once daily Compound (I). The top line represents placebo, the bottom line represents Compound (I) 50 mg once daily dose. FIG. 14C shows ISM-SAF Total Symptom Score reduction from base line (the dotted line) in patients administered 100 mg once daily Compound (I). The top line represents placebo, the bottom line represents Compound (I) 100 mg once daily dose.

Figure 1:
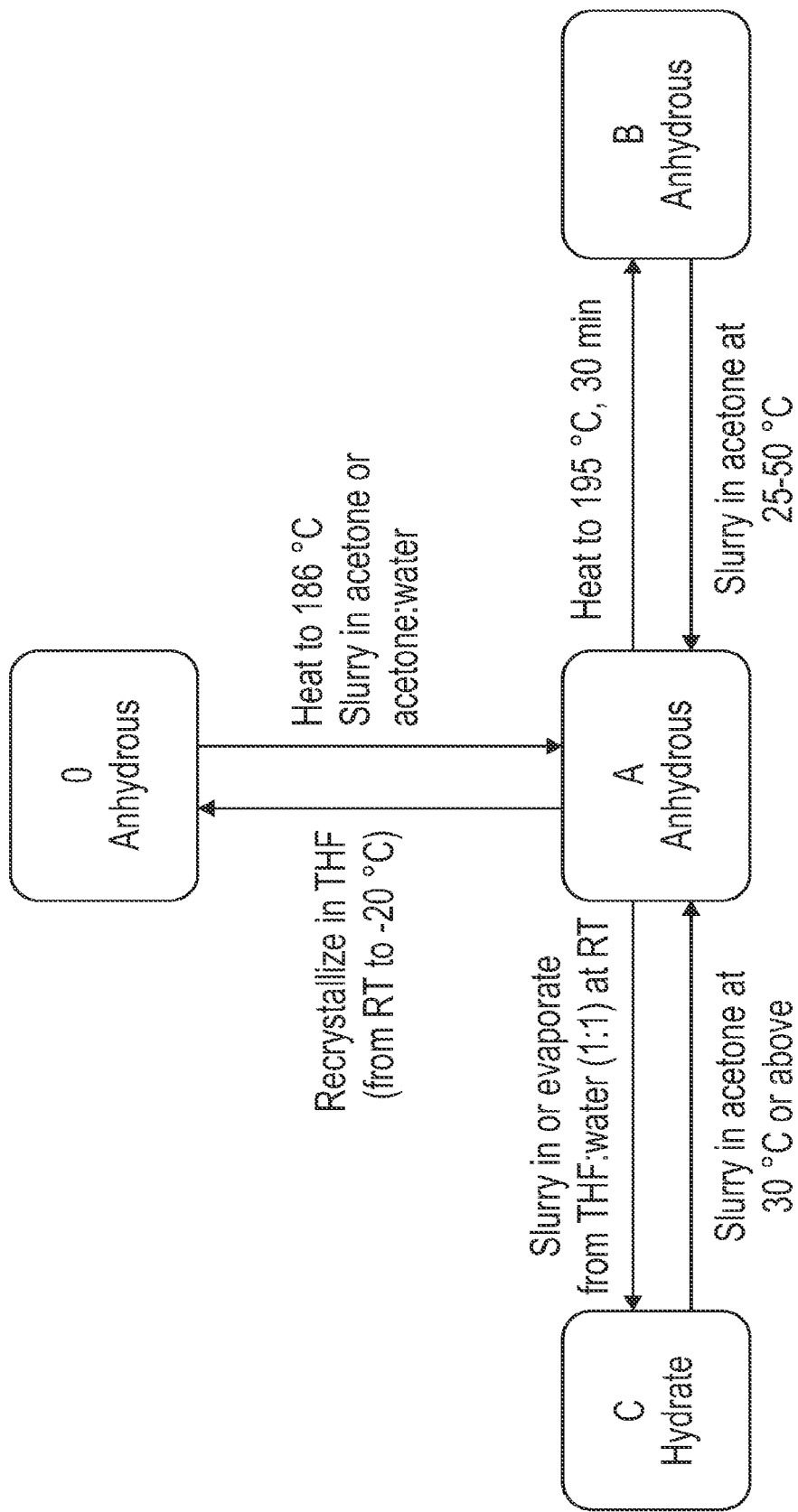
FIG. 1 is a schematic showing the interrelation of four crystalline forms, as well as non-limiting examples of how to prepare the crystalline forms. As indicated in FIG. 1, crystalline Form A, crystalline Form B, and crystalline Form O of Compound (I) are all anhydrous.

Compound (I) was developed to selectively target KIT D816V and other KIT exon 17 mutations. In some embodiments, Compound (I) is amorphous. In some embodiments, Compound (I) is crystalline. In some embodiments, Compound (I) is a mixture of crystalline forms. Compound (I) is approved by the FDA for the treatment of adults with unresectable or metastatic gastrointestinal stromal tumor (GIST) harboring a PDGFRA exon 18 mutation, including PDGFRA D842V mutations at 400 mg once a day (QD). Compound (I) has also demonstrated a potent and selective activity in vitro against KIT D816V, robust growth inhibition in a tyrosine kinase inhibitor (TKI)-resistant mastocytoma model in vivo, and tolerability at active doses in toxicology and safety pharmacology studies. An ongoing Phase 1 study of Compound (I) in patients with AdvSM (Explorer/NCT02561988) is evaluating safety and preliminary efficacy. The recommended Phase 2 dose (RP2D) was identified as 300 mg once a day, and an expansion cohort of the study is further evaluating efficacy and safety of this dose in a larger cohort of patients, as well as validating the AdvSM Symptom Assessment Form (AdvSM-SAF) that has been developed to assess the impact of Compound (I) on symptom improvement in patients with AdvSM. Based on emerging safety and efficacy data in patients treated at 300 mg QD, an additional cohort of patients treated at 200 mg QD was added.

As used herein, the term "pharmaceutically acceptable salt" refers to a non-toxic salt form of a compound of this disclosure. Pharmaceutically acceptable salts of Compound (I) of this disclosure include those derived from suitable inorganic and organic acids and bases. Pharmaceutically acceptable salts are well known in the art. Suitable pharmaceutically acceptable salts are, e.g., those disclosed in Berge, S. M., et al. *J. Pharma. Sci.* 66:1-19 (1977). Non-limiting examples of pharmaceutically acceptable salts disclosed in that article include: acetate; benzenesulfonate; benzoate; bicarbonate; bitartrate; bromide; calcium edetate; camsylate; carbonate; chloride; citrate; dihydrochloride; edetate; edisylate; estolate; esylate; fumarate; gluceptate; gluconate; glutamate; glycollylarsanilate; hexylresorcinate; hydrabamine; hydrobromide; hydrochloride; hydroxynaphthoate; iodide; isethionate; lactate; lactobionate; malate; maleate; mandelate; mesylate; methylbromide; methylnitrate; methylsulfate; mucate; napsylate; nitrate; pamoate (embonate); pantothenate; phosphate/diphosphate; polygalacturonate; salicylate; stearate; subacetate; succinate; sulfate; tannate; tartrate; teociate; triethiodide; benzathine; chloroprocaine; choline; diethanolamine; ethylenediamine; meglumine; procaine; aluminum; calcium; lithium; magnesium; potassium; sodium; and zinc.

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Additional non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Non-limiting examples of pharmaceutically acceptable salts derived from appropriate bases include alkali metal, alkaline earth metal, ammonium, and $N^+(C_{1-4}\ alkyl)_4$ salts. This disclosure also envisions the quaternization of any basic nitrogen-containing groups of the compounds disclosed herein. Non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other non-limiting examples of pharmaceutically acceptable salts include besylate and glucosamine salts.

As used herein, the term "ambient conditions" means room temperature, open air condition, and uncontrolled humidity condition. As used herein, the term "room temperature" or "ambient temperature" means a temperature ranging from 15° C. to 30° C.

As used herein, the terms "polymorph," "crystal form," "crystalline form," "solid state form," and "Form" interchangeably refer to a solid having a particular molecular packing arrangement in the crystal lattice. Crystalline forms can be identified and distinguished from each other by at least one characterization technique including, e.g., X-ray powder diffraction (XRPD), single crystal X-ray diffraction, differential scanning calorimetry (DSC), dynamic vapor sorption (DVS), and/or thermogravimetric analysis (TGA). Accordingly, as used herein, the terms "crystalline Form [X] of Compound (I)," "crystalline Form [Y] of a [pharmaceutically acceptable] salt of Compound (I), and "crystalline Form [Z] of Compound (I) [solvate]" refer to unique crystalline forms that can be identified and distinguished from each other by at least one characterization technique including, e.g., X-ray powder diffraction (XRPD), single crystal X-ray diffraction, differential scanning calorimetry (DSC), dynamic vapor sorption (DVS), and/or thermogravimetric analysis (TGA). In some embodiments, the novel crystalline forms are characterized by an X-ray powder diffractogram having at least one signal at at least one specified two-theta value (° 2θ).

As used herein, the term "solvate" refers to a crystalline form of a molecule, atom, and/or ion further comprising at least one molecule of a solvent or solvents incorporated into the crystalline lattice structure in stoichiometric or nonstoichiometric amounts. The solvent molecules in the solvate may be present in a regular arrangement and/or a non-ordered arrangement. For example, a solvate with a non-stoichiometric amount of solvent molecules may result from partial loss of solvent from the solvate. Alternatively, solvates may occur as dimers or oligomers comprising more than one molecule. When the solvent is water, the solvate is referred to herein as a "hydrate."

As used herein, the term "XRPD" refers to the analytical characterization method of X-ray powder diffraction. XRPD patterns can be recorded at ambient conditions in transmission or reflection geometry using a diffractometer.

As used herein, the terms "X-ray powder diffractogram," "X-ray powder diffraction pattern," and "XRPD pattern" refer to an experimentally obtained pattern plotting signal positions (on the abscissa) versus signal intensities (on the ordinate). For an amorphous material, an X-ray powder diffractogram may include at least one broad signal. For a crystalline material, an X-ray powder diffractogram may include at least one signal, each identified by its angular value as measured in degrees 2θ (° 2θ), depicted on the abscissa of an X-ray powder diffractogram, which may be expressed as "a signal at . . . degrees two-theta," "a signal at [a] two-theta value(s) of . . . " and/or "a signal at at least . . . two-theta value(s) chosen from . . . ."

A used herein, the term "X-ray powder diffractogram having a signal at . . . two-theta values" refers to an XRPD pattern that contains X-ray reflection positions as measured and observed in X-ray powder diffraction experiments (° 2θ).

As used herein, the term "signal" refers to a point in the XRPD pattern where the intensity as measured in counts is at a local maximum. One of ordinary skill in the art would recognize that at least one signal in an XRPD pattern may overlap and may, for example, not be apparent to the naked eye. One of ordinary skill in the art would recognize that some art-recognized methods are capable of and suitable for determining whether a signal exists in a pattern, such as, e.g., Rietveld refinement.

As used herein, the terms "a signal at . . . degrees two-theta," "a signal at [a] two-theta value[ ] of . . . ," and "a signal at at least . . . two-theta value(s) chosen from . . . ." refer to X-ray reflection positions as measured and observed in X-ray powder diffraction experiments (° 2θ). In some embodiments, the repeatability of the angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta). It is well known to one of ordinary skill in the art that there can be variability in the measurements of X-ray powder diffraction signal values. As such, a person of ordinary skill in the art would appreciate that there may be variability of up to ±0.2° 2θ in signal value for the same signal in different samples. As used herein, the terms "signal intensities" refer to relative signal intensities within a given X-ray powder diffractogram. Factors that can affect the relative signal intensities include, e.g., sample thickness and preferred orientation (e.g., the crystalline particles are not distributed randomly).

As used herein, the term "amorphous" refers to a solid material having no long range order in the position of its molecules. For example, an amorphous material is a solid material having no sharp signal(s) in its X-ray power diffractogram (i.e., is not crystalline as determined by XRPD). Amorphous refers to a solid form that is not crystalline. Instead, at least one broad signal (e.g., at least one halo) may appear in its diffractogram. Broad signals are characteristic of an amorphous solid.

As used herein, an X-ray powder diffractogram is "substantially similar to that in [a particular] Figure" when at least 90%, such as at least 95%, at least 98%, or at least 99%, of the signals in the two diffractograms are the same±0.2° 2θ. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta (° 2θ) referred to herein) generally mean that value reported ±0.2 degrees 2θ of the reported value, an art-recognized variance discussed above.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 98% of the sum of all solid form(s) in a sample. In some embodiments, the solid form is "substantially pure" when it accounts for an amount by weight equal to or greater than 99% of the sum of all solid form(s) in a sample.

In some embodiments, the solid form is "substantially pure" when it accounts for an amount by weight equal to or greater than 98.0% of the sum of all solid organic form(s) in a sample. As used herein "solid organic form(s)" excludes water, elementals, solvents, and Compound (I)'s enantiomer. As used herein, the "enantiomer" of Compound (I) is Compound (E), which has the following chemical structure:

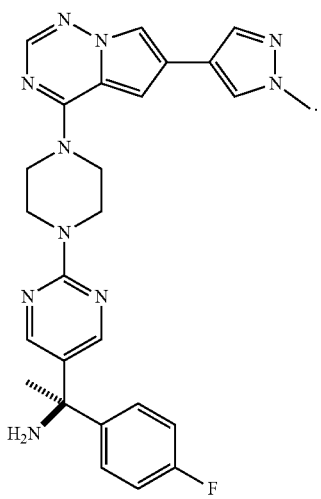

(E)

In some embodiments, the solid form is "substantially pure" when it has ≤0.8% w/w, ≤0.7% w/w, ≤0.6% w/w, ≤0.55% w/w of its undesired enantiomer (Compound (E)).

In some embodiments, the solid form is "substantially pure" when it has no more than 2.0% w/w total impurities. In some embodiments, the solid form is "substantially pure" when it has not more than 0.15% w/w of each known unspecified impurity. Known unspecified impurities include, e.g., impurity (I-A):

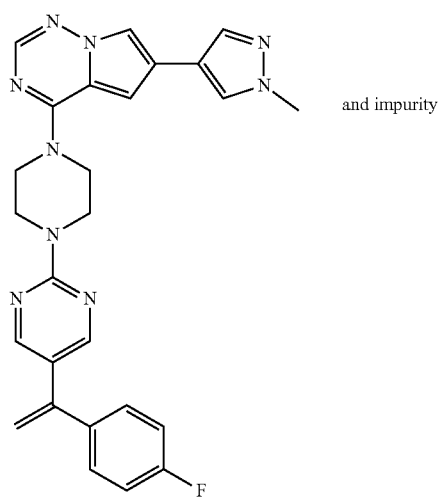

(I-A)

and impurity

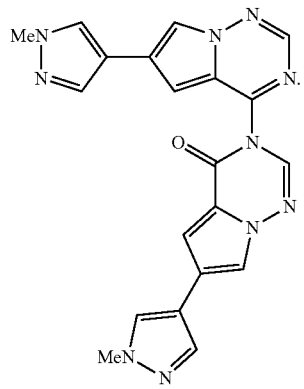

(I-B)

In some embodiments, the solid form is "substantially pure" when it has not more than 0.55 area/area of Compound (E). In some embodiments, the solid form is "substantially pure" when it has not more than 0.15% w/w of each known unspecified impurity and not more than 0.10% w/w of any other individual impurity. In some embodiments, the solid form is "substantially pure" when it has not more than 0.15% w/w of each known unspecified impurity and not more than 0.10% w/w of any other individual impurity, and not more than 0.55 area/area of Compound (E).

In some embodiments, the solid form is "substantially pure" when it is essentially free of solvent, e.g., the solid form has not more than 3000 ppm methanol, not more than 5000 ppm 2-propanol, not more than 600 ppm dichloromethane, not more than 720 ppm tetrahydrofuran, not more than 620 ppm 2-methyltetrahydrofuran, not more than 5000 ppm acetone, not more than 5000 ppm heptane, not more than 5000 ppm methyl tert-butyl ether, not more than 890 ppm toluene, or not more than 380 ppm 1,4-dioxane.

In some embodiments, N,N-diisopropylethylamine (DIPEA) is a tertiary amine which may be used in the last step of the processing step of Compound (I). In some embodiments, the solid form is "substantially pure" when it is essentially free of DIPEA. In some embodiments, the solid form is "substantially pure" when the solid form has not more than 1000 ppm of DIPEA.

In some embodiments, the solid form is "substantially pure" when it is 97.0% to 103.0% w/w solvent-free, anhydrous basis (calculation includes correction for water, residual solvents and DIPEA content) by HPLC. HPLC retention time must be ±2% of that of the standard. HPLC analysis may be performed, e.g., as described below:

| First generation HPLC method: | |
| --- | --- |
| Column: | XBridge XB-C18, 4.6 × 150 mm, 3.5 μm |
| Column Temperature: | 15° C. |
| Auto Sampler Temperature: | Ambient |
| Detection: | 253 nm |
| Mobile Phase A: | 10 mM sodium bicarbonate |
| Mobile Phase B: | Acetonitrile |
| Flow Rate: | 0.8 mL/min |
| Injection Volume: | 5 μL |
| Run Time: | 20 min |
| Sample Diluent: | 85:15 (v/v) acetonitrile:water |
| Sample Concentration: | 0.1 mg/mL |
| Approximate Retention Time for Compound (I) | 9.8 min |

-continued

Gradient Program:

| Time (min) | % A | % B |
|---|---|---|
| 0.00 | 95 | 5 |
| 12.00 | 5 | 95 |
| 15.00 | 5 | 95 |
| 15.10 | 95 | 5 |
| 20.00 | 95 | 5 |

Second generation HPLC method

| | |
|---|---|
| Column: | XBridge XB-C18, 4.6 × 150 mm, 3.5 μm |
| Column Temperature: | 15° C. |
| Auto Sampler Temperature: | Ambient |
| Detection: | 253 nm |
| Mobile Phase A: | 0.1% trifluoroacetic acid in water |
| Mobile Phase B: | 0.1% trifluoroacetic acid in acetonitrile |
| Flow Rate: | 0.8 mL/min |
| Injection Volume: | 5 μL |
| Run Time: | 20 min |
| Sample Diluent: | 50:50 (v/v) acetonitrile:water |
| Sample Concentration: | 0.1 mg/mL |
| Approximate Retention Time for Compound (I) | 7.4 min |

Gradient Program:

| Time (min) | % A | % B |
|---|---|---|
| 0.00 | 95 | 5 |
| 12.00 | 5 | 95 |
| 15.00 | 5 | 95 |
| 15.10 | 95 | 5 |
| 20.00 | 95 | 5 |

As used herein, a "selective KIT inhibitor" or a "selective PDGFRα inhibitor" refers to a compound or a pharmaceutically acceptable salt thereof or a solvate of any of the foregoing that selectively inhibits a KIT protein kinase or PDGFRα protein kinase over another protein kinase and exhibits at least a 2-fold selectivity for a KIT protein kinase or a PDGFRα protein kinase over another kinase. For example, a selective KIT inhibitor or a selective PDGFRA inhibitor exhibits at least a 10-fold selectivity; at least a 15-fold selectivity; at least a 20-fold selectivity; at least a 30-fold selectivity; at least a 40-fold selectivity; at least a 50-fold selectivity; at least a 60-fold selectivity; at least a 70-fold selectivity; at least a 80-fold selectivity; at least a 90-fold selectivity; at least 100-fold, at least 125-fold, at least 150-fold, at least 175-fold, or at least 200-fold selectivity for a KIT protein kinase or a PDGFRα kinase over another kinase. In some embodiments, a selective KIT inhibitor or a selective PDGFRα inhibitor exhibits at least 150-fold selectivity over another kinase, e.g., VEGFR2 (vascular endothelial growth factor receptor 2), SRC (Non-receptor protein tyrosine kinase), and FLT3 (Fms-Like Tyrosine kinase 3). In some embodiments, selectivity for a KIT protein kinase or a PDGFRα protein kinase over another kinase is measured in a cellular assay (e.g., a cellular assay). In some embodiments, selectivity for a KIT protein kinase or a PDGFRα protein kinase over another kinase is measured in a biochemical assay (e.g., a biochemical assay).

As used herein, "a therapeutically effective amount" of a compound disclosed herein refers to an amount of the compound that will elicit a biological or medical response in a subject, e.g., reduction or inhibition of enzyme or protein activity, or ameliorate symptoms, alleviate conditions, or slow or delay disease progression. In some embodiments, "a therapeutically effective amount" refers to the amount of the compound that, when administered to a subject, is effective to (1) at least partially alleviate, inhibit, and/or ameliorate a disorder or condition (i) mediated by KIT and/or PDGRFA, or (ii) associated with KIT and/or PDGFRA activity, or (iii) characterized by activity (normal or abnormal) of KIT and/or PDGFRA; or (2) reduce or inhibit the activity of KIT and/or PDGFRα protein kinase. In some embodiments, "a therapeutically effective amount" refers to the amount of the compound that, when administered to a cell, or a tissue, or a non-cellular biological material, or a medium, at least partially reduces or inhibits the activity of KIT and/or PDGFRα protein kinase. The therapeutically effective amount will depend on the purpose of the treatment and will be ascertainable by one of ordinary skill in the art (see, e.g., Lloyd (1999) The Art, Science and Technology of Pharmaceutical Compounding).

As used herein, the term "inhibit," "inhibition," or "inhibiting" refers to the reduction or suppression of a given condition, symptom, or disorder, or disease, or a significant decrease in the baseline activity of a biological activity or process.

As used herein, the term "patient" or "subject" refers to an organism to be treated by the methods of the present disclosure. Non-limiting example organisms include mammals, e.g., murines, simians, equines, bovines, porcines, canines, felines, and the like. In some embodiments, the organism is a human. In some embodiments, the patient to be treated has ISM or SSM with moderate-to-severe symptoms that cannot be adequately controlled with approved symptom-directed therapies.

As used herein, the term "treat," "treating," or "treatment," when used in connection with a disorder or condition, includes any effect, e.g., lessening, reducing, modulating, ameliorating, and/or eliminating, that results in the improvement of the disorder or condition. Improvements in or lessening the severity of any symptom of the disorder or condition can be readily assessed according to standard methods and techniques known in the art.

In some embodiments, treatment comprises a reduction of mast cell burden. In some embodiments, objective measures of mast cell burden include serum tryptase, bone marrow mast cell numbers, skin mast cell infiltrates, and KIT D816V mutant allele burden in blood. In some embodiments, objective measures of mast cell burden include serum tryptase, bone marrow mast cell numbers, and KIT D816V mutant allele burden in blood.

In some embodiments, treatment comprises a reduction of systemic mastocytosis symptoms. Systemic mastocytosis symptoms include, but are not limited to, pruritus, flushing, GI cramping, diarrhea, anaphylaxis (especially to bee venom), bone pain, osteoporosis, and urticarial pigmentosa. In some embodiments, an ISM-SAF patient reported outcome (PRO) instrument as defined herein is used to assess symptom improvement. In some embodiments, the patient completes the ISM-SAF once a day prior to receiving treatment and the patient also completes the ISM-SAF once a day while on treatment. For example, the patient completes the ISM-SAF for a period of time, e.g., four weeks, beginning at the time of informed consent, during which time best-supportive care (BSC) medications are optimized and stabilized. Once data from the period of time, e.g., four weeks, are collected, the ISM-SAF is completed once a day for an additional period of time, e.g., two weeks (14 days), and patient eligibility is determined based on the ISM-SAF symptom threshold. Patients meeting the ISM-SAF threshold for eligibility then complete the ISM-SAF once a day while screening procedures are completed to assess study eligibility.

Once all screening procedures are completed, baseline symptoms are collected for a period of time, e.g., 14 days, immediately preceding study entry. These data are used as a Baseline Total Symptom Score (TSS). The ISM-SAF is completed by the patient once a day through completion the study, e.g., through Part 1 and Part 2, and through Week 52 in Part 3. In some embodiments, the primary endpoint for Part 2 of the study is mean change in ISM-SAF TSS from Baseline to Week 12. In some embodiments, treatment improves the number of episodes of anaphylaxis. In some embodiments, an "episode of anaphalaxis" is an episode of anaphylaxis treated with epinephrine.

In some embodiments, treatment improves quality of life (QoL) as measured by one or more questionnaires. Non-limiting examples of QoL questionnaires include the MC-QoL, the PGIS, the SF-12, the PGIC, and the EQ-5D-EL. The MC-QoL is a disease-specific QoL tool developed specifically for use in patients with ISM and CM (Siebenhaar, F. et al., *Allergy* 71(6):869-77 (2016)). The MC-QoL contains 27 items assessing four domains: symptoms, emotions, social life/functioning, and skin. Items are assessed on a 5-point scale with a recall period of two weeks. The PGIS is a single-item scale that assesses a patient's perception of disease symptoms at a point in time. The PGIS has been widely used to evaluate a patient's overall sense of whether a treatment has been beneficial. The SF-12 was developed for the Medical Outcomes Study, a multiyear study of patients with chronic conditions. The instrument was designed to reduce respondent burden, while achieving minimum standards of precision for purposes of group comparisons involving multiple health dimensions. The questionnaire measures health and well-being using 8 health domains from the patient's perspective. The recall period is four weeks. The PGIC is a single-item scale that assesses a patient's perception of change in disease symptoms at a point in time. The EQ-5D-5L is a standardized instrument for measuring generic health status. It is made up of two components: health state description and evaluation. Health status is measured in terms of five dimensions (5D): mobility; self-care; usual activities; pain/discomfort; and anxiety/depression. Respondents self-rate their level of severity for each dimension using a 5-point scale. The recall period is "today" (Whynes, D. K., *Health Qual Life Outcomes* 6:94 (2008)).

In some embodiments, treatment improves bone density. Bone density is measured by a dual-energy x-ray absorptiometry scan assessing both lumbar spine and hip. In some embodiments, treatment does not affect bone density.

As used herein, "SD" means stable disease.

As used herein, "CR" means complete response.

As used herein, "PFS" means progression free survival.

The term "systemic mastocytosis" or "SM" refers to a clonal disorder of mast cells (MCs) characterized by increased MC burden, with focal and/or diffuse infiltrates of neoplastic MCs in the skin, bone marrow (BM), spleen, liver, gastrointestinal (GI) tract, and other organs, and increased release of MC mediators. All patients have BM involvement. The World Health Organization (WHO) has established criteria for the diagnosis and classification of SM. In the most recently proposed WHO update (Valent, P. et al, *Blood* 129(11):1420-27 (2017)), SM is subclassified as indolent SM (ISM), smoldering SM (SSM), SM with an associated hematologic neoplasm of non-MC lineage (SM-AHN), aggressive SM (ASM), and MC leukemia (MCL). The latter three subclassifications are associated with reduced overall survival and are grouped together as advanced SM (AdvSM). Advanced SM is associated with a poor prognosis, with median overall survival of 3.5 years in ASM, two years in SM-AHN, and less than six months in MCL. ISM is associated with a normal or near-normal life-expectancy and the prognosis of SSM is intermediate (Lim, K. H. et al., *Blood* 113(23):5727-36 (2009)). The major criterion for SM is the multifocal accumulation and clustering of MCs in the BM or other extracutaneous organs. Minor criteria confirm the clonal nature of the disease and include abnormal MC morphology (spindling), expression of CD2 and/or CD25 in MCs, expression of an activating mutation in codon 816 of V-kit Hardy-Zuckerman 4 feline sarcoma viral oncogene homolog (KIT) exon 17 (usually D816V) and a serum tryptase level>20 ng/mL. Advanced SM is characterized by the presence of organ damage due to MC infiltration (C-findings), whereas ISM and SSM are not associated with organ function impairment.

ISM is defined by the presence of less than two B-findings per WHO criteria and no C-findings; SSM is defined by the presence of two or more B-findings and no C-findings (Valent, P. et al, *Blood* 129(11):1420-27 (2017)). The B-findings include: 1. Tryptase>200 ng/ml and bone marrow infiltration>30%, 2. Presence of hepatomegaly or splenomegaly without hypersplenism or liver dysfunction, 3. Presence of mild dysplastic changes or hypercellular marrow without meeting a WHO category of another hematologic disorder such as myelodysplastic syndrome (MDS) or myeloproliferative neoplasms (MPN). ISM is the most common category of SM. Patients with ISM have aberrant mast cell collections in their bone marrow but have no evidence for another hematologic disease or tissue dysfunction. Mast cells in aspirate smears are usually <5%. Patients with ISM have a comparable life expectancy to general population but can be symptomatic with various mast cell mediator release symptoms. Risk of progression to an advanced variant is less than 5%. SSM is characterized by a high burden of mast cells but no evidence of an overt hematologic disorder or tissue dysfunction. Patients with SSM are thought to have a higher risk of progression to a more advanced category. Both ISM and SSM are referred to as non-advanced SM.

In all subtypes of SM, and in most patients with the disease, neoplastic MCs display a mutation at the D816 position in exon 17 of KIT, which results in ligand-independent activation of KIT kinase activity. Wild-type MCs require KIT activity for their differentiation and survival and, therefore, constitutive activation of KIT through D816V mutation is thought to be a pathogenic driver for SM (Chabot, B. et al., *Nature* 335(6185):88-9 (1988)). Specifically, KIT D816V mutations are found in 90% to 98% of patients with SM, with rare KIT D816Y, D816F, and D816H variants identified (Garcia-Montero, A. C., et al., *Blood* 108(7):2366-72 (2006); Valent, P., *Am J Cancer Res.* 3(2): 159-72 (2013); Verstovsek, S., *Eur J Haematol.* 90(2):89-98 (2013)). Based on these findings, KIT D816V is considered a major therapeutic target in SM (Valent et al, 2017) and several agents targeting this mutation have been studied.

ISM and SSM are characterized by severe symptoms associated with MC mediator release, including pruritus, flushing, GI cramping, diarrhea, anaphylaxis (especially to bee venom), bone pain, and osteoporosis (Gulen, T. et al., *J Intern Med.* 279(3):211-28 (2016)). These symptoms can be severely debilitating, having a negative impact on quality of life (Hermine, O. et al, Masitinib for treatment of severely symptomatic indolent systemic mastocytosis: Additional efficacy analyses from the randomized, placebo-controlled, phase 3 study, *EHA Abstract* 709 (2017); Jennings, S., et al, *J Allergy Clin Immunol.* 2(1):70-76 (2014); Siebenhaar, F. et al, *Allergy* 71(6):869-77 (2016); Van Anrooij, B. et al, Midostaurin (PKC412) in Indolent Systemic Mastocytosis: A Phase 2 Trial. 2016; Pp. Poster Presentation Abstract: P303: European Hematology Association (EHA)).

Patients also are affected frequently by cosmetically debilitating cutaneous mastocytosis (CM), most often urticaria pigmentosa, which affects their quality of life. Abnormal MCs are found in skin and BM biopsies, but MC burden is low and there are no significant cytopenias or other evidence of organ dysfunction due to these infiltrates. Nonspecific treatments have been employed to control MC mediator-related symptoms with varying degrees of efficacy; none impact MC burden in tissues. These treatments include H1 and H2 blockers, proton-pump inhibitors, osteoclast inhibitors, leukotriene inhibitors, corticosteroids, cromolyn sodium, and the anti-IgE antibody omalizumab. Recently, several KIT-targeting tyrosine kinase inhibitors (TKIs) have been studied in patients with ISM and SSM. While some TKI therapies have demonstrated that symptom improvement, and in some cases, reduction in measures of MC burden, can be achieved in patients with ISM and SSM, none of the available agents specifically target the KIT D816V driver mutation in this disease, and to date, no TKI agent, nor any other agent, has been approved to treat ISM and SSM. Therefore, there remains an unmet medical need in patients with moderate-to-severe symptoms who do not adequately respond to existing symptomatic treatments.

As used herein, the "Indolent Systemic Mastocytosis-Symptom Assessment Form" or "ISM-SAF" (ISPOR Europe 2019, Copenhagen Denmark, 2-6 Nov. 2019) is employed for the daily patient reported outcome (PRO) assessment on e.g., an eDiary. The ISM-SAF is a 12-item PRO developed specifically to assess symptoms in patients with ISM and SSM. Though primarily developed for evaluating treatment efficacy hypotheses, the ISM-SAF can also be used to screen participants into (or out of) clinical studies based on a minimum level of sign and symptom severity. Eleven items shown in the table below are graded on an 11-point scale (0 to 10, none to maximum severity), and 1 item (diarrhea) also assesses frequency.

| Item | Symptom |
| --- | --- |
| 1 | Bone pain |
| 2 | Abdominal pain |
| 3 | Nausea |
| 4 | Spots |
| 5 | Itching |
| 6 | Flushing |
| 7 | Fatigue |
| 8 | Dizziness |
| 9 | Brain Fog |
| 10 | Headache |
| 11 | Diarrhea frequency |
| 12 | Diarrhea severity |

The ISM-SAF generates scores for each item, for the domains of skin/Skin Symptom Score (SSS), GI/Gastrointestinal Symptom Score (GSS), and nonspecific symptoms, and a Total Symptom Score (TSS). The TSS is the addition of all symptoms together. In one aspect, TSS is items 1-10 and 12. In one aspect, GSS is items 2-3 and 12. In one aspect, SSS is items 4-6. In one aspect, the patient completes the ISM-SAF daily for 4 weeks beginning at the time of informed consent, during which time BSC medications are optimized and stabilized. Once 4 weeks of data have been collected, the ISM-SAF is completed daily for an additional 2 weeks (14 days) to determine patient eligibility based on the ISM-SAF symptom threshold. Patients meeting the ISM-SAF threshold for eligibility complete the ISM-SAF daily while screening procedures are completed to assess study eligibility. Once all screening procedures are completed, Baseline symptoms are collected for the 14 days immediately preceding study entry. These data will be used as a Baseline TSS.

In one aspect, the patient with ISM or SSM has moderate-to-severe symptoms characterized by a minimum TTS. In one aspect, the patient with ISM or SSM has moderate-to-severe symptoms characterized by a minimum TTS of ≥28 as assessed using the ISM-SAF. In one aspect, the minimum TTS is ≥27, ≥26, ≥25, ≥24, ≥23, ≥22, ≥21, ≥20. In one aspect, the patient with ISM or SSM with moderate-to-severe symptoms has a minimum TSS of ≥28 and ≥1 symptom in skin or GI domains of the ISM-SAF at baseline. In one aspect, baseline is the 14-day period before cycle 1 day 1 (C1D1). In one aspect, the patient is not experiencing an acute flare of symptoms beyond their typical baseline symptoms. In one aspect, the patient has failed to achieve symptom control for 1 or more baseline symptoms, as determined by the investigator, with at least 2 of the following symptomatic therapies administered at optimal (approved) dose and for a minimum of 4 weeks (28 days) before starting the ISM-SAF for determination of eligibility: H1 blockers, H2 blockers, proton-pump inhibitors, leukotriene inhibitors, cromolyn sodium, corticosteroids, or omalizumab. In one aspect, the patient has a baseline serum tryptase of <20 ng/mL. In one aspect, the patient has a baseline serum tryptase of ≥20 ng/mL. In one aspect, the patient has cutaneous mastocytosis (CM). In one aspect, the patient does not have CM. The diagnosis of CM requires the presence of clinical and histopathologic findings of abnormal mast cell infiltration of the dermis with no evidence of systemic mast cell infiltration either in the bone marrow or other extracutaneous organs. CM is further subdivided into 3 different subvariants: urticaria pigmentosa/maculopapular cutaneous mastocytosis (MPCM), diffuse CM, and mastocytoma of the skin.

In one aspect, the patient with ISM or SSM has KIT D816V mutation. The KIT D816V mutation can be detected by a high sensitivity assay such as a droplet digital polymerase chain reaction (ddPCR) assay with a limit of detection (LOD) of 0.022% mutant allele frequency (MAF).

As used herein, an "adverse event" or "AE" is any untoward medical occurrence associated with the use of a drug in humans, whether or not considered drug-related. An AE (also referred to as an adverse experience) can be any unfavorable and unintended sign (e.g., an abnormal laboratory finding), symptom, or disease temporally associated with the use of a drug, without any judgement about causality. An AE can arise from any use of the drug (e.g., off-label use, use in combination with another drug) and from any route of administration, formulation, or dose, including an overdose.

As used herein, the terms "about" and "approximately," when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

As stated above, described herein are novel crystalline forms of Compound (I), pharmaceutically acceptable salts thereof, and solvates of any of the foregoing. In some embodiments, the crystalline forms of Compound (I) are substantially pure. These may be inhibitors of KIT and/or PDGFRα protein kinase and in some embodiments are selective inhibitors of KIT and/or PDGFRα protein kinase. KIT and/or PDGFRα inhibitors are useful in the treatment of disorders and conditions associated with oncogenic KIT and PDGFRA alterations, e.g., mastocytosis, gastrointestinal stromal tumors (GIST), acute myeloid leukemia (AML), melanoma, seminoma, intracranial germ cell tumors, and mediastinal B-cell lymphoma.

Crystalline Form A of Compound (I)

In some embodiments, the present disclosure provides crystalline Form A of Compound (I):

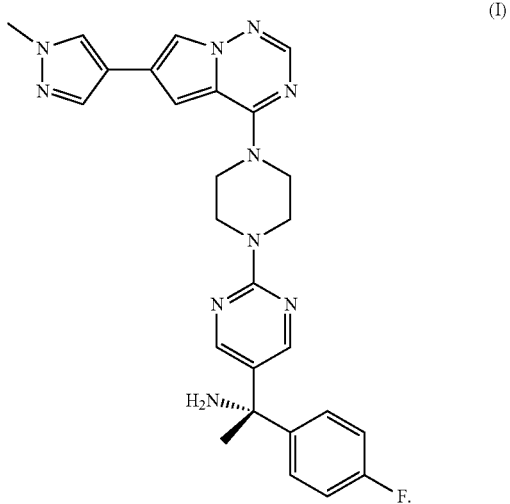 [SMILES: Cn1cc(-c2cc3c(N4CCN(c5ncc([C@@](C)(N)c6ccc(F)cc6)cn5)CC4)ncnn3c2)cn1]

(I)

Among the different crystalline forms of Compound (I) identified, crystalline Form A is more stable at ambient temperature than the other crystalline forms disclosed herein. Moreover, crystalline Form A has been shown to possess better physical and chemical stability properties for formulating as compared to the other crystalline forms identified herein. Crystalline Form A also provides advantages in its ease of isolation. Crystalline Form A has good thermodynamic stability as shown by its DSC.

Figure 2:
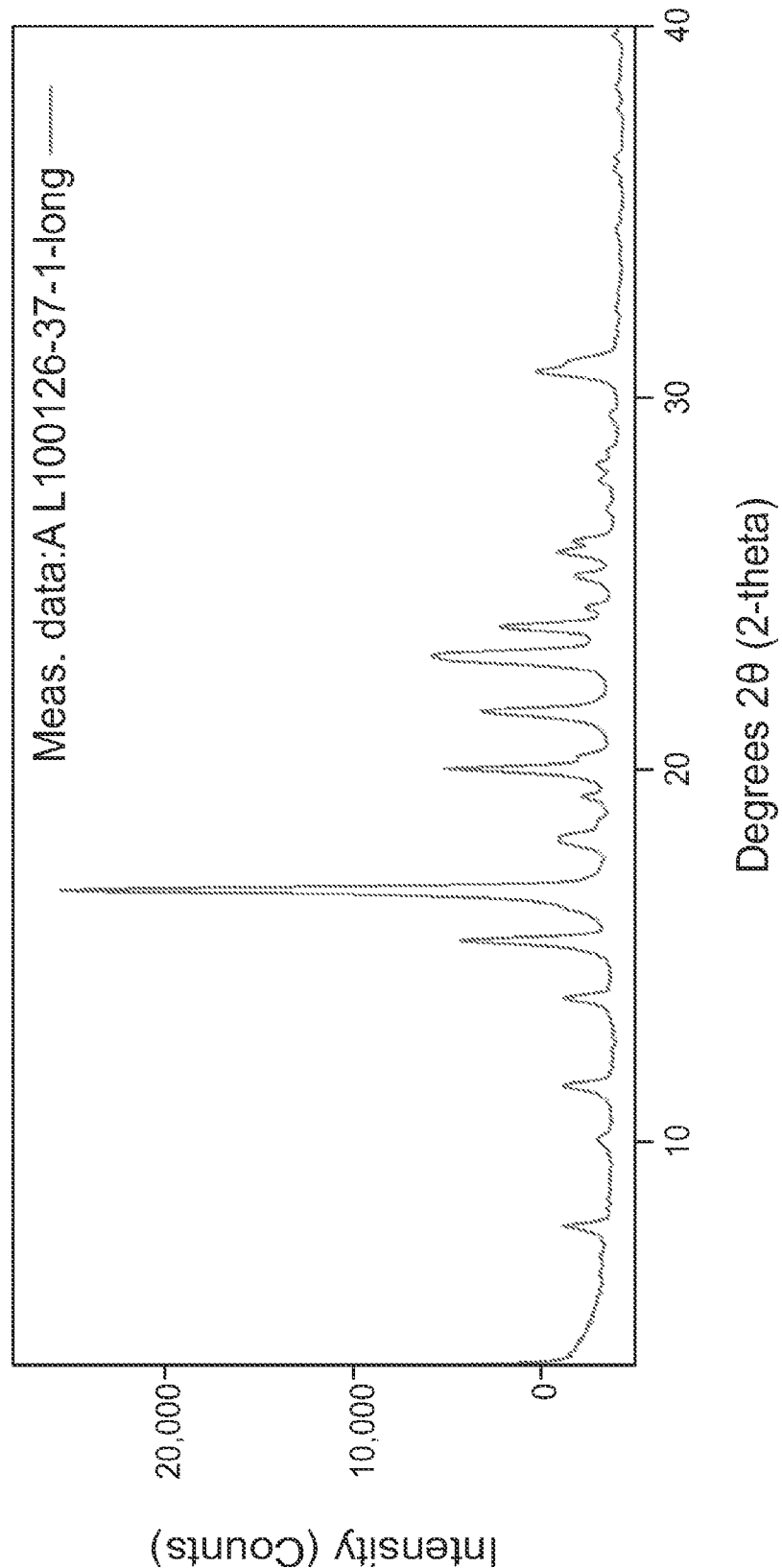
FIG. 2 shows an X-ray powder diffractogram for crystalline Form A of Compound (I), referred to as crystalline Form A herein, showing degrees 2θ (2-theta) on the X-axis and relative intensity on the Y-axis.

FIG. 2 shows an X-ray powder diffractogram of crystalline Form A of Compound (I) at ambient conditions.

Figure 3:
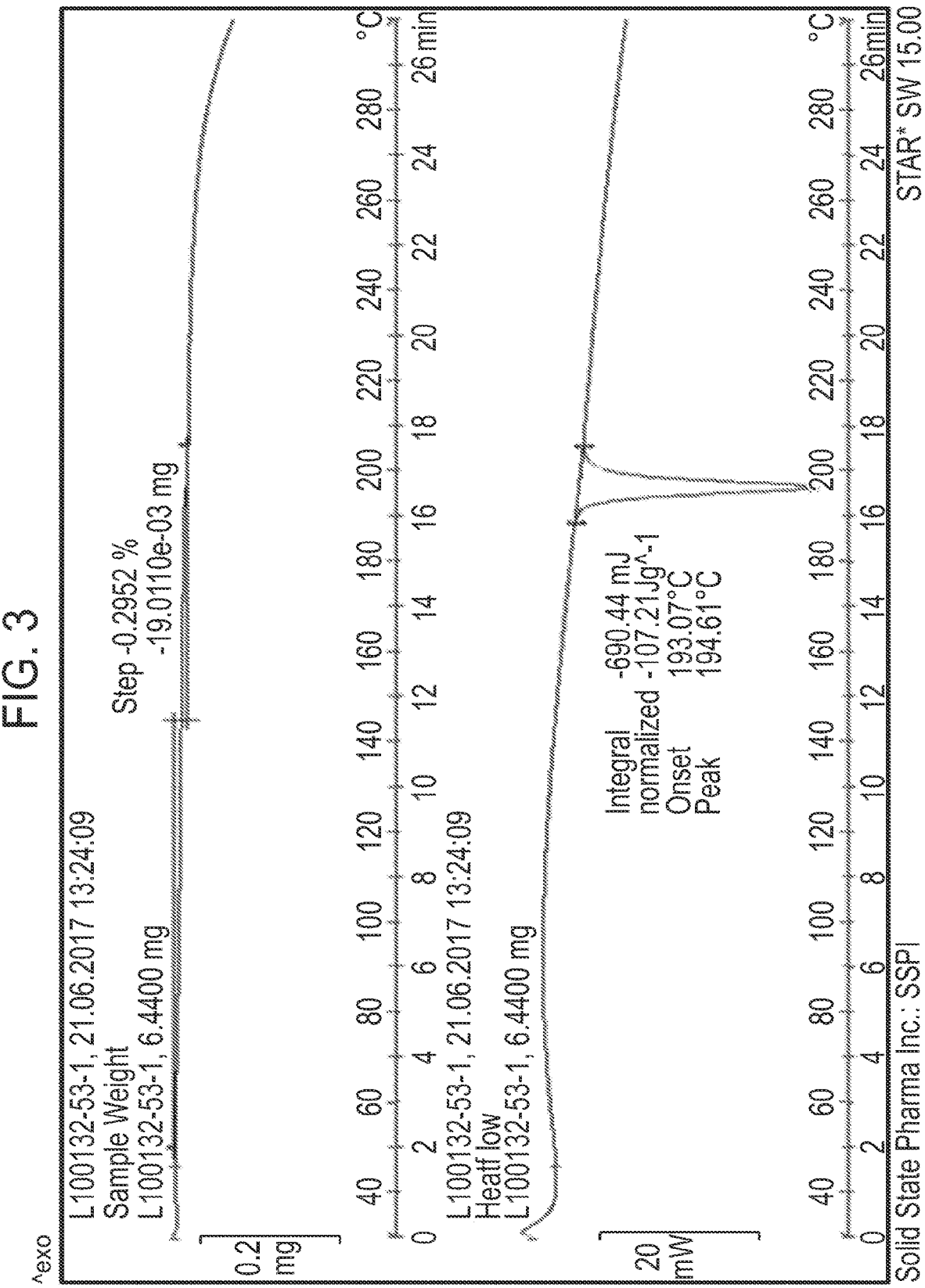
FIG. 3 shows a differential scanning calorimetry (DSC) thermogram for crystalline Form A of Compound (I) and a thermogravimetric analysis (TGA) thermal curve for crystalline Form A of Compound (I) recrystallized from acetone: water.

FIG. 3 shows a DSC thermogram of crystalline Form A of Compound (I). In some embodiments, crystalline Form A of Compound (I) is characterized by a DSC thermogram having an endothermic event with a signal at a temperature ranging from 194° C. to 195° C. In some embodiments, crystalline Form A of Compound (I) is characterized by DSC thermogram having an endothermic event with an onset temperature of 193° C. In some embodiments, crystalline Form A of Compound (I) is characterized by DSC thermogram having an endothermic event with an onset temperature of 190° C., 191° C., or 192° C.

In some embodiments, crystalline Form A of Compound (I) is characterized by a DSC thermogram substantially similar to that in FIG. 3.

FIG. 3 also shows a TGA thermal curve for crystalline Form A of Compound (I) recrystallized from a mixture of acetone and water. For crystalline Form A of Compound (I), demonstrated mass loss by TGA varies based on recrystallization conditions.

In some embodiments, crystalline Form A of Compound (I) is a free-flowing, crystalline white to off-white to yellow solid. In some embodiments, crystalline Form A of Compound (I) is anhydrous polymorph. In some embodiments, the water content of crystalline Form A of Compound (I) is below 1.0% water. In some embodiments, the water content of crystalline Form A of Compound (I) is not more than 0.04%. In some embodiments, water content levels are <0.01%-0.07%. In some embodiments, crystalline Form A of Compound (I) appear to be needles and/or sheet- or plate-like solids.

In some embodiments, crystalline Form A of Compound (I) is characterized by a weight change of 0.42% in a dynamic vapor sorption (DVS) experiment, while varying the relative humidity from 2-95% RH at 25° C.

In some embodiments, crystalline Form A of Compound (I) is characterized by a weight change of 0.29% in a dynamic vapor sorption (DVS) experiment, while varying the relative humidity from 2-95% RH at 40° C.

In some embodiments, crystalline Form A of Compound (I) is characterized by a weight change of 0.20% in a dynamic vapor sorption (DVS) experiment, while varying the relative humidity from 70-95% RH at 40° C.

In some embodiments, crystalline Form A of Compound (I) is non-hygroscopic as determined by dynamic vapor sorption (DVS) analysis. In some embodiments, crystalline Form A of Compound (I) uptakes up to 0.44% moisture by weight when exposed to 40° C. and up to 95% relative humidity.

In some embodiments, crystalline Form A of Compound (I) is characterized by solubility of 0.03 mg/mL in fasted state simulated intestinal fluid (FaSSIF). In some embodiments, crystalline Form A of Compound (I) is characterized by solubility of 2.11 mg/mL in fasted state simulated gastric fluid.

In some embodiments, crystalline Form A of Compound (I) is characterized by solubility of 0.03 mg/mL in fasted state simulated intestinal fluid (FaSSIF) at 37° C. In some embodiments, crystalline Form A of Compound (I) is characterized by solubility of 2.11 mg/mL in fasted state simulated gastric fluid at 37° C.

In some embodiments, crystalline Form A of Compound (I) has a particle size distribution (PSD), wherein D10 is not less than (NLT) 1 μm, D50 is 5-105 μm, e.g., in some embodiments, D50 is 8-80 μm; and D90 is not more than (NMT) 500 μm, e.g., in some embodiments, D90 is NMT 300 μm. As used herein, D10 is the diameter at which 10% of the sample's mass is not less than 1 μm. As used herein, D50 is the mass-median-diameter (MMD). As used herein, the MMD is the average particle diameter by mass. In some embodiments, the average particle diameter by mass (i.e., D50 or MMD) is 5-105 μm. As used herein, D90 is the diameter at which 90% of the sample's mass is not more than 500 μm. In some embodiments, the PSD is NLT 1 μm (D10) and NMT 500 μm (D90). Particle size distribution (PSD) may be analyzed using a laser diffraction system, e.g., Malvern Mastersizer 3000 equipped with a wet dispersion unit. The dispersant is 0.5% Span 85 in hexanes and the sample is 125 mg crystalline Form A of Compound (I) in 50 mL 0.5% Span 85 in hexanes.

In some embodiments, particle size and/or particle size distribution has an effect on tablet dissolution.

In some embodiments, crystalline Form A of Compound (I) is in substantially pure form. In some embodiments, crystalline Form A of Compound (I) is characterized by an X-ray powder diffractogram generated by an X-ray powder diffraction analysis with an incident beam of Cu Kα radiation. In some embodiments, crystalline Form A of Compound (I) is characterized by an X-ray powder diffractogram generated by an X-ray powder diffraction analysis with an incident beam of Cu Kα radiation with signals substantially similar to those recited in Table 1.

TABLE 1

| 2-theta (deg) |
| --- |
| 7.69 |
| 10.07 |
| 11.51 |
| 13.82 |
| 15.36 |
| 16.74 |
| 18.05 |
| 19.21 |
| 19.99 |
| 20.31 |
| 21.58 |
| 22.90 |
| 23.12 |
| 23.86 |
| 24.41 |
| 25.18 |
| 25.85 |
| 26.14 |
| 27.04 |
| 27.76 |
| 28.20 |
| 28.55 |
| 29.50 |
| 30.71 |
| 30.96 |
| 34.49 |
| 36.15 |
| 36.46 |
| 37.70 |
| 38.36 |
| 39.65 |

In some embodiments, crystalline Form A of Compound (I) is characterized by an X-ray powder diffractogram having a signal at 11.5±0.2 degrees two-theta. In some embodiments, crystalline Form A of Compound (I) is characterized by an X-ray powder diffractogram having a signal at 15.4±0.2 degrees two-theta. In some embodiments, crystalline Form A of Compound (I) is characterized by an X-ray powder diffractogram having a signal at 16.7±0.2 degrees two-theta. In some embodiments, crystalline Form A of Compound (I) is characterized by an X-ray powder diffractogram having a signal at 18.1±0.2 degrees two-theta. In some embodiments, crystalline Form A of Compound (I) is characterized by an X-ray powder diffractogram having a signal at 20.0±0.2 degrees two-theta. In some embodiments, crystalline Form A of Compound (I) is characterized by an X-ray powder diffractogram having a signal at 21.6±0.2 degrees two-theta. In some embodiments, crystalline Form A of Compound (I) is characterized by an X-ray powder diffractogram having a signal at 23.1±0.2 degrees two-theta. In some embodiments, crystalline Form A of Compound (I) is characterized by an X-ray powder diffractogram having a signal at 23.9±0.2 degrees two-theta. In some embodiments, crystalline Form A of Compound (I) is characterized by an X-ray powder diffractogram having a signal at 25.9±0.2 degrees two-theta. In some embodiments, crystalline Form A of Compound (I) is characterized by an X-ray powder diffractogram having a signal at 30.7±0.2 degrees two-theta. In some embodiments, crystalline Form A of Compound (I) is characterized by an X-ray powder diffractogram having a signal at two-theta values of 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2. In some embodiments, crystalline Form A of Compound (I) is characterized by an X-ray powder diffractogram having a signal at at least eight two-theta values chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2. In some embodiments, crystalline Form A of Compound (I) is characterized by an X-ray powder diffractogram having a signal at at least seven two-theta values chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2. In some embodiments, crystalline Form A of Compound (I) is characterized by an X-ray powder diffractogram having a signal at at least six two-theta values chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2. In some embodiments, crystalline Form A of Compound (I) is characterized by an X-ray powder diffractogram having a signal at at least five two-theta values chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2. In some embodiments, crystalline Form A of Compound (I) is characterized by an X-ray powder diffractogram having a signal at at least four two-theta values chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2. In some embodiments, crystalline Form A of Compound (I) is characterized by an X-ray powder diffractogram having a signal at at least three two-theta values chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2. In some embodiments, crystalline Form A of Compound (I) is characterized by an X-ray powder diffractogram having a signal at at least two two-theta values chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2. In some embodiments, crystalline Form A of Compound (I) is characterized by an X-ray powder diffractogram having a signal at at least one two-theta value chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2.

In some embodiments, crystalline Form A of Compound (I) is characterized by an X-ray powder diffractogram having a signal at at least three two-theta values chosen from 11.5±0.2, 15.4±0.2, 16.7±0.2, 20.0±0.2, and 21.6±0.2. In some embodiments, crystalline Form A of Compound (I) is characterized by an X-ray powder diffractogram having a signal at at least two two-theta values chosen from 11.5±0.2, 15.4±0.2, 16.7±0.2, 20.0±0.2, and 21.6±0.2. In some embodiments, crystalline Form A of Compound (I) is characterized by an X-ray powder diffractogram having a signal at at least one two-theta value chosen from 11.5±0.2, 15.4±0.2, 16.7±0.2, 20.0±0.2, and 21.6±0.2. In some embodiments, crystalline Form A of Compound (I) is characterized by an X-ray powder diffractogram having a signal at two-theta values of 11.5±0.2, 15.4±0.2, 16.7±0.2, 20.0±0.2, and 21.6±0.2.

In some embodiments, crystalline Form A of Compound (I) is characterized by an X-ray powder diffractogram substantially similar to that in FIG. 2.

In some embodiments, crystalline Form A of Compound (I) is characterized by a $^{13}$C NMR (CDCl$_3$, 100 MHz) pattern having a signal at the following δ (expressed as ppm): 32.1, 39.2, 43.5, 45.5, 55.6, 101.3, 115.2, 115.5, 116.0, 116.5, 117.9, 127.0, 127.7, 131.1, 137.1, 144.4, 146.7, 154.6, 156.3, 160.4, and 161.7.

In some embodiments, the present disclosure provides a process for preparing crystalline Form A of Compound (I).

In some embodiments, the process for preparing crystalline Form A of Compound (I) is a recrystallization process. In some embodiments, the recrystallization process removes impurities. In some embodiments, the recrystallization process removes residual N,N-diisopropylethylamine. In some embodiments, the recrystallization process comprises acetone and water. In some embodiments, the present disclosure provides crystalline Form A of Compound (I) prepared by a process comprising: dissolving Compound (I) in acetone and water to obtain a suspension; heating the suspension to obtain a solution; and cooling the solution, such as by lowering the temperature.

In some embodiments, the ratio of acetone to water is 85:15.

In some embodiments, the suspension is heated to a temperature ranging from 40° C. to 50° C.

In some embodiments, the process further comprises stirring the heated suspension. In some embodiments, the process further comprises stirring the heated suspension at a temperature ranging from 40° C. to 50° C. In some embodiments, the heated suspension is stirred. In some embodiments, the heated suspension is stirred for fifteen minutes. In some embodiments, the heated suspension is stirred at a temperature ranging from 40° C. to 50° C. In some embodiments, the heated suspension is stirred for fifteen minutes at a temperature ranging from 40° C. to 50° C.

In some embodiments, the process further comprises polish filtering the stirred suspension. In some embodiments, the process further comprises polish filtering the stirred suspension at a temperature ranging from 40° C. to 50° C.

In some embodiments, the process further comprises atmospherically distilling the polish filtered suspension. In some embodiments, the process further comprises atmospherically distilling the polish filtered suspension at a temperature ranging from 55° C. to 65° C.

In some embodiments, cooling the solution comprises lowering the temperature. In some embodiments, cooling the solution comprises lowering the temperature to a temperature ranging from 45° C. to 55° C. In some embodiments, cooling the solution comprises lowering the temperature over fifteen minutes. In some embodiments, cooling the solution comprises lowering the temperature to a temperature ranging from 45° C. to 55° C. over fifteen minutes.

In some embodiments, the present disclosure provides a process for preparing crystalline Form A of Compound (I) and also provides crystalline Form A of Compound (I) prepared by a process comprising: slurrying crystalline Form C of Compound (I) in acetone at an elevated temperature. In some embodiments, the elevated temperature is at least 30° C.

In some embodiments, the present disclosure provides a process for preparing crystalline Form A of Compound (I) and also provides crystalline Form A of Compound (I) prepared by a process comprising: heating crystalline Form O of Compound (I) to an elevated temperature; and slurrying in at least one solvent. In some embodiments, the elevated temperature is 186° C. In some embodiments, the at least one solvent is acetone. In some embodiments, the at least one solvent comprises acetone and water.

In some embodiments, the present disclosure provides a process for preparing crystalline Form A of Compound (I) and also provides crystalline Form A of Compound (I) prepared by a process comprising: slurrying crystalline Form B of Compound (I) in at least one solvent at an elevated temperature. In some embodiments, the at least one solvent is acetone. In some embodiments, the elevated temperature is ranging from 25° C. to 50° C.

In some embodiments, any of the above processes for preparing crystalline Form A of Compound (I) may further comprise purifying crystalline Form A by dissolving crystalline Form A in a mixture of acetone and water and/or by slurring in isopropanol. In some embodiments, the isopropanol slurry is obtained by taking the crystalline solid up in isopropanol and heating and then cooling the resulting mixture. In some embodiments, the crystalline solid is isolated by filtration, washed with isopropanol, and dried.

In some embodiments, the present disclosure provides a process for preparing a substantially pure crystalline Form A of Compound (I).

Crystalline Form B of Compound (I)

In some embodiments, the present disclosure provides crystalline Form B of Compound (I):

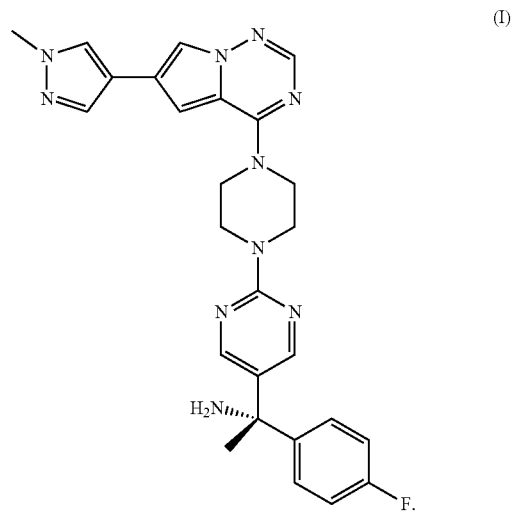 [SMILES: Cn1cc(-c2cc3c(N4CCN(c5ncc([C@@](C)(N)c6ccc(F)cc6)cn5)CC4)ncnn3c2)cn1]

(I)

Figure 4:
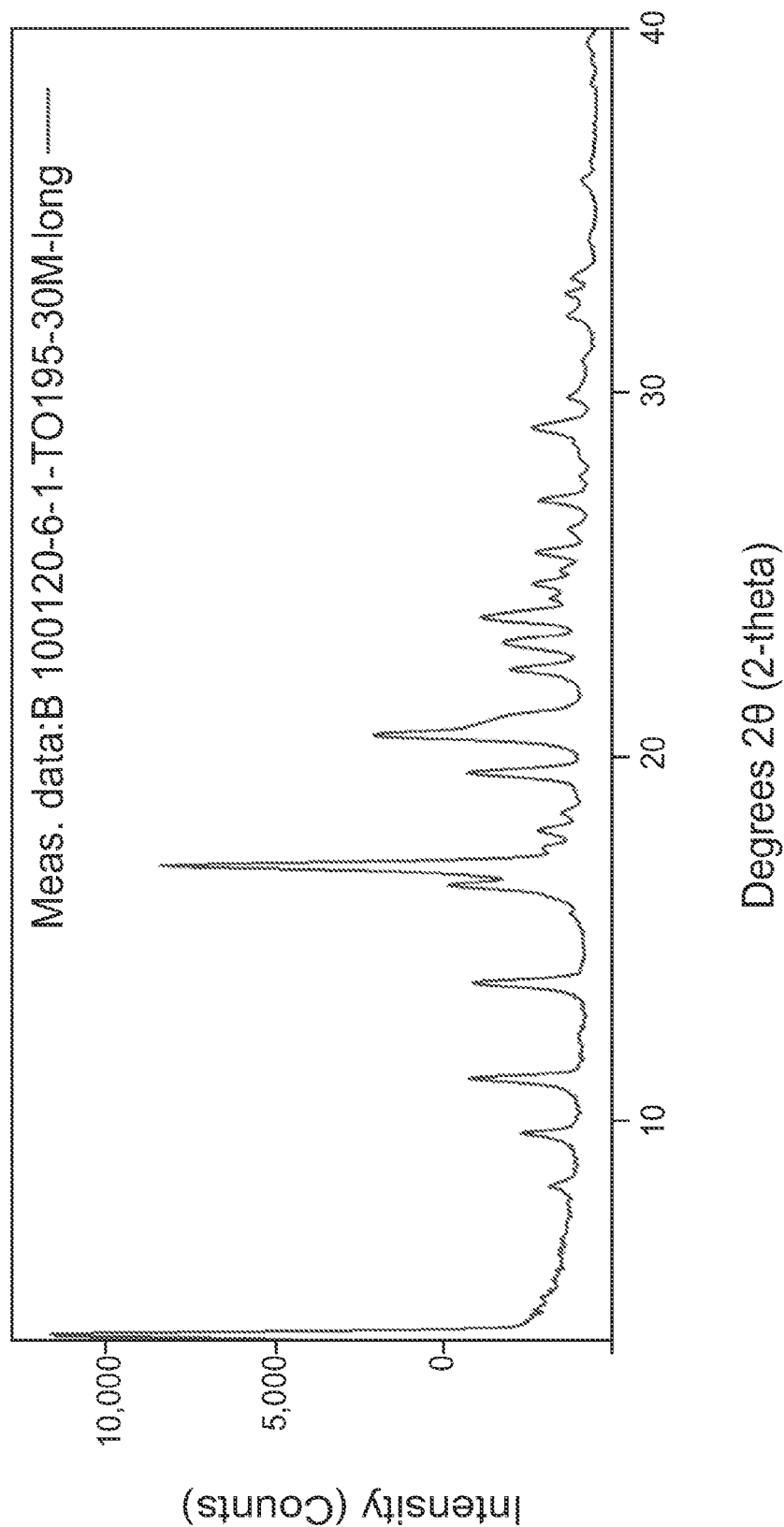
FIG. 4 shows an X-ray powder diffractogram for crystalline Form B of Compound (I), referred to as crystalline Form B herein, showing degrees 2θ (2-theta) on the X-axis and relative intensity on the Y-axis.

FIG. 4 shows an X-ray powder diffractogram for crystalline Form B of Compound (I) at ambient conditions.

Figure 5:
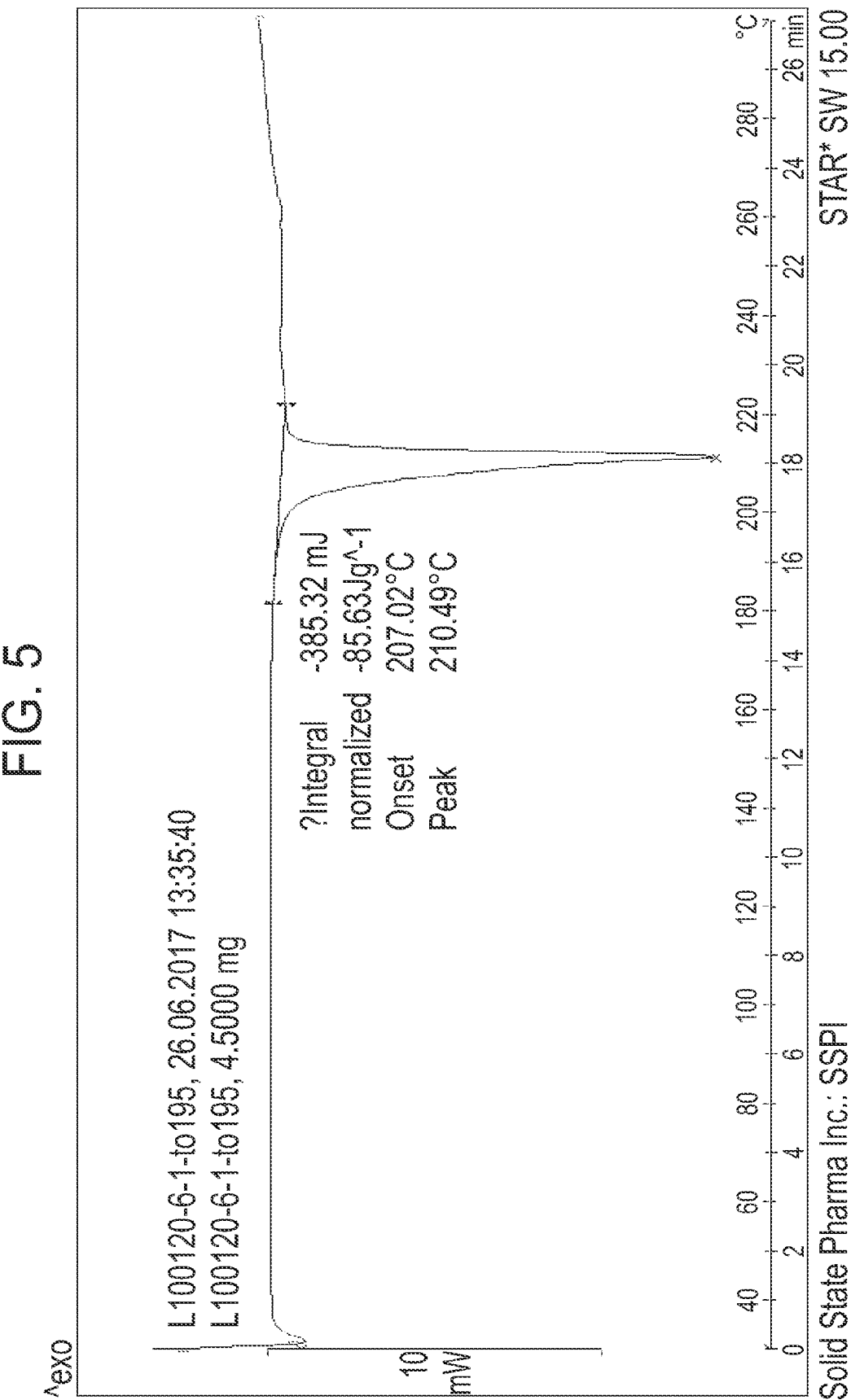
FIG. 5 shows a DSC thermogram for the crystalline Form B of Compound (I).

FIG. 5 shows a DSC thermogram for crystalline Form B of Compound (I). In some embodiments, crystalline Form B of Compound (I) is characterized by a DSC thermogram having an endothermic event with a signal at a temperature ranging from 210° C. to 211° C. In some embodiments, crystalline Form B of Compound (I) is characterized by a DSC thermogram having an endothermic event with an onset temperature of 207° C. In some embodiments, crystalline Form B of Compound (I) is characterized by a DSC thermogram substantially similar to that in FIG. 5.

In some embodiments, crystalline Form B of Compound (I) is in substantially pure form. In some embodiments, crystalline Form B of Compound (I) is characterized by an X-ray powder diffractogram generated by an X-ray powder diffraction analysis with an incident beam of Cu Kα radiation. In some embodiments, crystalline Form B of Compound (I) is characterized by an X-ray powder diffractogram generated by an X-ray powder diffraction analysis with an incident beam of Cu Kα radiation with signals substantially similar to those recited in Table 2.

TABLE 2

| 2-theta (deg) |
| --- |
| 4.13 |
| 8.20 |
| 9.66 |
| 11.15 |
| 13.77 |
| 16.43 |
| 16.98 |
| 17.97 |
| 18.44 |
| 19.55 |
| 20.55 |
| 21.03 |
| 22.40 |
| 23.13 |
| 23.82 |
| 24.32 |
| 24.73 |
| 25.09 |
| 25.61 |
| 26.27 |
| 27.02 |
| 29.01 |
| 29.80 |
| 30.89 |
| 32.10 |
| 32.72 |
| 33.17 |
| 35.81 |
| 39.60 |

In some embodiments, crystalline Form B of Compound (I) is characterized by an X-ray powder diffractogram having a signal at 4.1±0.2 degrees two-theta. In some embodiments, crystalline Form B of Compound (I) is characterized by an X-ray powder diffractogram having a signal at 9.7±0.2 degrees two-theta. In some embodiments, crystalline Form B of Compound (I) is characterized by an X-ray powder diffractogram having a signal at 11.2±0.2 degrees two-theta. In some embodiments, crystalline Form B of Compound (I) is characterized by an X-ray powder diffractogram having a signal at 13.8±0.2 degrees two-theta. In some embodiments, crystalline Form B of Compound (I) is characterized by an X-ray powder diffractogram having a signal at 16.4±0.2 degrees two-theta. In some embodiments, crystalline Form B of Compound (I) is characterized by an X-ray powder diffractogram having a signal at 17.0±0.2 degrees two-theta. In some embodiments, crystalline Form B of Compound (I) is characterized by an X-ray powder diffractogram having a signal at 19.6±0.2 degrees two-theta. In some embodiments, crystalline Form B of Compound (I) is characterized by an X-ray powder diffractogram having a signal at 20.6±0.2 degrees two-theta. In some embodiments, crystalline Form B of Compound (I) is characterized by an X-ray powder diffractogram having a signal at 21.0±0.2 degrees two-theta. In some embodiments, crystalline Form B of Compound (I) is characterized by an X-ray powder diffractogram having a signal at 22.4±0.2 degrees two-theta. In some embodiments, crystalline Form B of Compound (I) is characterized by an X-ray powder diffractogram having a signal at 23.1±0.2 degrees two-theta. In some embodiments, crystalline Form B of Compound (I) is characterized by an X-ray powder diffractogram having a signal at 23.8±0.2 degrees two-theta. In some embodiments, crystalline Form B of Compound (I) is characterized by an X-ray powder diffractogram having a signal at 29.0±0.2 degrees two-theta.

In some embodiments, crystalline Form B of Compound (I) is characterized by an X-ray powder diffractogram having a signal at two-theta values of 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2. In some embodiments, crystalline Form B of Compound (I) is characterized by an X-ray powder diffractogram having a signal at at least eight two-theta values chosen from 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2. In some embodiments, crystalline Form B of Compound (I) is characterized by an X-ray powder diffractogram having a signal at at least seven two-theta values chosen from 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2. In some embodiments, crystalline Form B of Compound (I) is characterized by an X-ray powder diffractogram having a signal at at least six two-theta values chosen from 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2. In some embodiments, crystalline Form B of Compound (I) is characterized by an X-ray powder diffractogram having a signal at at least five two-theta values chosen from 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2. In some embodiments, crystalline Form B of Compound (I) is characterized by an X-ray powder diffractogram having a signal at at least four two-theta values chosen from 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2. In some embodiments, crystalline Form B of Compound (I) is characterized by an X-ray powder diffractogram having a signal at at least three two-theta values chosen from 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2. In some embodiments, crystalline Form B of Compound (I) is characterized by an X-ray powder diffractogram having a signal at at least two two-theta values chosen from 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2. In some embodiments, crystalline Form B of Compound (I) is characterized by an X-ray powder diffractogram having a signal at at least one two-theta value chosen from 4.1±0.2, 9.7±0.2, 11.2±0.2, 13.8±0.2, 16.4±0.2, 17.0±0.2, 19.6±0.2, 20.6±0.2, 21.0±0.2, 22.4±0.2, 23.1±0.2, 23.8±0.2, and 29.0±0.2.

In some embodiments, crystalline Form B of Compound (I) is characterized by an X-ray powder diffractogram having a signal at at least three two-theta values chosen from 4.1±0.2, 16.4±0.2, 17.0±0.2, 19.6±0.2, and 20.6±0.2. In some embodiments, crystalline Form B of Compound (I) is characterized by an X-ray powder diffractogram having a signal at at least two two-theta values chosen from 4.1±0.2, 16.4±0.2, 17.0±0.2, 19.6±0.2, and 20.6±0.2. In some embodiments, crystalline Form B of Compound (I) is characterized by an X-ray powder diffractogram having a signal at at least one two-theta value chosen from 4.1±0.2, 16.4±0.2, 17.0±0.2, 19.6±0.2, and 20.6±0.2. In some embodiments, crystalline Form B of Compound (I) is characterized by an X-ray powder diffractogram having a signal at two-theta values of 4.1±0.2, 16.4±0.2, 17.0±0.2, 19.6±0.2, and 20.6±0.2.

In some embodiments, crystalline Form B of Compound (I) is characterized by an X-ray powder diffractogram substantially similar to that in FIG. 4.

In some embodiments, crystalline Form B of Compound (I) is characterized by a $^{13}$C NMR (CDCl$_3$, 100 MHz) pattern having a signal at at least one δ value (expressed as ppm) chosen from 32.1, 39.2, 43.5, 45.5, 55.6, 101.3, 115.2, 115.5, 116.0, 116.5, 117.9, 127.0, 127.7, 131.1, 137.1, 144.4, 146.7, 154.6, 156.3, 160.4, and 161.7.

In some embodiments, the present disclosure provides a process for preparing crystalline Form B of Compound (I). In some embodiments, the present disclosure provides crystalline Form B of Compound (I) prepared by a process comprising: heating Compound (I) for a time at an elevated temperature; and cooling to room temperature. In some embodiments, the time is ten minutes. In some embodiments, the elevated temperature is 195° C.

In some embodiments, the process further comprises isolating crystalline Form B of Compound (I) by filtration.

In some embodiments, the present disclosure provides a process for preparing crystalline Form B of Compound (I) and also provides crystalline Form B of Compound (I) prepared by a process comprising: heating crystalline Form A of Compound (I) for a time at an elevated temperature; and cooling to room temperature. In some embodiments, the time is thirty minutes. In some embodiments, the elevated temperature is 195° C.

In some embodiments, the present disclosure provides a process for preparing crystalline Form B of Compound (I) and also provides crystalline Form B of Compound (I) prepared by a process comprising: prolonged heating of crystalline Form A of Compound (I) at 195° C.

In some embodiments, the process further comprises isolating crystalline Form B of Compound (I) by filtration.

Crystalline Form C of Compound (I)

In some embodiments, the present disclosure provides crystalline Form C of Compound (I):

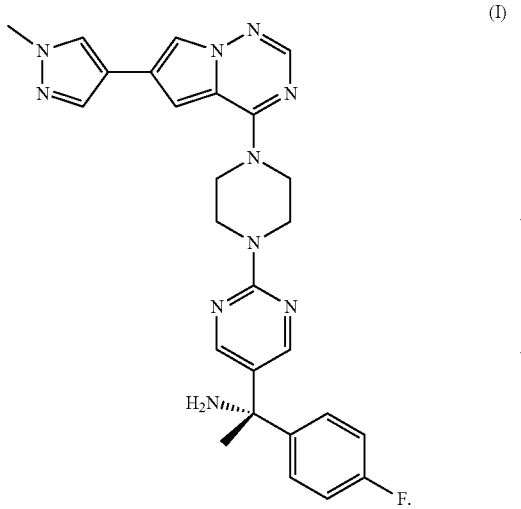

(I)

Crystalline Form C is a hydrate of Compound (I).

Figure 6:
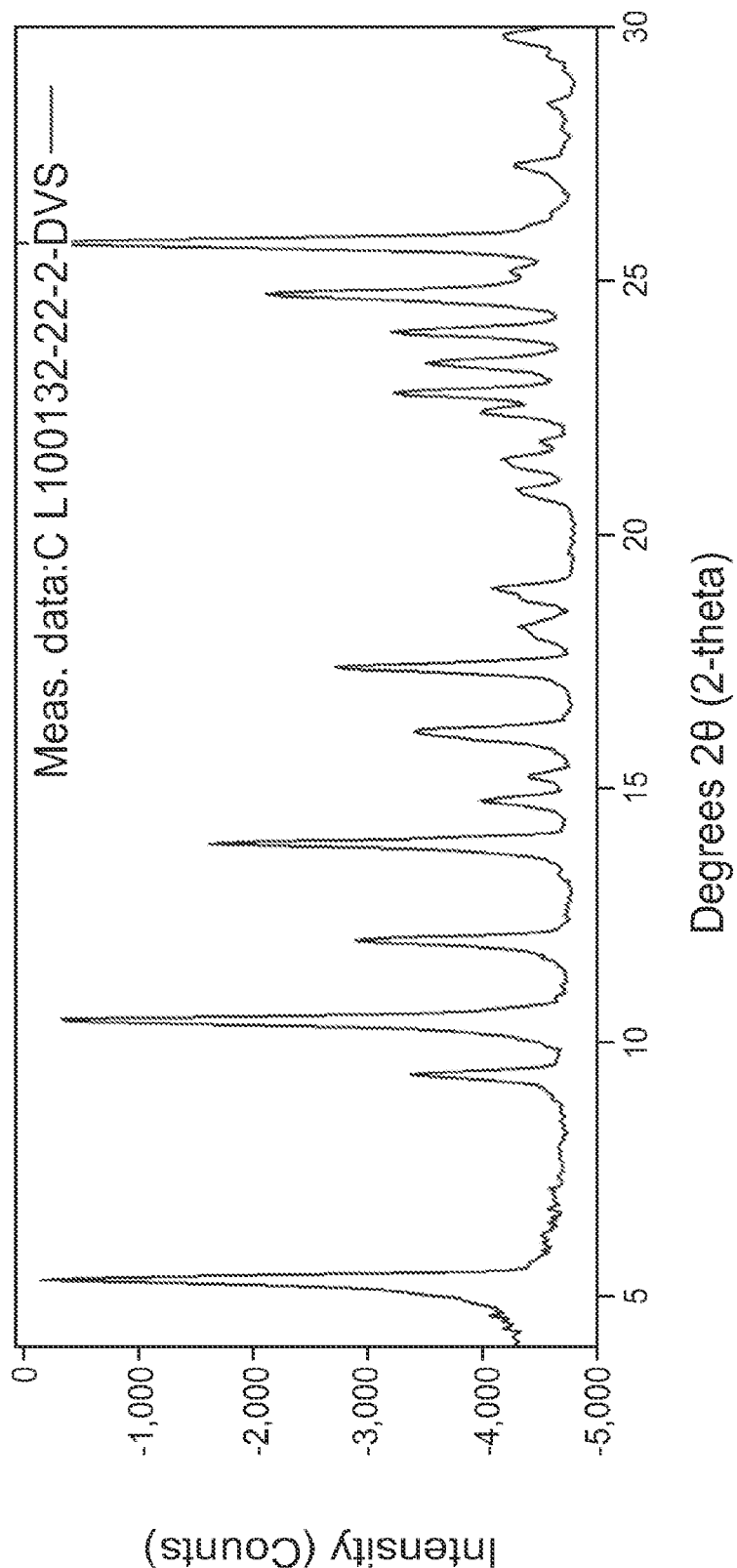
FIG. 6 shows an X-ray powder diffractogram for crystalline Form C of Compound (I), referred to as crystalline Form C herein, showing degrees 2θ (2-theta) on the X-axis and relative intensity on the Y-axis.

FIG. 6 shows an X-ray powder diffractogram for crystalline Form C of Compound (I) at ambient conditions.

In some embodiments, crystalline Form C of Compound (I) are rod-like crystals. In some embodiments, crystalline Form C of Compound (I) is characterized by irregular morphology.

In some embodiments, crystalline Form C of Compound (I) is characterized by a weight change of 2.90% in a dynamic vapor sorption experiment, while varying the relative humidity from 2-95% RH at 25° C. In some embodiments, crystalline Form C of Compound (I) is characterized by a weight change of 1.76% in a dynamic vapor sorption experiment, while varying the relative humidity from 2-10% RH at 25° C.

In some embodiments, crystalline Form C of Compound (I) is characterized by a weight change of 2.99% in a dynamic vapor sorption experiment, while varying the relative humidity from 2-95% RH at 40° C. In some embodiments, crystalline Form C of Compound (I) is characterized by a weight change of 1.93% in a dynamic vapor sorption experiment, while varying the relative humidity from 2-10% RH at 40° C.

In some embodiments, crystalline Form C of Compound (I) is characterized by solubility of 0.03 mg/mL in fasted state simulated intestinal fluid. In some embodiments, crystalline Form C of Compound (I) is characterized by solubility of 2.72 mg/mL in fasted state simulated gastric fluid. In some embodiments, crystalline Form C of Compound (I) is characterized by solubility of 0.03 mg/mL in fasted state simulated intestinal fluid at 37° C. In some embodiments, crystalline Form C of Compound (I) is characterized by solubility of 2.72 mg/mL in fasted state simulated gastric fluid at 37° C.

In some embodiments, crystalline Form C of Compound (I) is in substantially pure form. In some embodiments, crystalline Form C of Compound (I) is characterized by an X-ray powder diffractogram generated by an X-ray powder diffraction analysis with an incident beam of Cu Kα radiation. In some embodiments, crystalline Form C of Compound (I) is characterized by an X-ray powder diffractogram generated by an X-ray powder diffraction analysis with an incident beam of Cu Kα radiation with signals substantially similar to those recited in Table 3.

TABLE 3

| 2-theta (deg) |
| --- |
| 5.33 |
| 9.35 |
| 10.44 |
| 11.97 |
| 13.91 |
| 14.75 |
| 15.24 |
| 16.11 |
| 17.38 |
| 18.16 |
| 18.94 |
| 20.83 |
| 21.42 |
| 21.81 |
| 22.41 |
| 22.78 |
| 23.38 |
| 23.98 |
| 24.75 |
| 25.19 |
| 25.77 |
| 27.30 |
| 28.49 |
| 29.83 |

In some embodiments, crystalline Form C of Compound (I) is characterized by an X-ray powder diffractogram having a signal at 5.3±0.2 degrees two-theta. In some embodiments, crystalline Form C of Compound (I) is characterized by an X-ray powder diffractogram having a signal at 9.4±0.2 degrees two-theta. In some embodiments, crystalline Form C of Compound (I) is characterized by an X-ray powder diffractogram having a signal at 10.4±0.2 degrees two-theta. In some embodiments, crystalline Form C of Compound (I) is characterized by an X-ray powder diffractogram having a signal at 12.0±0.2 degrees two-theta. In some embodiments, crystalline Form C of Compound (I) is characterized by an X-ray powder diffractogram having a signal at 13.9±0.2 degrees two-theta. In some embodiments, crystalline Form C of Compound (I) is characterized by an X-ray powder diffractogram having a signal at 16.1±0.2 degrees two-theta. In some embodiments, crystalline Form C of Compound (I) is characterized by an X-ray powder diffractogram having a signal at 17.4±0.2 degrees two-theta. In some embodiments, crystalline Form C of Compound (I) is characterized by an X-ray powder diffractogram having a signal at 22.8±0.2 degrees two-theta. In some embodiments, crystalline Form C of Compound (I) is characterized by an X-ray powder diffractogram having a signal at 24.0±0.2 degrees two-theta. In some embodiments, crystalline Form C of Compound (I) is characterized by an X-ray powder diffractogram having a signal at 24.8±0.2 degrees two-theta. In some embodiments, crystalline Form C of Compound (I) is characterized by an X-ray powder diffractogram having a signal at 25.8±0.2 degrees two-theta.

In some embodiments, crystalline Form C of Compound (I) is characterized by an X-ray powder diffractogram having a signal at two-theta values of 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2. In some embodiments, crystalline Form C of Compound (I) is characterized by an X-ray powder diffractogram having a signal at at least eight two-theta values chosen from 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2. In some embodiments, crystalline Form C of Compound (I) is characterized by an X-ray powder diffractogram having a signal at at least seven two-theta values chosen from 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2. In some embodiments, crystalline Form C of Compound (I) is characterized by an X-ray powder diffractogram having a signal at at least six two-theta values chosen from 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2. In some embodiments, crystalline Form C of Compound (I) is characterized by an X-ray powder diffractogram having a signal at at least five two-theta values chosen from 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2. In some embodiments, crystalline Form C of Compound (I) is characterized by an X-ray powder diffractogram having a signal at at least four two-theta values chosen from 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2. In some embodiments, crystalline Form C of Compound (I) is characterized by an X-ray powder diffractogram having a signal at at least three two-theta values chosen from 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2. In some embodiments, crystalline Form C of Compound (I) is characterized by an X-ray powder diffractogram having a signal at at least two two-theta values chosen from 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2. In some embodiments, crystalline Form C of Compound (I) is characterized by an X-ray powder diffractogram having a signal at at least one two-theta value chosen from 5.3±0.2, 9.4±0.2, 10.4±0.2, 12.0±0.2, 13.9±0.2, 16.1±0.2, 17.4±0.2, 22.8±0.2, 24.0±0.2, 24.8±0.2, and 25.8±0.2.

In some embodiments, crystalline Form C of Compound (I) is characterized by an X-ray powder diffractogram having a signal at at least three two-theta values chosen from 5.3±0.2, 9.4±0.2, 10.4±0.2, 12.0±0.2, and 16.1±0.2. In some embodiments, crystalline Form C of Compound (I) is characterized by an X-ray powder diffractogram having a signal at at least two two-theta values chosen from 5.3±0.2, 9.4±0.2, 10.4±0.2, 12.0±0.2, and 16.1±0.2. In some embodiments, crystalline Form C of Compound (I) is characterized by an X-ray powder diffractogram having a signal at at least one two-theta value chosen from 5.3±0.2, 9.4±0.2, 10.4±0.2, 12.0±0.2, and 16.1±0.2. In some embodiments, crystalline Form C of Compound (I) is characterized by an X-ray powder diffractogram having a signal at two-theta values of 5.3±0.2, 9.4±0.2, 10.4±0.2, 12.0±0.2, and 16.1±0.2.

In some embodiments, crystalline Form C of Compound (I) is characterized by an X-ray powder diffractogram substantially similar to that in FIG. 6.

In some embodiments, crystalline Form C of Compound (I) is characterized by a $^{13}$C NMR (CDCl$_3$, 100 MHz) pattern having a signal at at least one δ value (expressed as ppm) chosen from 32.1, 39.2, 43.5, 45.5, 55.6, 101.3, 115.2, 115.5, 116.0, 116.5, 117.9, 127.0, 127.7, 131.1, 137.1, 144.4, 146.7, 154.6, 156.3, 160.4, and 161.7.

In some embodiments, the present disclosure provides a process for preparing crystalline Form C of Compound (I) and also provides crystalline Form C of Compound (I) prepared by a process comprising: slurrying Compound (I) in methanol or a 1:1 mixture of tetrahydrofuran:water. In some methods, the process further comprises isolating the crystalline Form C of Compound (I) by filtration.

Crystalline Form O of Compound (I)

In some embodiments, the present disclosure provides crystalline Form O of Compound (I):

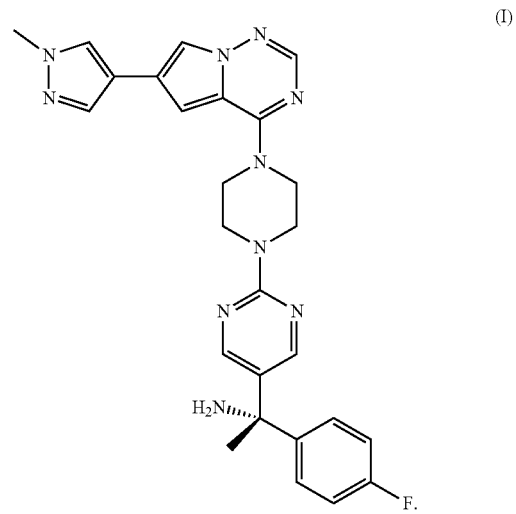 [SMILES: Cn1cc(-c2cc3c(N4CCN(c5ncc([C@@](C)(N)c6ccc(F)cc6)cn5)CC4)ncnn3c2)cn1]

(I)

Figure 7:
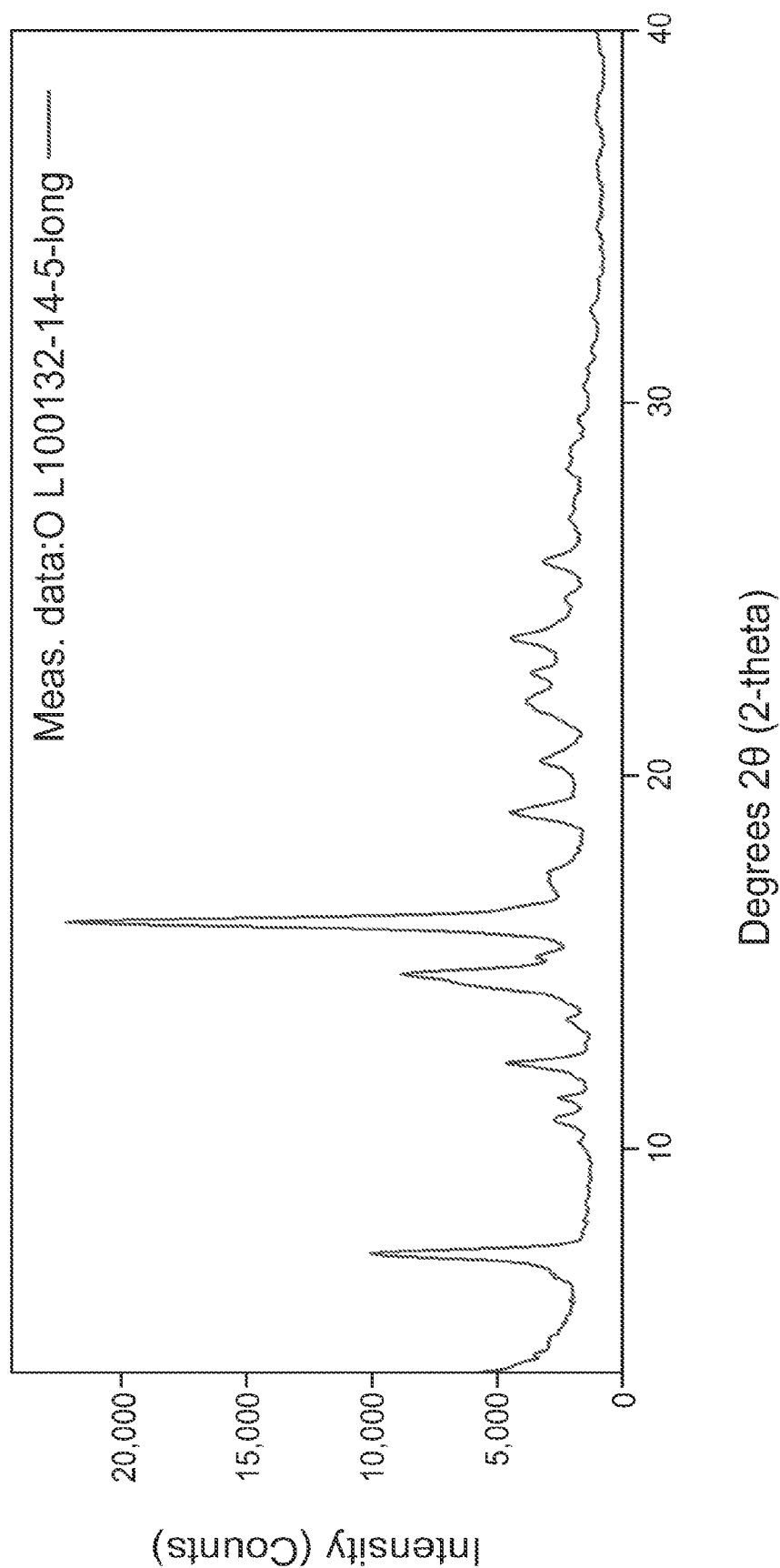
FIG. 7 shows an X-ray powder diffractogram for crystalline Form O of Compound (I), referred to as crystalline Form O herein, showing degrees 2θ (2-theta) on the X-axis and relative intensity on the Y-axis.

FIG. 7 shows an X-ray powder diffractogram for crystalline Form O of Compound (I) at ambient conditions.

In some embodiments, crystalline Form O of Compound (I) is characterized by a DSC thermogram having an endothermic event with an onset temperature of 182° C.

In some embodiments, crystalline Form O of Compound (I) is in substantially pure form. In some embodiments, crystalline Form O of Compound (I) is characterized by an X-ray powder diffractogram generated by an X-ray powder diffraction analysis with an incident beam of Cu Kα radiation. In some embodiments, crystalline Form O of Compound (I) is characterized by an X-ray powder diffractogram generated by an X-ray powder diffraction analysis with an incident beam of Cu Kα radiation with signals substantially similar to those recited in Table 4.

TABLE 4

| 2-theta (deg) |
| --- |
| 7.17 |
| 10.14 |
| 10.78 |
| 11.37 |
| 12.25 |
| 14.48 |
| 14.68 |
| 16.08 |
| 17.34 |
| 18.95 |
| 20.35 |
| 21.86 |
| 22.71 |
| 23.65 |
| 25.70 |
| 26.96 |
| 28.49 |
| 29.59 |
| 30.46 |
| 32.41 |
| 34.77 |
| 36.37 |
| 37.71 |

In some embodiments, crystalline Form O of Compound (I) is characterized by an X-ray powder diffractogram having a signal at 7.2±0.2 degrees two-theta. In some embodiments, crystalline Form O of Compound (I) is characterized by an X-ray powder diffractogram having a signal at 10.8±0.2 degrees two-theta. In some embodiments, crystalline Form O of Compound (I) is characterized by an X-ray powder diffractogram having a signal at 12.3±0.2 degrees two-theta. In some embodiments, crystalline Form O of Compound (I) is characterized by an X-ray powder diffractogram having a signal at 14.5±0.2 degrees two-theta. In some embodiments, crystalline Form O of Compound (I) is characterized by an X-ray powder diffractogram having a signal at 14.7±0.2 degrees two-theta. In some embodiments, crystalline Form O of Compound (I) is characterized by an X-ray powder diffractogram having a signal at 16.1±0.2 degrees two-theta. In some embodiments, crystalline Form O of Compound (I) is characterized by an X-ray powder diffractogram having a signal at 19.0±0.2 degrees two-theta. In some embodiments, crystalline Form O of Compound (I) is characterized by an X-ray powder diffractogram having a signal at 20.4±0.2 degrees two-theta. In some embodiments, crystalline Form O of Compound (I) is characterized by an X-ray powder diffractogram having a signal at 23.7±0.2 degrees two-theta.

In some embodiments, crystalline Form O of Compound (I) is characterized by an X-ray powder diffractogram having a signal at two-theta values of 7.2±0.2, 10.8±0.2, 12.3±0.2, 14.5±0.2, 14.7±0.2, 16.1±0.2, 19.0±0.2, 20.4±0.2, and 23.7±0.2. In some embodiments, crystalline Form O of Compound (I) is characterized by an X-ray powder diffractogram having a signal at at least eight two-theta values chosen from 7.2±0.2, 10.8±0.2, 12.3±0.2, 14.5±0.2, 14.7±0.2, 16.1±0.2, 19.0±0.2, 20.4±0.2, and 23.7±0.2. In some embodiments, crystalline Form O of Compound (I) is characterized by an X-ray powder diffractogram having a signal at at least seven two-theta values chosen from 7.2±0.2, 10.8±0.2, 12.3±0.2, 14.5±0.2, 14.7±0.2, 16.1±0.2, 19.0±0.2, 20.4±0.2, and 23.7±0.2. In some embodiments, crystalline Form O of Compound (I) is characterized by an X-ray powder diffractogram having a signal at at least six two-theta values chosen from 7.2±0.2, 10.8±0.2, 12.3±0.2, 14.5±0.2, 14.7±0.2, 16.1±0.2, 19.0±0.2, 20.4±0.2, and 23.7±0.2. In some embodiments, crystalline Form O of Compound (I) is characterized by an X-ray powder diffractogram having a signal at at least five two-theta values chosen from 7.2±0.2, 10.8±0.2, 12.3±0.2, 14.5±0.2, 14.7±0.2, 16.1±0.2, 19.0±0.2, 20.4±0.2, and 23.7±0.2. In some embodiments, crystalline Form O of Compound (I) is characterized by an X-ray powder diffractogram having a signal at at least four two-theta values chosen from 7.2±0.2, 10.8±0.2, 12.3±0.2, 14.5±0.2, 14.7±0.2, 16.1±0.2, 19.0±0.2, 20.4±0.2, and 23.7±0.2. In some embodiments, crystalline Form O of Compound (I) is characterized by an X-ray powder diffractogram having a signal at at least three two-theta values chosen from 7.2±0.2, 10.8±0.2, 12.3±0.2, 14.5±0.2, 14.7±0.2, 16.1±0.2, 19.0±0.2, 20.4±0.2, and 23.7±0.2. In some embodiments, crystalline Form O of Compound (I) is characterized by an X-ray powder diffractogram having a signal at at least two two-theta values chosen from 7.2±0.2, 10.8±0.2, 12.3±0.2, 14.5±0.2, 14.7±0.2, 16.1±0.2, 19.0±0.2, 20.4±0.2, and 23.7±0.2. In some embodiments, crystalline Form O of Compound (I) is characterized by an X-ray powder diffractogram having a signal at at least one two-theta value chosen from 7.2±0.2, 10.8±0.2, 12.3±0.2, 14.5±0.2, 14.7±0.2, 16.1±0.2, 19.0±0.2, 20.4±0.2, and 23.7±0.2.

In some embodiments, crystalline Form O of Compound (I) is characterized by an X-ray powder diffractogram having a signal at at least three two-theta values chosen from 7.2±0.2, 12.3±0.2, 14.7±0.2, 16.1±0.2, and 23.7±0.2. In some embodiments, crystalline Form O of Compound (I) is characterized by an X-ray powder diffractogram having a signal at at least two two-theta values chosen from 7.2±0.2, 12.3±0.2, 14.7±0.2, 16.1±0.2, and 23.7±0.2. In some embodiments, crystalline Form O of Compound (I) is characterized by an X-ray powder diffractogram having a signal at at least one two-theta value chosen from 7.2±0.2, 12.3±0.2, 14.7±0.2, 16.1±0.2, and 23.7±0.2. In some embodiments, crystalline Form O of Compound (I) is characterized by an X-ray powder diffractogram having a signal at two-theta values of 7.2±0.2, 12.3±0.2, 14.7±0.2, 16.1±0.2, and 23.7±0.2.

In some embodiments, crystalline Form O of Compound (I) is characterized by a $^{13}$C NMR (CDCl$_3$, 100 MHz) pattern having a signal at at least one δ value (expressed as ppm) chosen from 32.1, 39.2, 43.5, 45.5, 55.6, 101.3, 115.2, 115.5, 116.0, 116.5, 117.9, 127.0, 127.7, 131.1, 137.1, 144.4, 146.7, 154.6, 156.3, 160.4, and 161.7.

In some embodiments, the present disclosure provides a process for preparing crystalline Form O of Compound (I) and also provides crystalline Form O of Compound (I) prepared by a process comprising: stagnant cooling of Compound (I) in tetrahydrofuran. In some embodiments, the process comprises stagnant cooling of Compound (I) in tetrahydrofuran from room temperature to −20° C. In some embodiments, the process further comprises collecting the crystalline Form O of Compound (I) by filtration.

In some embodiments, the present disclosure provides a process for preparing crystalline Form O of Compound (I) and also provides crystalline Form O of Compound (I) prepared by a process comprising: stagnant cooling of crystalline Form A of Compound (I) in tetrahydrofuran. In some embodiments, the process comprises stagnant cooling of crystalline Form A of Compound (I) in tetrahydrofuran from room temperature to −20° C. In some embodiments, the process further comprises collecting the crystalline Form O of Compound (I) by filtration.

Crystalline Form T of a Tosylate Salt of Compound (I)

In some embodiments, the present disclosure provides crystalline Form T of a tosylate salt of Compound (I):

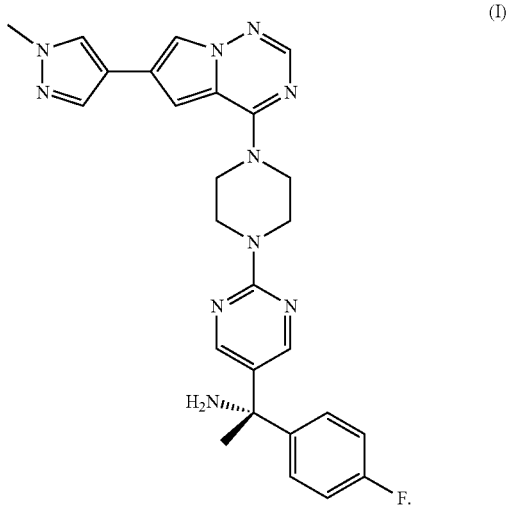 [SMILES: Cn1cc(-c2cc3c(N4CCN(c5ncc([C@@](C)(N)c6ccc(F)cc6)cn5)CC4)ncnn3c2)cn1]

(I)

Figure 8:
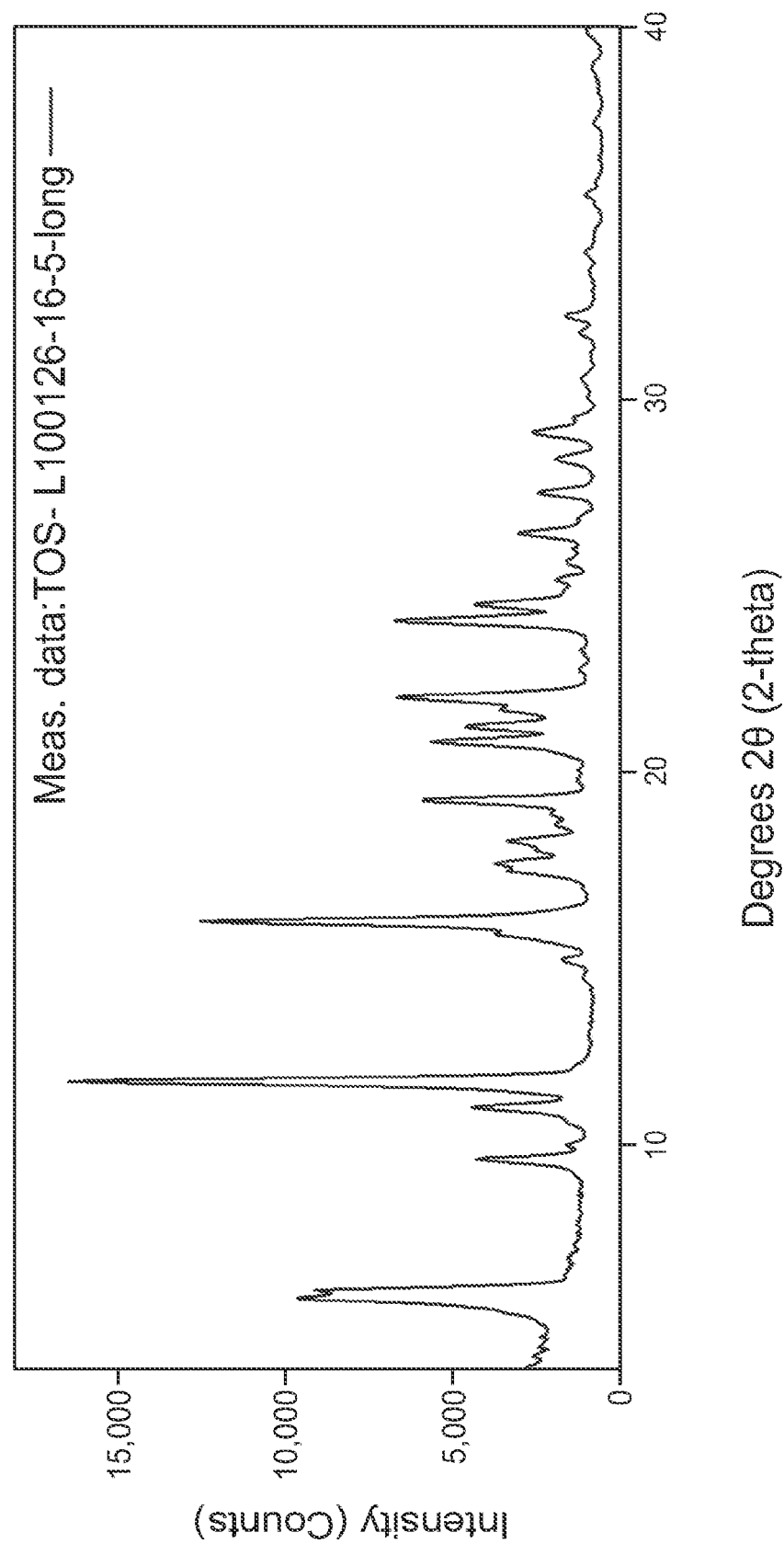
FIG. 8 shows an X-ray powder diffractogram for crystalline Form T of a tosylate salt of Compound (I), referred to as crystalline Form T herein, showing degrees 2θ (2-theta) on the X-axis and relative intensity on the Y-axis.

FIG. 8 shows an X-ray powder diffractogram for crystalline Form T of a tosylate salt of Compound (I) at ambient conditions.

In some embodiments, crystalline Form T of a tosylate salt of Compound (I) is a mono-tosylate salt of Compound (I), i.e., Form T comprises Compound (I) and tosylate in a 1:1 ratio.

In some embodiments, crystalline Form T of a tosylate salt of Compound (I) is characterized by a DSC thermogram having an endothermic event with an onset temperature of at 175° C., an endothermic event with an onset temperature of 189° C., and/or an endothermic event with an onset temperature of 207° C. In some embodiments, crystalline Form T of a tosylate salt of Compound (I) is characterized by a DSC thermogram having an endothermic event with a signal at 183° C., an endothermic event with a signal at 193° C., and/or an endothermic event with a signal at 213° C. In some embodiments, crystalline Form T of a tosylate salt of Compound (I) is characterized by a DSC thermogram having an endothermic event with an onset temperature of 175° C. and a signal at 183° C., an endothermic event with an onset temperature of 189° C. and a signal at 193° C., and/or an endothermic event with an onset temperature of 207° C. and a signal at 213° C.

In some embodiments, crystalline Form T of a tosylate salt of Compound (I) is characterized by solubility of 0.08 mg/mL in fasted state simulated intestinal fluid. In some embodiments, crystalline Form T of a tosylate salt of Compound (I) is characterized by solubility of 1.88 mg/mL in fasted state simulated gastric fluid. In some embodiments, crystalline Form T of a tosylate salt of Compound (I) is characterized by solubility of 0.08 mg/mL in fasted state simulated intestinal fluid at 37° C. In some embodiments, crystalline Form T of a tosylate salt of Compound (I) is characterized by solubility of 1.88 mg/mL in fasted state simulated gastric fluid at 37° C.

In some embodiments, crystalline Form T of a tosylate salt of Compound (I) is characterized by solubility of 0.34 mg/mL in water.

In some embodiments, crystalline Form T of a tosylate salt of Compound (I) is in substantially pure form. In some embodiments, crystalline Form T of a tosylate salt of Compound (I) is characterized by an X-ray powder diffractogram generated by an X-ray powder diffraction analysis with an incident beam of Cu Kα radiation. In some embodiments, crystalline Form T of a tosylate salt of Compound (I) is characterized by an X-ray powder diffractogram generated by an X-ray powder diffraction analysis with an incident beam of Cu Kα radiation with signals substantially similar to those recited in Table 5. Table 5.

TABLE 5

| 2-theta (deg) |
| --- |
| 5.86 |
| 6.07 |
| 9.60 |
| 10.99 |
| 11.70 |
| 14.96 |
| 15.68 |
| 15.97 |
| 17.34 |
| 17.57 |
| 18.10 |
| 18.87 |
| 19.21 |
| 20.80 |
| 21.20 |
| 21.66 |
| 22.03 |
| 23.33 |
| 24.07 |
| 24.51 |
| 25.19 |
| 25.59 |
| 26.41 |
| 27.50 |
| 28.40 |
| 29.13 |
| 30.56 |
| 31.76 |
| 32.22 |
| 33.98 |
| 35.47 |
| 37.45 |
| 38.96 |
| 39.80 |

In some embodiments, crystalline Form T of a tosylate salt of Compound (I) is characterized by an X-ray powder diffractogram having a signal at 5.9±0.2 degrees two-theta. In some embodiments, crystalline Form T of a tosylate salt of Compound (I) is characterized by an X-ray powder diffractogram having a signal at 6.1±0.2 degrees two-theta. In some embodiments, crystalline Form T of a tosylate salt of Compound (I) is characterized by an X-ray powder diffractogram having a signal at 9.6±0.2 degrees two-theta. In some embodiments, crystalline Form T of a tosylate salt of Compound (I) is characterized by an X-ray powder diffractogram having a signal at 11.7±0.2 degrees two-theta. In some embodiments, crystalline Form T of a tosylate salt of Compound (I) is characterized by an X-ray powder diffractogram having a signal at 16.0±0.2 degrees two-theta. In some embodiments, crystalline Form T of a tosylate salt of Compound (I) is characterized by an X-ray powder diffractogram having a signal at 19.2±0.2 degrees two-theta. In some embodiments, crystalline Form T of a tosylate salt of Compound (I) is characterized by an X-ray powder diffractogram having a signal at 20.8±0.2 degrees two-theta. In some embodiments, crystalline Form T of a tosylate salt of Compound (I) is characterized by an X-ray powder diffractogram having a signal at 21.2±0.2 degrees two-theta. In some embodiments, crystalline Form T of a tosylate salt of Compound (I) is characterized by an X-ray powder diffractogram having a signal at 22.0±0.2 degrees two-theta. In some embodiments, crystalline Form T of a tosylate salt of Compound (I) is characterized by an X-ray powder diffractogram having a signal at 24.1±0.2 degrees two-theta. In some embodiments, crystalline Form T of a tosylate salt of Compound (I) is characterized by an X-ray powder diffractogram having a signal at 24.5±0.2 degrees two-theta.

In some embodiments, crystalline Form T of a tosylate salt of Compound (I) is characterized by an X-ray powder diffractogram having a signal at two-theta values of 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2. In some embodiments, crystalline Form T of a tosylate salt of Compound (I) is characterized by an X-ray powder diffractogram having a signal at at least eight two-theta values chosen from 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2. In some embodiments, crystalline Form T of a tosylate salt of Compound (I) is characterized by an X-ray powder diffractogram having a signal at at least seven two-theta values chosen from 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2. In some embodiments, crystalline Form T of a tosylate salt of Compound (I) is characterized by an X-ray powder diffractogram having a signal at at least six two-theta values chosen from 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2. In some embodiments, crystalline Form T of a tosylate salt of Compound (I) is characterized by an X-ray powder diffractogram having a signal at at least five two-theta values chosen from 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2. In some embodiments, crystalline Form T of a tosylate salt of Compound (I) is characterized by an X-ray powder diffractogram having a signal at at least four two-theta values chosen from 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2. In some embodiments, crystalline Form T of a tosylate salt of Compound (I) is characterized by an X-ray powder diffractogram having a signal at at least three two-theta values chosen from 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2. In some embodiments, crystalline Form T of a tosylate salt of Compound (I) is characterized by an X-ray powder diffractogram having a signal at at least two two-theta values chosen from 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2. In some embodiments, crystalline Form T of a tosylate salt of Compound (I) is characterized by an X-ray powder diffractogram having a signal at at least one two-theta value chosen from 5.9±0.2, 6.1±0.2, 9.6±0.2, 11.7±0.2, 16.0±0.2, 19.2±0.2, 20.8±0.2, 21.2±0.2, 22.0±0.2, 24.1±0.2, and 24.5±0.2.

In some embodiments, crystalline Form T of a tosylate salt of Compound (I) is characterized by an X-ray powder diffractogram having a signal at at least three two-theta values chosen from 5.9±0.2, 11.7±0.2, 16.0±0.2, 22.0±0.2, and 24.5±0.2. In some embodiments, crystalline Form T of a tosylate salt of Compound (I) is characterized by an X-ray powder diffractogram having a signal at at least two two-theta values chosen from 5.9±0.2, 11.7±0.2, 16.0±0.2, 22.0±0.2, and 24.5±0.2. In some embodiments, crystalline Form T of a tosylate salt of Compound (I) is characterized by an X-ray powder diffractogram having a signal at at least one two-theta value chosen from 5.9±0.2, 11.7±0.2, 16.0±0.2, 22.0±0.2, and 24.5±0.2. In some embodiments, crystalline Form T of a tosylate salt of Compound (I) is characterized by an X-ray powder diffractogram having a signal at two-theta values of 5.9±0.2, 11.7±0.2, 16.0±0.2, 22.0±0.2, and 24.5±0.2.

In some embodiments, crystalline Form T of a tosylate salt of Compound (I) is characterized by an X-ray powder diffractogram substantially similar to that in FIG. 8.

In some embodiments, crystalline Form T of a tosylate salt of Compound (I) is characterized by a $^{13}$C NMR (DMSO-$d_6$, 500 MHz) pattern having a signal at at least one δ value (expressed as ppm) chosen from 20.7, 26.7, 38.5, 39.0, 40.0, 42.8, 44.9, 58.0, 102.2, 114.3, 115.5, 115.6, 115.8, 118.0, 123.6, 125.4, 127.6, 128.3, 128.4, 136.3, 137.7, 137.8, 145.2, 145.8, 153.2, 156.5, 160.1, 160.7, and 162.6.

In some embodiments, the present disclosure provides a process for preparing a crystalline Form T of a tosylate salt of Compound (I) and also provides crystalline Form T of a tosylate salt of Compound (I) prepared by a process comprising: adding Compound (I) and toluenesulfonic acid to a mixture of 2-propanol (IPA) and water; stirring at an elevated temperature; and reducing the temperature.

In some embodiments, 1.1 equivalents of toluenesulfonic acid is added. In some embodiments, the volumetric ratio of IPA to water in the mixture is 95:5. In some embodiments, stirring occurs at 600 rpm. In some embodiments, the elevated temperature is a temperature ranging from 48° C. to 50° C. In some embodiments, reducing the temperature comprises transferring the solution to a hot plate at a temperature ranging from 35° C. to 40° C.

Crystalline Form Tr of a Tartrate Salt of Compound (I)

In some embodiments, the present disclosure provides crystalline Form Tr of a tartrate salt of Compound (I):

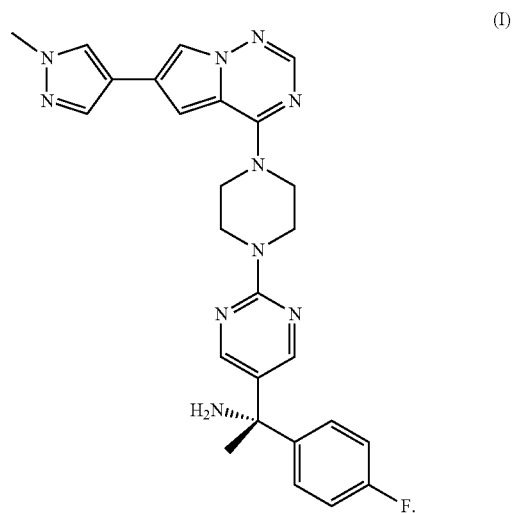 [SMILES: Cn1cc(-c2cc3c(N4CCN(c5ncc([C@@](C)(N)c6ccc(F)cc6)cn5)CC4)ncnn3c2)cn1]

(I)

Figure 9:
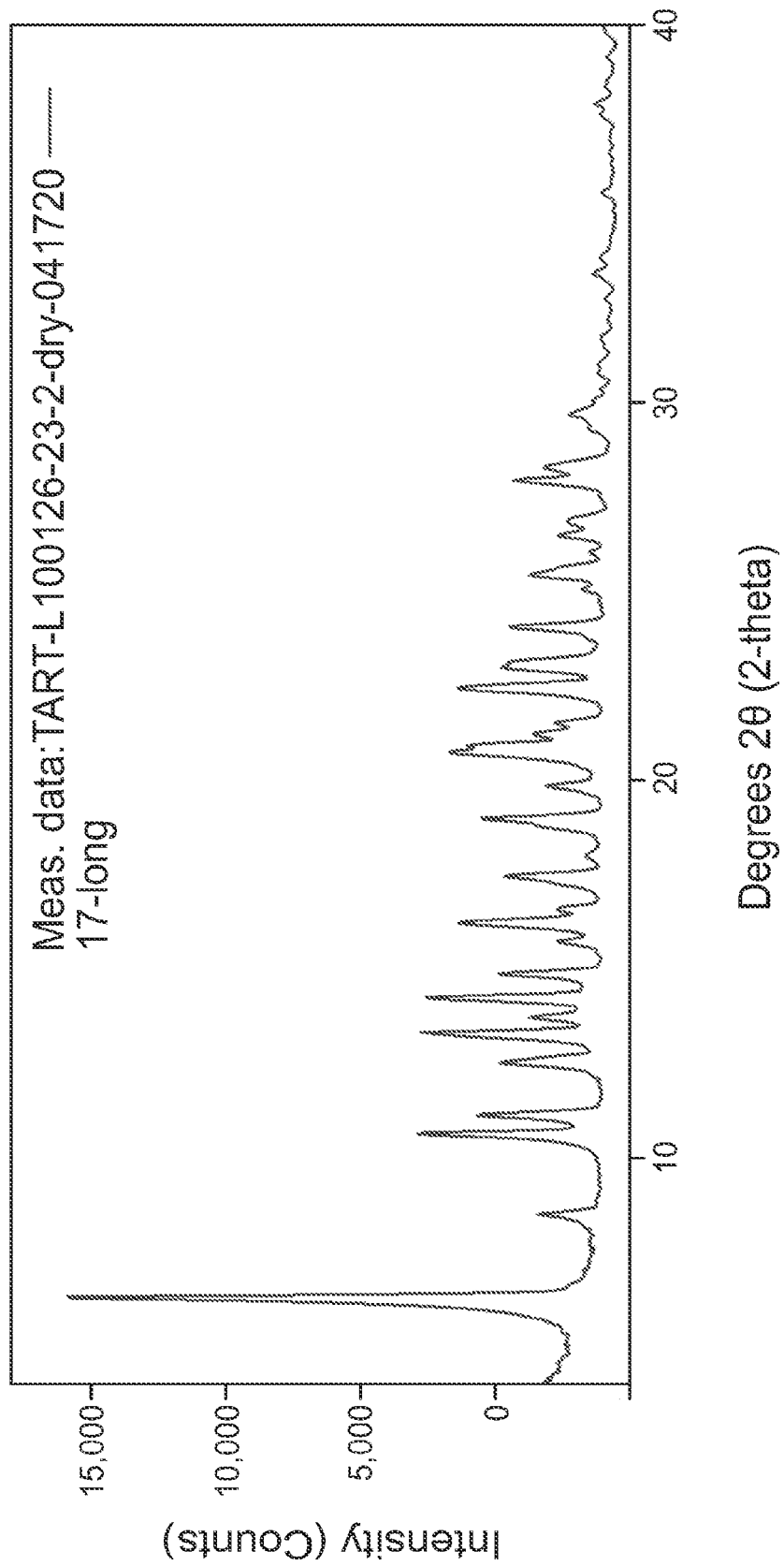
FIG. 9 shows an X-ray powder diffractogram for crystalline Form Tr of a tartrate salt of Compound (I), referred to as crystalline Form Tr herein, showing degrees 2θ (2-theta) on the X-axis and relative intensity on the Y-axis.

FIG. 9 shows an X-ray powder diffractogram for crystalline Form Tr of a tartrate salt of Compound (I) at ambient conditions.

In some embodiments, crystalline Form Tr of a tartrate salt of Compound (I) is a mono-tartrate salt, e.g., Form Tr comprises Compound (I) and tosylate in a 1:1 ratio.

In some embodiments, crystalline Form Tr of a tartrate salt of Compound (I) is characterized by a DSC onset at 144.5° C., followed by an exothermic event (recrystallization) at 158.8° C. In some embodiments, the endotherm coincides with a mass loss of 4.5 wt. % by TGA.

In some embodiments, crystalline Form Tr of a tartrate salt of Compound (I) is further characterized by a DSC thermogram having an endothermic event with an onset temperature of 145° C., an exothermic event with an onset temperature of 159° C., an endothermic event with an onset temperature of 205° C., an endothermic event with an onset temperature of 237° C., and/or an exothermic event with an onset temperature of 254° C. In some embodiments, crystalline Form Tr of a tartrate salt of Compound (I) is characterized by a DSC thermogram having an endothermic event with a signal at 156° C., an exothermic event with a signal at 163° C., an endothermic event with a signal at 213° C., an endothermic event with a signal at 243° C., and/or an exothermic event with a signal at 257° C. In some embodiments, crystalline Form Tr of a tartrate salt of Compound (I) is characterized by a DSC thermogram having an endothermic event with an onset temperature of 145° C. and a signal temperature of 156° C., an exothermic event with an onset temperature of 159° C. and a signal temperature of 163° C., an endothermic event with an onset temperature of 205° C. and a signal temperature of 213° C., an endothermic event with an onset temperature of 237° C. and a signal temperature of 243° C., and/or an exothermic event with an onset temperature of 254° C. and a signal temperature of 257° C.

In some embodiments, crystalline Form Tr of a tartrate salt of Compound (I) is characterized by solubility of 0.27 mg/mL in fasted state simulated intestinal fluid. In some embodiments, crystalline Form T of a tosylate salt of Compound (I) is characterized by solubility of 4.79 mg/mL in fasted state simulated gastric fluid. In some embodiments, crystalline Form Tr of a tartrate salt of Compound (I) is characterized by solubility of 0.27 mg/mL in fasted state simulated intestinal fluid at 37° C. In some embodiments, crystalline Form T of a tosylate salt of Compound (I) is characterized by solubility of 4.79 mg/mL in fasted state simulated gastric fluid at 37° C.

In some embodiments, crystalline Form T of a tosylate salt of Compound (I) is characterized by solubility of 0.84 mg/mL in water.

In some embodiments, the crystalline Form Tr of a tartrate salt of Compound (I) is characterized by a weight change of 4.4% in a dynamic vapor sorption experiment, while varying the relative humidity from 2-95% RH at room temperature. In some embodiments, the crystalline Form Tr of a tartrate salt of Compound (I) is characterized by a weight change of 2.95% to 3% in a dynamic vapor sorption experiment, while varying the relative humidity from 2-30% RH at room temperature.

In some embodiments, crystalline Form Tr of a tartrate salt of Compound (I) is in substantially pure form. In some embodiments, crystalline Form Tr of a tartrate salt of Compound (I) is characterized by an X-ray powder diffractogram generated by an X-ray powder diffraction analysis with an incident beam of Cu Kα radiation. In some embodiments, crystalline Form Tr of a tartrate salt of Compound (I) is characterized by an X-ray powder diffractogram generated by an X-ray powder diffraction analysis with an incident beam of Cu Kα radiation with signals substantially similar to those recited in Table 6. Table 6.

TABLE 6

| 2-theta (deg) |
| --- |
| 6.28 |
| 8.50 |
| 10.61 |
| 11.12 |
| 12.52 |
| 13.29 |
| 13.68 |
| 14.23 |
| 14.86 |
| 15.71 |
| 16.22 |
| 16.58 |
| 17.49 |
| 18.99 |
| 19.83 |
| 20.72 |
| 20.91 |
| 21.22 |
| 21.50 |
| 22.46 |
| 22.97 |
| 23.14 |
| 24.05 |
| 25.04 |
| 25.44 |
| 26.02 |
| 26.48 |
| 26.87 |
| 27.92 |
| 28.29 |
| 29.30 |
| 29.69 |
| 30.88 |
| 31.70 |
| 33.47 |
| 33.87 |
| 35.53 |
| 37.59 |
| 37.92 |
| 38.42 |
| 39.95 |

In some embodiments, crystalline Form Tr of a tartrate salt of Compound (I) is characterized by an X-ray powder diffractogram having a signal at 6.3±0.2 degrees two-theta. In some embodiments, crystalline Form Tr of a tartrate salt of Compound (I) is characterized by an X-ray powder diffractogram having a signal at 10.6±0.2 degrees two-theta. In some embodiments, crystalline Form Tr of a tartrate salt of Compound (I) is characterized by an X-ray powder diffractogram having a signal at 11.1±0.2 degrees two-theta. In some embodiments, crystalline Form Tr of a tartrate salt of Compound (I) is characterized by an X-ray powder diffractogram having a signal at 12.5±0.2 degrees two-theta. In some embodiments, crystalline Form Tr of a tartrate salt of Compound (I) is characterized by an X-ray powder diffractogram having a signal at 13.3±0.2 degrees two-theta. In some embodiments, crystalline Form Tr of a tartrate salt of Compound (I) is characterized by an X-ray powder diffractogram having a signal at 13.7±0.2 degrees two-theta. In some embodiments, crystalline Form Tr of a tartrate salt of Compound (I) is characterized by an X-ray powder diffractogram having a signal at 14.2±0.2 degrees two-theta. In some embodiments, crystalline Form Tr of a tartrate salt of Compound (I) is characterized by an X-ray powder diffractogram having a signal at 14.9±0.2 degrees two-theta. In some embodiments, crystalline Form Tr of a tartrate salt of Compound (I) is characterized by an X-ray powder diffractogram having a signal at 16.2±0.2 degrees two-theta. In some embodiments, crystalline Form Tr of a tartrate salt of Compound (I) is characterized by an X-ray powder diffractogram having a signal at 19.0±0.2 degrees two-theta. In some embodiments, crystalline Form Tr of a tartrate salt of Compound (I) is characterized by an X-ray powder diffractogram having a signal at 22.5±0.2 degrees two-theta. In some embodiments, crystalline Form Tr of a tartrate salt of Compound (I) is characterized by an X-ray powder diffractogram having a signal at 24.1±0.2 degrees two-theta. In some embodiments, crystalline Form Tr of a tartrate salt of Compound (I) is characterized by an X-ray powder diffractogram having a signal at 27.9±0.2 degrees two-theta.

In some embodiments, crystalline Form Tr of a tartrate salt of Compound (I) is characterized by an X-ray powder diffractogram having a signal at two-theta values of 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2. In some embodiments, crystalline Form Tr of a tartrate salt of Compound (I) is characterized by an X-ray powder diffractogram having a signal at at least eight two-theta values chosen from 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2. In some embodiments, crystalline Form Tr of a tartrate salt of Compound (I) is characterized by an X-ray powder diffractogram having a signal at at least seven two-theta values chosen from 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2. In some embodiments, crystalline Form Tr of a tartrate salt of Compound (I) is characterized by an X-ray powder diffractogram having a signal at at least six two-theta values chosen from 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2. In some embodiments, crystalline Form Tr of a tartrate salt of Compound (I) is characterized by an X-ray powder diffractogram having a signal at at least five two-theta values chosen from 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2. In some embodiments, crystalline Form Tr of a tartrate salt of Compound (I) is characterized by an X-ray powder diffractogram having a signal at at least four two-theta values chosen from 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2. In some embodiments, crystalline Form Tr of a tartrate salt of Compound (I) is characterized by an X-ray powder diffractogram having a signal at at least three two-theta values chosen from 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2. In some embodiments, crystalline Form Tr of a tartrate salt of Compound (I) is characterized by an X-ray powder diffractogram having a signal at at least two two-theta values chosen from 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2. In some embodiments, crystalline Form Tr of a tartrate salt of Compound (I) is characterized by an X-ray powder diffractogram having a signal at at least one two-theta value chosen from 6.3±0.2, 10.6±0.2, 11.1±0.2, 12.5±0.2, 13.3±0.2, 13.7±0.2, 14.2±0.2, 14.9±0.2, 16.2±0.2, 19.0±0.2, 22.5±0.2, 24.1±0.2, and 27.9±0.2.

In some embodiments, crystalline Form Tr of a tartrate salt of Compound (I) is characterized by an X-ray powder diffractogram having a signal at at least three two-theta values chosen from 6.3±0.2, 10.6±0.2, 12.5±0.2, 13.3±0.2, 13.7±0.2, 22.5±0.2, and 27.9±0.2. In some embodiments, crystalline Form Tr of a tartrate salt of Compound (I) is characterized by an X-ray powder diffractogram having a signal at at least two two-theta values chosen from 6.3±0.2, 10.6±0.2, 12.5±0.2, 13.3±0.2, 13.7±0.2, 22.5±0.2, and 27.9±0.2. In some embodiments, crystalline Form Tr of a tartrate salt of Compound (I) is characterized by an X-ray powder diffractogram having a signal at at least one two-theta value chosen from 6.3±0.2, 10.6±0.2, 12.5±0.2, 13.3±0.2, 13.7±0.2, 22.5±0.2, and 27.9±0.2. In some embodiments, crystalline Form Tr of a tartrate salt of Compound (I) is characterized by an X-ray powder diffractogram having a signal at two-theta values of 6.3±0.2, 10.6±0.2, 12.5±0.2, 13.3±0.2, 13.7±0.2, 22.5±0.2, and 27.9±0.2.

In some embodiments, crystalline Form Tr of a tartrate salt of Compound (I) is characterized by an X-ray powder diffractogram substantially similar to that in FIG. 9.

In some embodiments, crystalline Form Tr of a tartrate salt of Compound (I) is characterized by a $^{13}$C NMR (DMSO-$d_6$, 500 MHz) pattern having a signal at at least one δ value (expressed as ppm) chosen from 28.5, 38.2, 42.9, 43.0, 44.7, 44.8, 44.9, 56.7, 71.8, 101.6, 114.3, 115.3, 115.5, 115.6, 115.8, 118.0, 127.5, 128.2, 128.3, 136.4, 141.2, 146.5, 153.7, 156.3, 160.0, 160.2, 162.1, and 173.9.

In some embodiments, the present disclosure provides crystalline Form Tr of a tartrate salt of Compound (I) prepared by a process comprising: adding Compound (I) and tartaric acid to a tetrafluoroethylene, ethanol, and water mixture; stirring; evaporating with gentle stirring; adding acetone and heating to an elevated temperature; and decreasing the temperature.

Crystalline Form H of a Hydrochloride Salt of Compound (I)

In some embodiments, the present disclosure provides crystalline Form H of a hydrochloride salt of Compound (I):

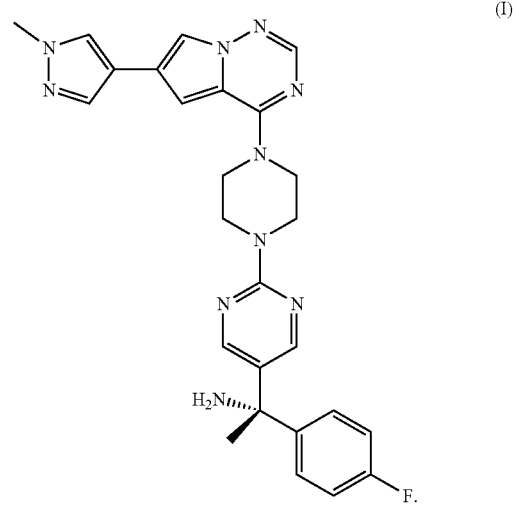 [SMILES: Cn1cc(-c2cc3c(N4CCN(c5ncc([C@@](C)(N)c6ccc(F)cc6)cn5)CC4)ncnn3c2)cn1]

(I)

Figure 10:
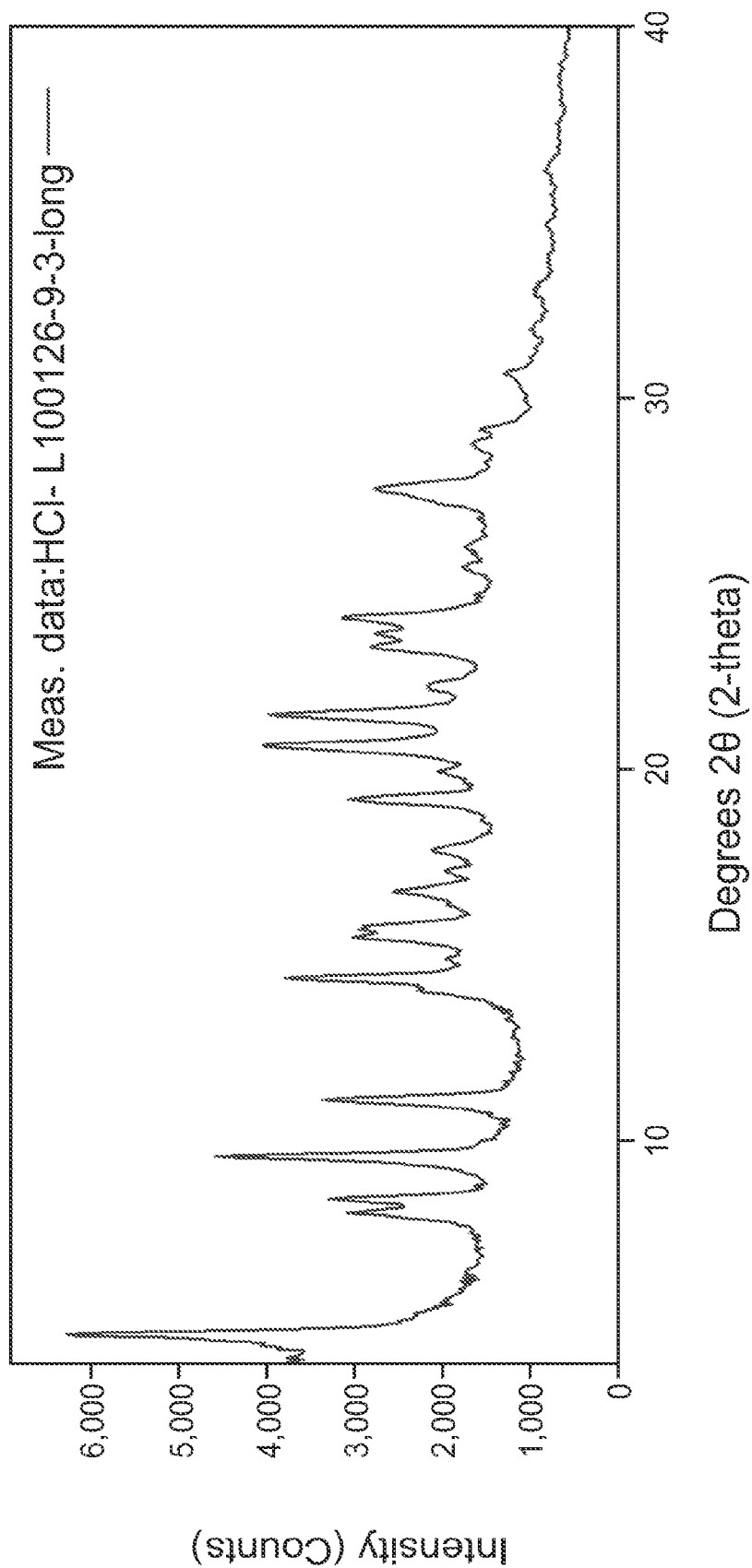
FIG. 10 shows an X-ray powder diffractogram for crystalline Form H of a hydrochloride salt of Compound (I), referred to as crystalline Form H herein, showing degrees 2θ (2-theta) on the X-axis and relative intensity on the Y-axis.

FIG. 10 shows an X-ray powder diffractogram for crystalline Form H of a hydrochloride salt of Compound (I) at ambient conditions.

In some embodiments, crystalline Form H of a hydrochloride salt of Compound (I) is a mono-hydrochloride salt, e.g., Form H comprises Compound (I) and hydrochloride in a 1:1 ratio.

In some embodiments, crystalline Form H of a hydrochloride salt of Compound (I) is characterized by a TGA thermal curve having an endotherm at 156° C. followed by a recrystallization event, which is associated with 3.3-3.9 wt.

% mass loss. In some embodiments, crystalline Form H of a hydrochloride salt of Compound (I) is characterized by a DSC thermogram having an endothermic event with an onset temperature of 156° C., an exothermic event with an onset temperature of 173° C., and/or an endothermic event with an onset temperature of 210° C. In some embodiments, crystalline Form H of a hydrochloride salt of Compound (I) is characterized by a DSC thermogram having an endothermic event with a signal at 165° C., an exothermic event with a signal at 176° C., and/or an endothermic event with a signal at 215° C. In some embodiments, crystalline Form H of a hydrochloride salt of Compound (I) is characterized by a DSC thermogram having an endothermic event with an onset temperature of 156° C. and a peak temperature of 165° C., an exothermic event with an onset temperature of 173° C. and a peak temperature of 176° C., and/or an endothermic event with an onset temperature of 210° C. and a peak temperature of 215° C.

In some embodiments, crystalline Form H of a hydrochloride salt of Compound (I) is characterized by solubility of 0.10 mg/mL in fasted state simulated intestinal fluid. In some embodiments, crystalline Form H of a hydrochloride salt of Compound (I) is characterized by solubility of 4.18 mg/mL in fasted state simulated gastric fluid. In some embodiments, crystalline Form H of a hydrochloride salt of Compound (I) is characterized by solubility of 0.10 mg/mL in fasted state simulated intestinal fluid at 37° C. In some embodiments, crystalline Form H of a hydrochloride salt of Compound (I) is characterized by solubility of 4.18 mg/mL in fasted state simulated gastric fluid at 37° C.

In some embodiments, crystalline Form H of a hydrochloride salt of Compound (I) is characterized by solubility of 2.86 mg/mL in water.

In some embodiments, crystalline Form H of a hydrochloride salt of Compound (I) is characterized by a weight change of 15% in a dynamic vapor sorption experiment, while varying the relative humidity (RH) from 2-95% RH at room temperature. In some embodiments, crystalline Form H of a hydrochloride salt of Compound (I) is characterized by a weight change of 10.8% in a dynamic vapor sorption experiment, while varying the relative humidity from 80-95% RH at room temperature.

In some embodiments, crystalline Form H of a hydrochloride salt of Compound (I) is in substantially pure form. In some embodiments, crystalline Form H of a hydrochloride salt of Compound (I) is characterized by an X-ray powder diffractogram generated by an X-ray powder diffraction analysis with an incident beam of Cu Kα radiation. In some embodiments, crystalline Form H of a hydrochloride salt of Compound (I) is characterized by an X-ray powder diffractogram generated by an X-ray powder diffraction analysis with an incident beam of Cu Kα radiation with signals substantially similar to those recited in Table 7.

TABLE 7

| 2-theta (deg) |
| --- |
| 4.81 |
| 8.08 |
| 8.46 |
| 9.60 |
| 11.11 |
| 14.44 |
| 14.90 |
| 15.77 |
| 16.77 |

TABLE 7-continued

| 2-theta (deg) |
| --- |
| 17.31 |
| 17.87 |
| 19.17 |
| 20.65 |
| 21.50 |
| 22.33 |
| 23.31 |
| 23.67 |
| 24.09 |
| 25.47 |
| 26.09 |
| 27.59 |
| 29.10 |
| 30.69 |
| 31.96 |
| 33.07 |

In some embodiments, crystalline Form H of a hydrochloride salt of Compound (I) is characterized by an X-ray powder diffractogram having a signal at 4.8±0.2 degrees two-theta. In some embodiments, crystalline Form H of a hydrochloride salt of Compound (I) is characterized by an X-ray powder diffractogram having a signal at 8.1±0.2 degrees two-theta. In some embodiments, crystalline Form H of a hydrochloride salt of Compound (I) is characterized by an X-ray powder diffractogram having a signal at 8.5±0.2 degrees two-theta. In some embodiments, crystalline Form H of a hydrochloride salt of Compound (I) is characterized by an X-ray powder diffractogram having a signal at 9.6±0.2 degrees two-theta. In some embodiments, crystalline Form H of a hydrochloride salt of Compound (I) is characterized by an X-ray powder diffractogram having a signal at 11.1±0.2 degrees two-theta. In some embodiments, crystalline Form H of a hydrochloride salt of Compound (I) is characterized by an X-ray powder diffractogram having a signal at 20.7±0.2 degrees two-theta. In some embodiments, crystalline Form H of a hydrochloride salt of Compound (I) is characterized by an X-ray powder diffractogram having a signal at 21.5±0.2 degrees two-theta. In some embodiments, crystalline Form H of a hydrochloride salt of Compound (I) is characterized by an X-ray powder diffractogram having a signal at 23.3±0.2 degrees two-theta. In some embodiments, crystalline Form H of a hydrochloride salt of Compound (I) is characterized by an X-ray powder diffractogram having a signal at 23.7±0.2 degrees two-theta. In some embodiments, crystalline Form H of a hydrochloride salt of Compound (I) is characterized by an X-ray powder diffractogram having a signal at 24.1±0.2 degrees two-theta. In some embodiments, crystalline Form H of a hydrochloride salt of Compound (I) is characterized by an X-ray powder diffractogram having a signal at 27.6±0.2 degrees two-theta.

In some embodiments, crystalline Form H of a hydrochloride salt of Compound (I) is characterized by an X-ray powder diffractogram having a signal at two-theta values of 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2. In some embodiments, crystalline Form H of a hydrochloride salt of Compound (I) is characterized by an X-ray powder diffractogram having a signal at at least eight two-theta values chosen from 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2. In some embodiments, crystalline Form H of a hydrochloride salt of Compound (I) is characterized by an X-ray powder diffractogram having a signal at at least seven two-theta values chosen from 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2. In some embodiments, crystalline Form H of a hydrochloride salt of Compound (I) is characterized by an X-ray powder diffractogram having a signal at at least six two-theta values chosen from 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2. In some embodiments, crystalline Form H of a hydrochloride salt of Compound (I) is characterized by an X-ray powder diffractogram having a signal at at least five two-theta values chosen from 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2. In some embodiments, crystalline Form H of a hydrochloride salt of Compound (I) is characterized by an X-ray powder diffractogram having a signal at at least four two-theta values chosen from 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2. In some embodiments, crystalline Form H of a hydrochloride salt of Compound (I) is characterized by an X-ray powder diffractogram having a signal at at least three two-theta values chosen from 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2. In some embodiments, crystalline Form H of a hydrochloride salt of Compound (I) is characterized by an X-ray powder diffractogram having a signal at at least two two-theta values chosen from 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2. In some embodiments, crystalline Form H of a hydrochloride salt of Compound (I) is characterized by an X-ray powder diffractogram having a signal at at least one two-theta value chosen from 4.8±0.2, 8.1±0.2, 8.5±0.2, 9.6±0.2, 11.1±0.2, 20.7±0.2, 21.5±0.2, 23.3±0.2, 23.7±0.2, 24.1±0.2, and 27.6±0.2.

In some embodiments, crystalline Form H of a hydrochloride salt of Compound (I) is characterized by an X-ray powder diffractogram having a signal at at least three two-theta values chosen from 4.8±0.2, 8.1±0.2, 11.1±0.2, 20.7±0.2, and 23.7±0.2. In some embodiments, crystalline Form H of a hydrochloride salt of Compound (I) is characterized by an X-ray powder diffractogram having a signal at at least two two-theta values chosen from 4.8±0.2, 8.1±0.2, 11.1±0.2, 20.7±0.2, and 23.7±0.2. In some embodiments, crystalline Form H of a hydrochloride salt of Compound (I) is characterized by an X-ray powder diffractogram having a signal at at least one two-theta value chosen from 4.8±0.2, 8.1±0.2, 11.1±0.2, 20.7±0.2, and 23.7±0.2. In some embodiments, crystalline Form H of a hydrochloride salt of Compound (I) is characterized by an X-ray powder diffractogram having a signal at two-theta values of 4.8±0.2, 8.1±0.2, 11.1±0.2, 20.7±0.2, and 23.7±0.2.

In some embodiments, crystalline Form H of a hydrochloride salt of Compound (I) is characterized by an X-ray powder diffractogram substantially similar to that in FIG. 10.

In some embodiments, crystalline Form H of a hydrochloride salt of Compound (I) is characterized by a $^{13}C$ NMR (DMSO-$d_6$, 500 MHz) pattern having a signal at at least one δ value (expressed as ppm) chosen from 26.7, 42.8, 44.9, 58.0, 102.2, 114.3, 115.3, 115.5, 115.6, 115.8, 118.0, 123.9, 127.6, 128.5, 136.4, 138.1, 138.2, 145.7, 153.2, 156.6, 160.0, 160.6, and 162.5.

In some embodiments, the present disclosure provides a process for preparing crystalline Form H of a hydrochloride salt of Compound (I) and also provides crystalline Form H of a hydrochloride salt of Compound (I) prepared by a process comprising: adding Compound (I) to a concentrated hydrochloride solution in ethanol; adding tetrafluoroethylene (TFE); and stirring at an elevated temperature. In some embodiments, 1.1 equivalents of a concentrated HCl solution in ethanol is used. In some embodiments, the elevated temperature ranges from 35° C. to 40° C. In some embodiments, stirring at an elevated temperature occurs for thirty minutes at 340 rpm. In some embodiments, a spatula is used to break up gumming after fifteen minutes of stirring at 340 rpm. In some embodiments, additional TFE is added after stirring at an elevated temperature. In some embodiments, more stirring occurs at room temperature after adding additional TFE.

In some embodiments, the present disclosure provides a process for preparing crystalline Form H of a hydrochloride salt of Compound (I) and also provides crystalline Form H of a hydrochloride salt of Compound (I) prepared by a process comprising slurrying Compound (I) in fasted state simulated gastric fluid at 37° C.

Methods of Preparing Compound (I)

In some embodiments, the present disclosure provides a method of preparing (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-1-amine (Compound (I))

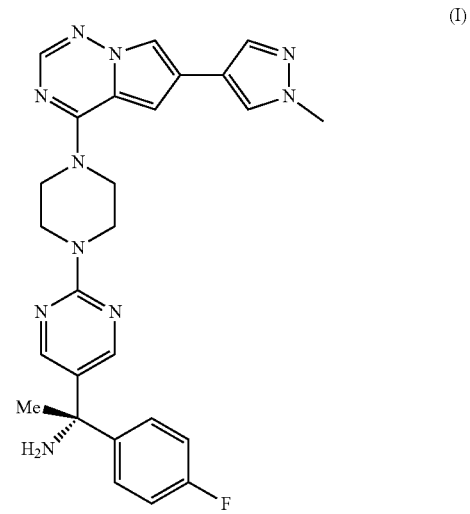 [SMILES: Cn1cc(-c2cc3c(N4CCN(c5ncc([C@@](C)(N)c6ccc(F)cc6)cn5)CC4)ncnn3c2)cn1]

or a pharmaceutically acceptable salt thereof.

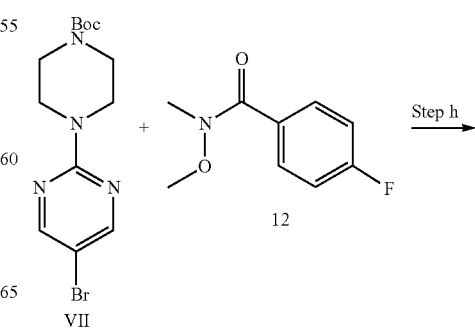

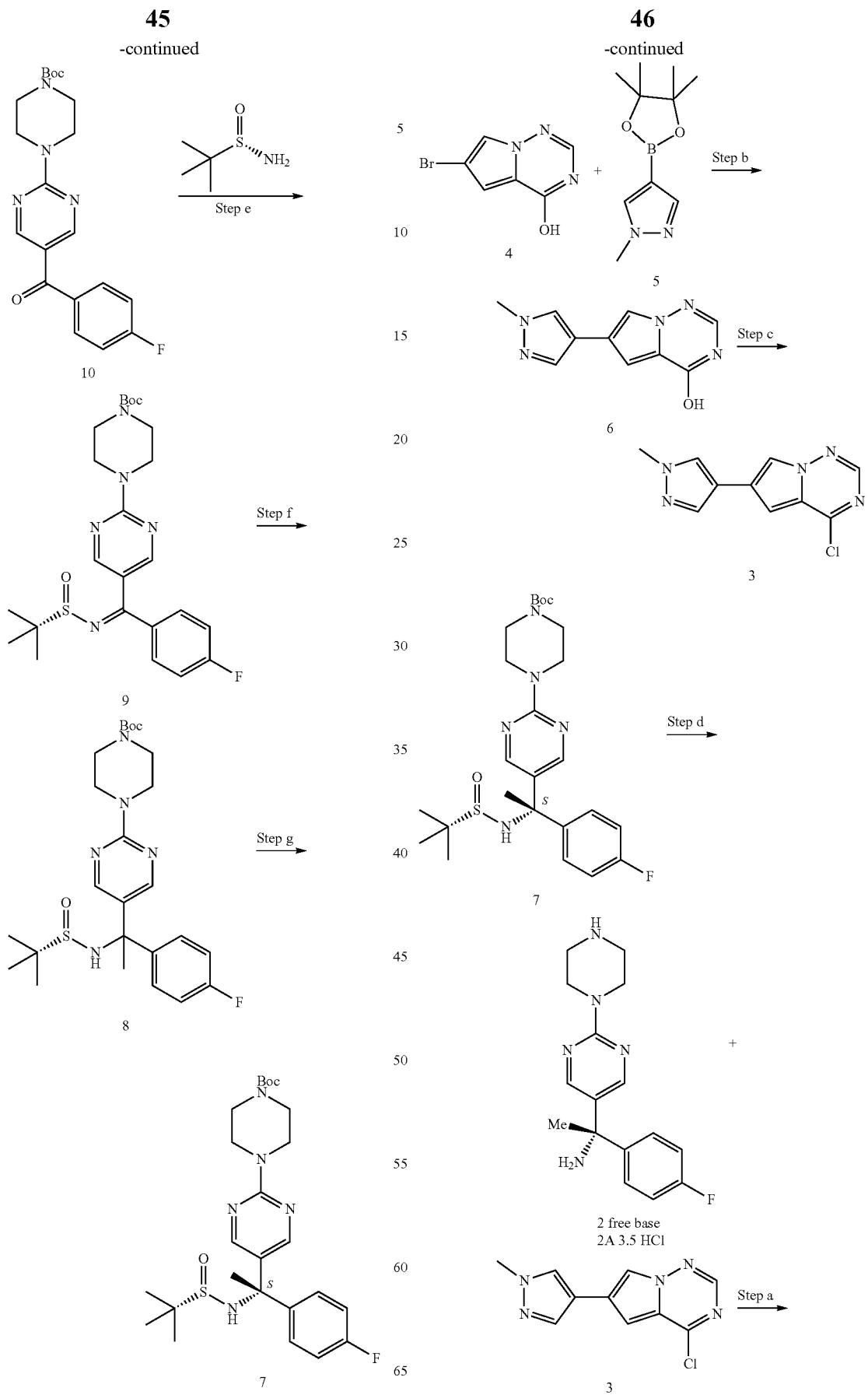

-continued

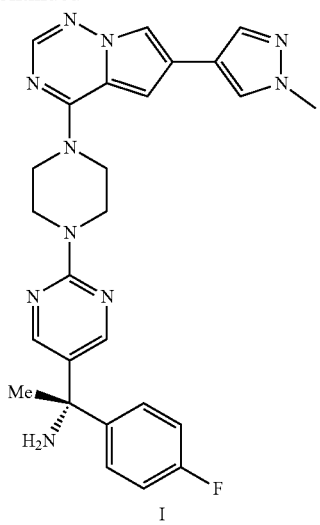

I

In some embodiments, the present disclosure provides a process of preparing Compound (I) comprising the step of converting a compound of Formula (VI):

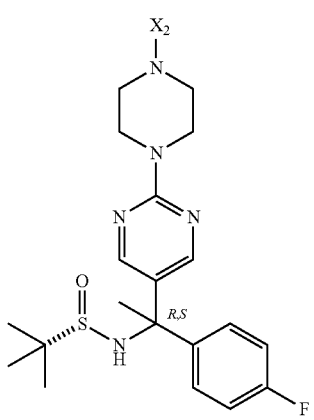
(VI)

to compound of Formula (III):

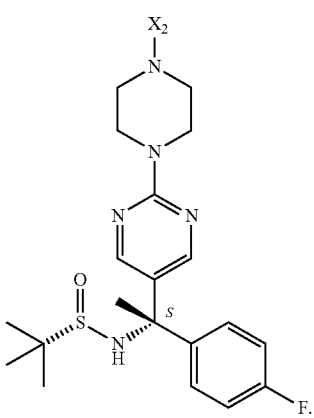
(III)

In some embodiments, the compound of Formula (III) is diastereomerically pure. The desired diastereomer has the S configuration at the carbon center.

In some embodiments, the compound of Formula (III) is substantially free of the undesired diastereomers (C) and (D):

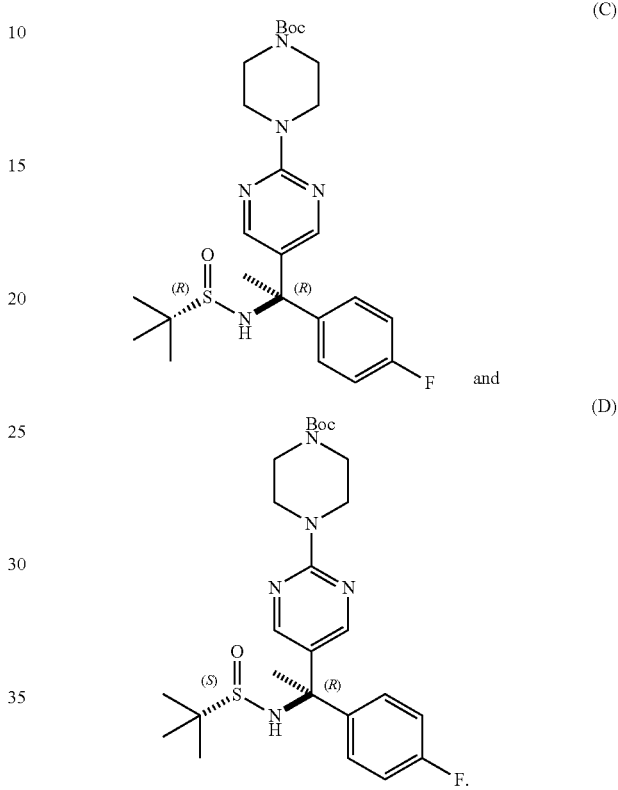

In some embodiments, the amount of (C) and (D) is not more than 0.4% w/w (measured by HPLC). In some embodiments, the diastereomeric purity is >97% de (diastereomeric excess). In some embodiments, the diastereomic purity is >98% de. In some embodiments, the diastereomeric purity is >98.5% de. In some embodiments, the diastereomeric purity is >99% de. In some embodiments, the diastereomeric purity is >99.5% de. In some embodiments, the diastereomeric purity is >99.6% de. In some embodiments, the diastereomeric purity is >99.7% de. In some embodiments, the diastereomeric purity is >99.8%.

In some embodiments, $X_2$ is chosen from a carbamate protecting group, benzyl, tetrahydropyranyl, acetamide, trifluoroacetamide, triphenylmethylamine, benzylideneamine, and p-toluenesulfonamide. In some embodiments, $X_2$ is benzyl. In some embodiments, $X_2$ is tetrahydropyranyl. In some embodiments, $X_2$ is acetamide. In some embodiments, $X_2$ is trifluoroacetamide. In some embodiments, $X_2$ is triphenylmethylamine. In some embodiments, $X_2$ is benzylideneamine. In some embodiments, $X_2$ is p-toluenesulfonamide. In some embodiments, $X_2$ is a carbamate protecting group. In some embodiments, the carbamate protecting group is tert-butyl carbamate, 9-fluorenylmethyl carbamate, and benzyl carbamate. In some embodiments, $X_2$ is tert-butyl carbamate. In some embodiments, $X_2$ is 9-fluorenylmethyl carbamate. In some embodiments, $X_2$ is benzyl carbamate.

The present disclosure provides a process of preparing a compound of Formula (III) in a diastereomerically pure form, such as, e.g., compound 7. It has been discovered that the diastereomeric purity of a compound of Formula (III) is important to ensuring the purity of the final Compound (I). In some embodiments, the process of preparing a compound of Formula (III) in a diastereomerically pure form involves trituration. In some embodiments, the trituration solvent in the step of triturating a compound of Formula (VI) comprises n-heptane and methanol. In some embodiments, the process of preparing a compound of Formula III in a diastereomerically pure form involves recrystallization. In some embodiments, the recrystallization solvent is isopropanol. In some embodiments, the recrystallization solvent is a mixture of ethyl acetate and heptane.

In some embodiments, the present disclosure provides processes of preparing (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-1-amine (Compound (I)):

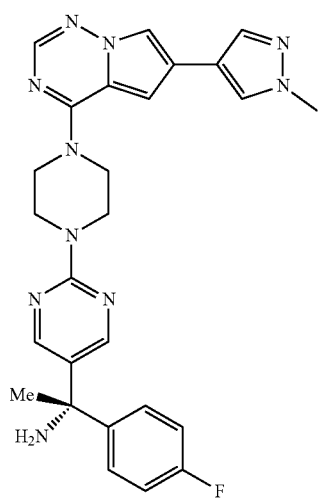

or a pharmaceutically acceptable salt thereof, comprising:
(a) reacting (S)-1-(2-(4λ²-piperazin-1-yl)pyrimidin-5-yl)-1-(4-fluorophenyl)ethan-1-amine (2) or a salt thereof;

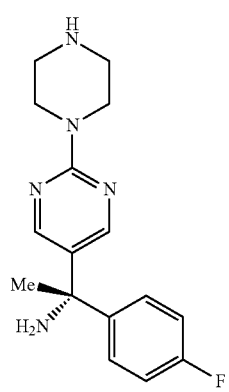

and a compound of Formula (I):

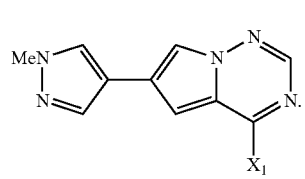

In some embodiments, $X_1$ is a halogen or activated phenol. In some embodiments, $X_1$ is a halogen. In some embodiments, $X_1$ is F, Cl, Br, or I. In some embodiments, $X_1$ is F. In some embodiments, $X_1$ is Cl. In some embodiments, $X_1$ is Br. In some embodiments, $X_1$ is I. In some embodiments, $X_1$ is activated phenol. In some embodiments, $X_1$ is tosylate or mesylate.

In some embodiments, (S)-1-(2-(4λ²-piperazin-1-yl)pyrimidin-5-yl)-1-(4-fluorophenyl)ethan-1-amine (2) is a free base. In some embodiments, the salt of (S)-1-(2-(4λ²-piperazin-1-yl)pyrimidin-5-yl)-1-(4-fluorophenyl)ethan-1-amine (2) is a hydrochloride salt or trifluoroacetic acid salt. In some embodiments, the salt of (S)-1-(2-(4λ²-piperazin-1-yl)pyrimidin-5-yl)-1-(4-fluorophenyl)ethan-1-amine (2) is a hydrochloride salt. In some embodiments, the hydrochloride salt of (S)-1-(2-(4λ²-piperazin-1-yl)pyrimidin-5-yl)-1-(4-fluorophenyl)ethan-1-amine (II) is (S)-1-(2-(4λ²-piperazin-1-yl)pyrimidin-5-yl)-1-(4-fluorophenyl)ethan-1-amine·3.5 HCl (2A). In some embodiments, the salt of (S)-1-(2-(4λ²-piperazin-1-yl)pyrimidin-5-yl)pyrimidin-5-yl)-1-(4-fluorophenyl)ethan-1-amine (2) is a trifluoroacetic acid salt.

In some embodiments, the 4-chloro-6-(1-methyl-1H-pyrazol-4-yl)pyrrolo[2,1-f][1,2,4]triazine (3):

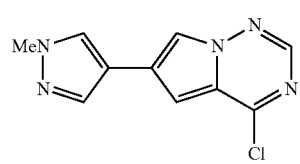

is prepared by
(b) reacting 6-bromopyrrolo[2,1-f][1,2,4]triazin-4-ol (4):

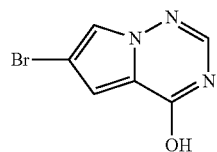

and a compound of Formula (II):

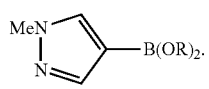

to form 6-(1-methyl-1H-pyrazol-4-yl)pyrrolo[2,1-f][1,2,4]triazin-4-ol (6):

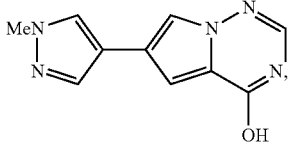
(6)

(c) converting 6-(1-methyl-1H-pyrazol-4-yl)pyrrolo[2,1-f][1,2,4]triazin-4-ol (6):

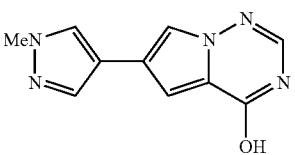
(6)

into 4-chloro-6-(1-methyl-1H-pyrazol-4-yl)pyrrolo[2,1-f][1,2,4]triazine (3):

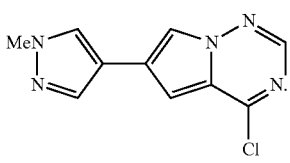
(3)

In some embodiments, B(OR)$_2$ is chosen from: catecholborane:

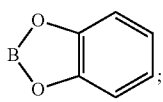
;

pinacolborane:

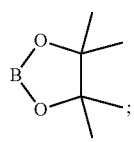
;

and
boronic acids.

In some embodiments, B(OR)$_2$ is catecholborane. In some embodiments, B(OR)$_2$ is pinacolborane. In some embodiments, B(OR)$_2$ is chosen from boronic acids. In some embodiments, the boronic acid is e.g., isopropylboronic acid, methylboronic acid, or BF3boronic acid. In some embodiments, B(OR)$_2$ is B(OH)$_2$.

In some embodiments, step (b) is performed in the presence of a palladium catalyst. In some embodiments, the palladium catalyst is a Pd(0) or Pd(II) catalyst. In some embodiments, the palladium catalyst is a Pd(0) catalyst. In some embodiments, the palladium catalyst is a Pd(II) catalyst. In some embodiments, the palladium catalyst is PdCl$_2$(dtbpf), PdCl$_2$(dppf), or Pd(OAc)$_2$). In some embodiments, the palladium catalyst is PdCl$_2$(dtbpf). In some embodiments, the palladium catalyst is PdCl$_2$(dppf). In some embodiments, the palladium catalyst is Pd(OAc)$_2$).

In some embodiments, step (c) is performed in the presence of a base. In some embodiments, the base is N,N-diisopropylethylamine, triethylamine, or 1,8-diazabicyclo[5.4.0]undec-7-ene. In some embodiments, the base is N,N-diisopropylethylamine. In some embodiments, the base is triethylamine. In some embodiments, the base is 1,8-diazabicyclo[5.4.0]undec-7-ene.

In some embodiments, step (c) is performed in the presence of a chlorinating sulfur and phosphorous reagent. In some embodiments, the chlorinating sulfur and phosphorous reagent is chosen from phosphorous oxychloride, phosphorous pentachloride, sulfuryl chloride, and trichloromethansulfonyl chloride. In some embodiments, the chlorinating sulfur and phosphorous reagent is phosphorous oxychloride. In some embodiments, the chlorinating sulfur and phosphorous reagent is phosphorous pentachloride. In some embodiments, the chlorinating sulfur and phosphorous reagent is chosen from sulfuryl chloride. In some embodiments, the chlorinating sulfur and phosphorous reagent is trichloromethansulfonyl chloride.

In some embodiments, the (S)-1-(2-(4$\lambda^2$-piperazin-1-yl)pyrimidin-5-yl)-1-(4-fluorophenyl)ethan-1-amine (2) or a pharmaceutically acceptable salt thereof:

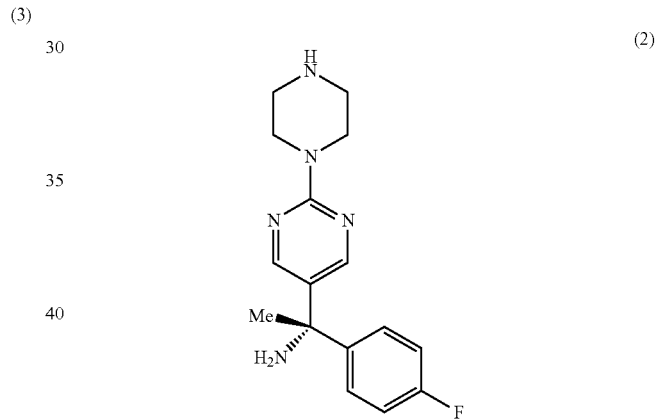
(2)

or a pharmaceutically acceptable salt thereof is prepared by (d) converting a compound of Formula (III):

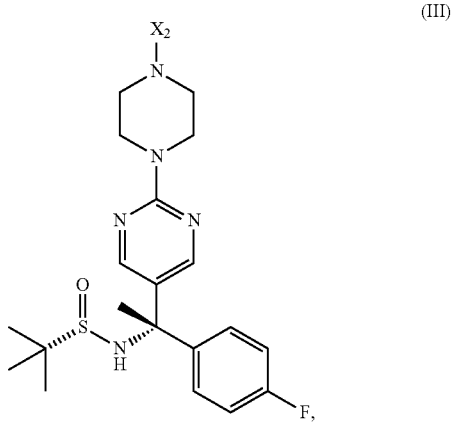
(III)

into (S)-1-(2-(4λ²-piperazin-1-yl)pyrimidin-5-yl)-1-(4-fluorophenyl)ethan-1-amine (2) or a pharmaceutically acceptable salt thereof:

(2)

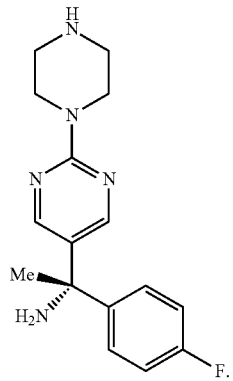

In some embodiments, $X_2$ is chosen from a carbamate protecting group, benzyl, tetrahydropyranyl, acetamide, trifluoroacetamide, triphenylmethylamine, benzylideneamine, and p-toluenesulfonamide. In some embodiments, $X_2$ is benzyl. In some embodiments, $X_2$ is tetrahydropyranyl. In some embodiments, $X_2$ is acetamide. In some embodiments, $X_2$ is trifluoroacetamide. In some embodiments, $X_2$ is triphenylmethylamine. In some embodiments, $X_2$ is benzylideneamine. In some embodiments, $X_2$ is p-toluenesulfonamide. In some embodiments, $X_2$ is a carbamate protecting group. In some embodiments, the carbamate protecting group is tert-butyl carbamate, 9-fluorenylmethyl carbamate, and benzyl carbamate. In some embodiments, $X_2$ is tert-butyl carbamate. In some embodiments, $X_2$ is 9-fluorenylmethyl carbamate. In some embodiments, $X_2$ is benzyl carbamate.

In some embodiments, the pharmaceutically acceptable salt is a hydrochloride salt of (S)-1-(2-(4λ²-piperazin-1-yl)pyrimidin-5-yl)-1-(4-fluorophenyl)ethan-1-amine (2). In some embodiments, the pharmaceutically acceptable salt is (S)-1-(2-(4λ²-piperazin-1-yl)pyrimidin-5-yl)-1-(4-fluorophenyl)ethan-1-amine·3.5 HCl (2A):

(2A)

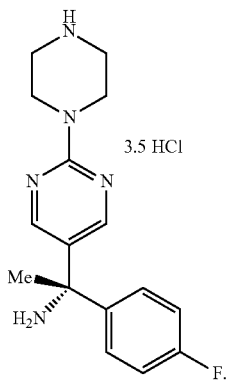

In some embodiments, the pharmaceutically acceptable salt (S)-1-(2-(4λ²-piperazin-1-yl)pyrimidin-5-yl)-1-(4-fluorophenyl)ethan-1-amine·3.5 HCl (2A) is not isolated.

In some embodiments, step (d) is performed in the presence of a first acid. In some embodiments, the first acid is a strong acid. In some embodiments, the first acid is HCl, TFA, or $H_2SO_4$. In some embodiments, the first acid is HCl. In some embodiments, the first acid is TFA. In some embodiments, the first acid is $H_2SO_4$. In some embodiments, the first acid is a Lewis acid. In some embodiments, step (d) is performed in the presence of iodine. In some embodiments, step (d) is performed under thermolytic conditions.

Some embodiments of the present disclosure comprise:
(e) converting a compound of Formula (IV):

(IV)

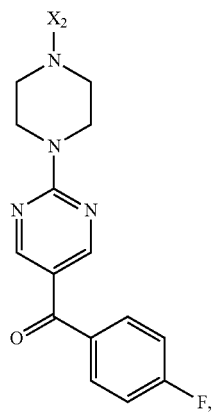

into a compound of Formula (V):

(V)

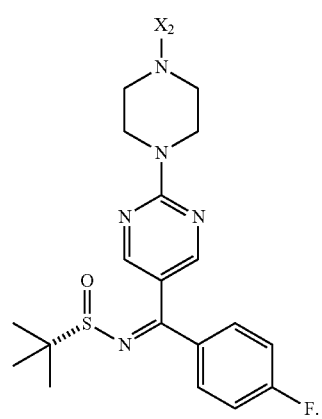

In some embodiments, step (e) is performed in the presence of a catalyst. In some embodiments, the catalyst is titanium isopropoxide, titanium ethoxide, titanium butoxide, or titanium tetrachloride. In some embodiments, the catalyst is titanium isopropoxide. In some embodiments, the catalyst is titanium ethoxide. In some embodiments, the catalyst is titanium butoxide. In some embodiments, the catalyst is titanium tetrachloride. In some embodiments, the catalyst is a Lewis acid. In some embodiments, step (e) is performed in the presence of (S)-2-methylpropane-2-sulfinamide or (S)-p-toluenesulfinamide. In some embodiments, step (e) is performed in the presence of (S)-2-methylpropane-2-sulfinamide. In some embodiments, step (e) is performed in the presence of (S)-p-toluenesulfinamide.

Some embodiments of the present disclosure comprise:
(f) converting the compound of Formula (V):

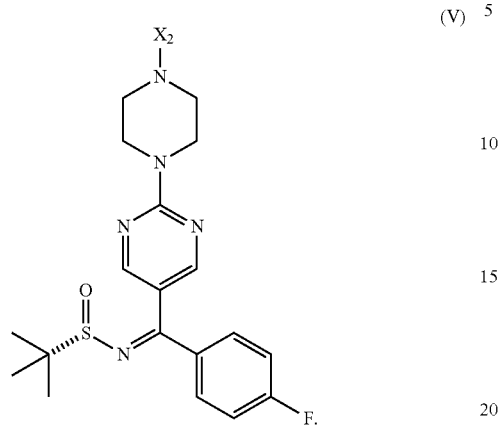

into a compound of Formula (VI):

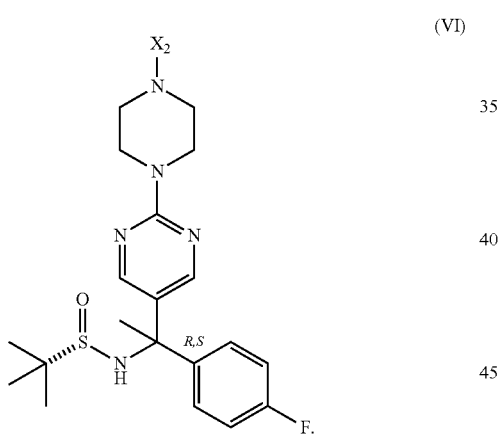

In some embodiments, step (f) is performed in the presence of a Grignard reagent, alkyl halide, or alkyl metal. In some embodiments, step (f) is performed in the presence of a Grignard reagent. In some embodiments, the Grignard reagent is methylmagnesium bromide, methylmagnesium chloride, or methylmagnesium iodide. In some embodiments, the Grignard reagent is methylmagnesium bromide. In some embodiments, the Grignard reagent is methylmagnesium chloride. In some embodiments, the Grignard reagent is methylmagnesium iodide. In some embodiments, step (f) is performed in the presence of an alkyl halide. In some embodiments, step (f) is performed in the presence of an alkyl metal. In some embodiments, step (f) is performed in the presence of 2-methyl tetrahydrofuran.

Some embodiments of the present disclosure comprise:
(g) triturating the compound of Formula (VI):

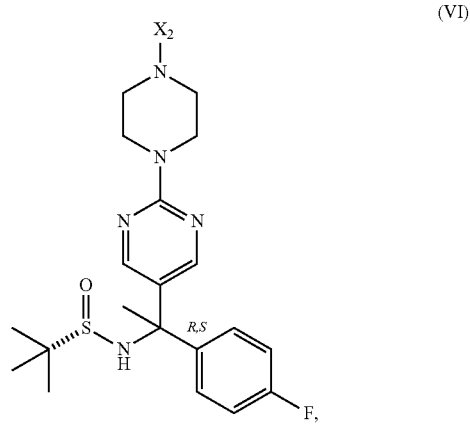

to obtain the compound of Formula (III):

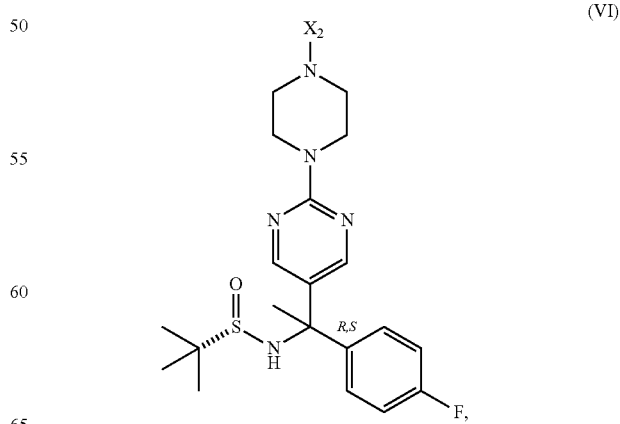

In some embodiments, the trituration solvent in step (g) comprises n-heptane and methanol.

Some embodiments of the present disclosure comprise:
(g) recrystallizating of the compound of Formula (VI):

(VI)

to obtain the compound of Formula (III):

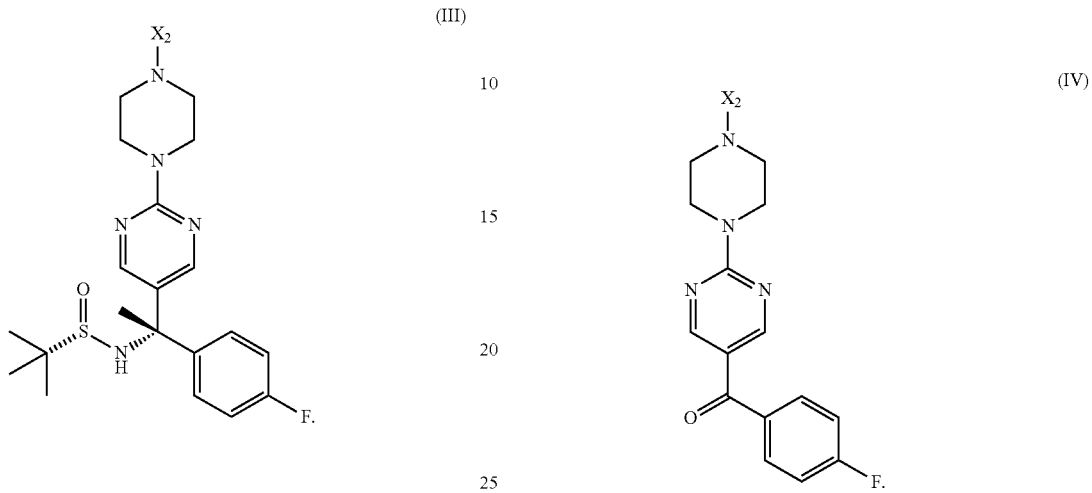

In some embodiments, the recrystallization solvent in step (g) comprises isopropanol. In some embodiments, the recrystallization solvent in step (g) comprises heptane and ethyl acetate.

Some embodiments of the present disclosure comprise:

(h) reacting a compound of Formula (VII):

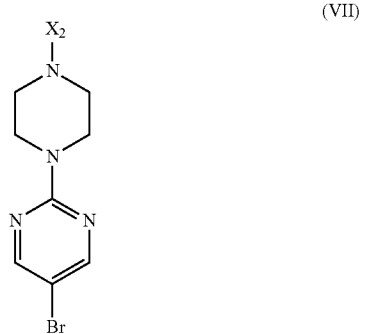

and 4-fluoro-N-methoxy-N-methylbenzamide (12):

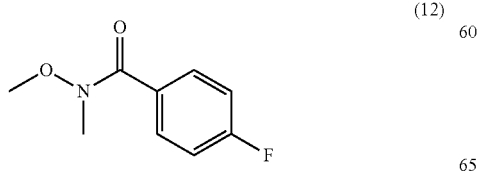

to form the compound of Formula (IV):

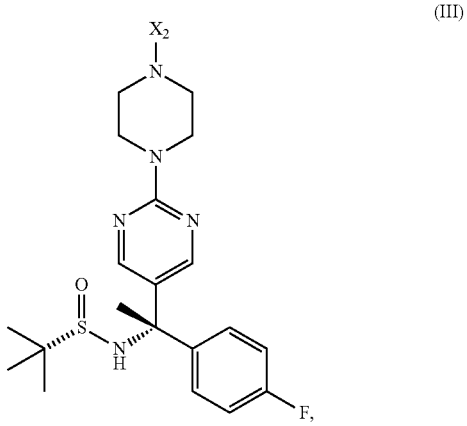

In some embodiments, step (h) is performed in the presence of an organolithium reagent or magnesium powder. In some embodiments, step (h) is performed in the presence of an organolithium reagent. In some embodiments, the organolithium reagent is n-butyllithium, n-hexyllithium, or cyclohexyllithium. In some embodiments, the organolithium reagent is n-butyllithium. In some embodiments, the organolithium reagent is n-hexyllithium. In some embodiments, the organolithium reagent is cyclohexyllithium. In some embodiments, step (h) is performed in the presence of magnesium powder.

In some embodiments, the present disclosure provides a method of preparing a compound (III)

comprising
triturating or recrystallizing a compound of Formula (VI):

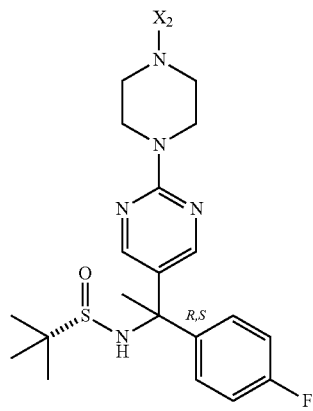

(VI)

to obtain the compound of Formula (III):

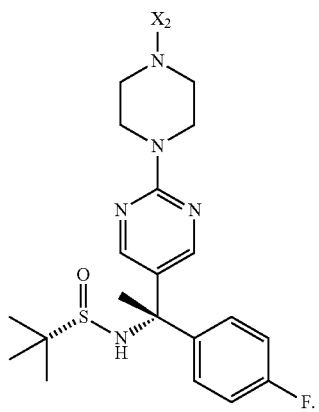

(III)

In some embodiments, $X_2$ is chosen from a carbamate protecting group, benzyl, tetrahydropyranyl, acetamide, trifluoroacetamide, triphenylmethylamine, benzylideneamine, and p-toluenesulfonamide. In some embodiments, $X_2$ is benzyl. In some embodiments, $X_2$ is tetrahydropyranyl. In some embodiments, $X_2$ is acetamide. In some embodiments, $X_2$ is trifluoroacetamide. In some embodiments, $X_2$ is triphenylmethylamine. In some embodiments, $X_2$ is benzylideneamine. In some embodiments, $X_2$ is p-toluenesulfonamide. In some embodiments, $X_2$ is a carbamate protecting group. In some embodiments, the carbamate protecting group is tert-butyl carbamate, 9-fluorenylmethyl carbamate, and benzyl carbamate. In some embodiments, $X_2$ is tert-butyl carbamate. In some embodiments, $X_2$ is 9-fluorenylmethyl carbamate. In some embodiments, $X_2$ is benzyl carbamate.

In some embodiments, the trituration solvent in the step of triturating a compound of Formula (VI) comprises n-heptane and methanol or the recrystallization solvent in the step of recrystallizing a compound of Formula (VI) is isopropanol or heptane/ethyl acetate.

The disclosure provides a process for purifying Compound (I) to remove its undesired enantiomer (Compound (E)). Compound (I) can be crystalline, a mixture of crystalline forms or non-crystalline e.g., an amorphous solid.

Specifically, the disclosure provides a process for the preparation of Compound (I) comprising forming a salt of Compound (I) with D-quinic acid in an organic solvent and crystallizing the salt from a solvent mixture. In some embodiments, the organic solvent is THF. In some embodiments, the solvent mixture is THF and water. In some embodiments, the ratio of the solvent mixture is 20 volumes THF to water. In some embodiments, the process further comprises recrystallizing Compound (I) in acetone and water as described herein.

Indications

Crystalline forms of Compound (I), pharmaceutically acceptable salts thereof, and solvates of any of the foregoing described herein can be useful for treating conditions associated with aberrant KIT activity, in humans or non-humans. Activating mutations in KIT are found in multiple indications, including systemic mastocytosis, gastrointestinal stromal tumors (GIST), acute myeloid leukemia (AML), melanoma, seminoma, intercranial germ cell tumors, and mediastinal B-cell lymphoma.

Mastocytosis refers to a group of disorders characterized by excessive mast cell accumulation in one tissue, or in multiple tissues. Mastocytosis is subdivided into two groups of disorders: (1) cutaneous mastocytosis (CM) describes forms that are limited to the skin; and (2) systemic mastocytosis (SM) describes forms in which mast cells infiltrate extracutaneous organs, with or without skin involvement. Systemic mastocytosis is a rare disease. A cohort study conducted in Denmark estimated the incidence of SM (all subtypes including patients with cutaneous mastocytosis (CM) without documented systemic involvement) as 0.89 per 100,000 per year. Prevalence of ISM in the Groningen region of the Netherlands, a major referral area for SM patients, is estimated at 13/100,000. Mutations in KIT D816 are demonstrated in 90% to 95% of patients with SM.

SM is further subdivided into five forms: indolent (ISM), smoldering (SSM), aggressive (ASM), SM with associated hemotologic non-mast cell lineage disease (SM-AHNMD), and mast cell leukemia (MCL). The term "advanced systemic mastocytosis" (Adv-SM) refers to ASM, SM-AHNMD, and MCL. The term "non-advanced systemic mastocytosis" (non-Adv SM) refers to ISM and SSM.

Diagnosis of systemic mastocytosis is based in part on histological and cytological studies of bone marrow showing infiltration by mast cells of frequently atypical morphology, which frequently abnormally express non-mast cell markers (CD25 and/or CD2). Diagnosis of SM is confirmed when bone marrow mast cell infiltration occurs in the context of one of the following: (1) abnormal mast cell morphology (spindle-shaped cells); (2) elevated level of serum tryptase above 20 ng/mL; or (3) the presence of the activating KIT D816V mutation.

Activating mutations at the D816 position are found in most mastocytosis cases (90%-98%), with the most common mutations being D816V, D816H, and D816Y. The D816V mutation is found in the activation loop of the kinase domain and leads to constitutive activation of KIT kinase.

There are no approved treatments for ISM and SSM; symptoms are managed with symptom-directed therapies, such as antihistamines. Thus, there is a need for safe, effective treatments for ISM and SSM. Furthermore, since ISM and SSM patients have lower disease burden than AdvSM patients and are expected to remain on treatment for long periods of time, there is a need for low doses, if efficacious.

Crystalline forms of Compound (I), pharmaceutically acceptable salts thereof, and solvates of any of the foregoing may also be useful to treat GIST, e.g., PDGFRα-exon 18 mutant driven GIST, PDGFRα-exon 18 D842 driven GIST (e.g., PDGFRα-D842I driven GIST, PDGFRα-D842V driven GIST, or PDGFRα-D842Y driven GIST), PDGFRα-exon 18 mutant non-D842 driven GIST (e.g., PDGFRα-D842-H845 driven GIST, PDGFR(X-DI842-843V driven GIST), regardless of prior therapy. Approximately 90% of patients with GIST have a tumor that is dependent on a mutation in either V-kit Hardy-Zuckerman 4 feline sarcoma viral oncogene homolog (KIT) (75%-80%) or the highly related protein platelet-derived growth factor receptor alpha (PDGFRα) (10%-15%). On a molecular level, the most common sites for oncogenic mutations at the time of diagnosis are in the juxtamembrane domain (exon 11 [60%-70%]) and extracellular domain (exon 9 [5%-15%]) for KIT and in the activation loop (Exon 18) for PDGFRα where the most common activation loop mutation is D842V.

Complete surgical resection remains the principal treatment of choice for patients with a primary GIST. GIST is not considered sensitive to either systemic cytotoxic chemotherapy or radiation therapy. Surgery is effective in approximately 50% of patients with GIST. For the remaining patients, tumor recurrence is frequent. Primary treatment with a KIT inhibitor such as imatinib has also been shown to be sufficient for initial treatment of GIST. However, resistance to imatinib occurs in GIST patients within months through somatic mutation in KIT that markedly decreases the binding affinity of imatinib. These resistance mutations invariably arise within the ATP-binding pocket (exons 13 and 14) or the activation loop (exons 17 and 18) of the kinase. None of the currently approved therapeutics for treating GIST is a selective targeted agent. Rather, the currently approved agents for the treatment of GIST after imatinib are multikinase inhibitors, e.g., sunitinib, regorafenib, and midostaurin. In many cases, these multikinase inhibitors only weakly inhibit imatinib resistant mutants. Additionally, multikinase inhibitors may be of limited therapeutic value due to a more complex safety profile and a small therapeutic window. Thus, there is a need for therapeutic agents to treat GIST patients who are resistant to imatinib.

There is a subset of patients with unresectable or metastatic GIST who have been treated with at least three lines of prior therapy. The compounds described herein may be useful in treating these patients.

In addition to the use of the crystalline forms of Compound (I), pharmaceutically acceptable salts thereof, and solvates of any of the foregoing described herein as agents in the refractory GIST setting, the use of combinations of imatinib, sunitinib, and/or regorafenib with at least one crystalline form chosen from crystalline forms of Compound (I), pharmaceutically acceptable salts thereof, and solvates of any of the foregoing disclosed herein may allow for the prevention of emergence of resistance to exon 17 mutations.

There is a subset of GIST patients with alterations in the activation loop of PDGFRα. There is a subset of GIST patients with point mutations in the activation loop of PDGFRα. There is a subset of GIST patients with a D842V mutation in PDGFRα; this subgroup of GIST patients can be stratified by identifying this mutation. This subset of patients is refractory to all tyrosine kinase inhibitors currently available. The compounds described herein, due to their selective activity against PDGFRα D842V, may be useful in treating these patients.

Mutation of the aspartic acid (D) residue at position 842 of exon 18 of PDGFRα to isoleucine (I) or tyrosine (Y) results in ligand-independent, constitutive activation of PDGFRα tyrosine kinase activity. There is also a subset of GIST patients with a D842I mutation in PDGFRα; this subgroup of GIST patients can be stratified by identifying this mutation. The compounds described herein, due to their selective activity against PDGFRα D842I, may be useful in treating these patients. Furthermore, there is a subset of GIST patients with a D842Y mutation in PDGFRα; this subgroup of GIST patients can be stratified by identifying this mutation. The compounds described herein, due to their selective activity against PDGFRα D842Y, may be useful in treating these patients.

There is a subset of GIST patients with indels in the activation loop of PDGFRα. There is a subset of GIST patients with alteration D842-H845 in PDGFRα; this subgroup of GIST patients can be stratified by identifying this alteration. The compounds described herein, due to their selective activity against PDGFRα, D842-H845 in PDGFRα, may be useful in treating these patients.

There is a subset of GIST patients with alteration DI842-843V in PDGFRα; this subgroup of GIST patients can be stratified by identifying this alteration. The compounds described herein, due to their selective activity against PDGFRα D1842-843V in PDGFRα may be useful in treating these patients.

Crystalline forms of Compound (I), pharmaceutically acceptable salts thereof, and solvates of any of the foregoing described herein may also be useful in treating AML. AML patients also harbor KIT mutations, with the majority of KIT mutations occurring at the D816 position.

In addition, mutations in KIT have been linked to Ewing's sarcoma, DLBCL (diffuse large B cell lymphoma), dysgerminoma, MDS (myelodysplastic syndrome), NKTCL (nasal NK/T-cell lymphoma), CMML (chronic myelomonocytic leukemia), and brain cancers.

Crystalline forms of Compound (I), pharmaceutically acceptable salts thereof, and solvates of any of the foregoing disclosed herein may be used to treat conditions associated with the KIT genetic mutations in Exon 9, Exon 11, Exon 13, Exon 14, Exon 17, and/or Exon 18. The crystalline forms may also be used to treat conditions associated with wild-type KIT. Crystalline forms of Compound (I), pharmaceutically acceptable salts thereof, and solvates of any of the foregoing herein may be used as agents to treat the conditions described herein, or they may be used in combination with other therapeutic agents, including, without limitation, imatinib, sunitinib and regorafenib. Other agents include the compounds described in WO 2014/039714 and WO 2014/100620.

Crystalline forms of Compound (I), pharmaceutically acceptable salts thereof, and solvates of any of the foregoing described herein can be active against at least one KIT mutation in exon 11, 11/17 and exon 17 (e.g., d557-558, V560G, V560G/D816V, V560G/N822K, D816E, D816F, D816H, D816I, D816V, D816Y, D816K, D816H, D816A, D816G, D820A, D820E, D802Y, D820G, N822K, N822H, Y823D, and/or A829P), and much less active against wild-type KIT. In some emodiments, crystalline forms of Compound (I), pharmaceutically acceptable salts thereof, and solvates of any of the foregoing herein can be active against at least one KIT mutation exon 11, 11/17 and 17 mutants (d557-558, V560G, V560G/D816V, V560G/N822K, D816E, D816F, D816H, D816I, D816V, D816Y, D820E, D820Y and Y823D).

The crystalline forms can be administered in combination with an agent that is (a) active against other activating mutations of KIT, such as Exon 9 and 11 mutations, but (b) not active against the Exon 17 mutations. Such agents include imatinib, sunitinib, and regorafenib. The combination of at least one crystalline form chosen from crystalline forms of Compound (I), pharmaceutically acceptable salts thereof, and solvates of any of the foregoing, and the agent will thus inhibit Exon 17 mutant KIT, as well as inhibiting Exon 9/11 mutant KIT. The at least one crystalline form and the agent can be co-administered or administered in an alternating regimen. That is, the Exon 17 mutant KIT inhibitor can be administered alone for a period of time; then the Exon 9/11 mutant KIT inhibitor can be administered alone for a period of time following. This cycle may then be repeated. It is believed that such a regimen could slow the development of resistance to the Exon 17 mutant KIT inhibitor and/or the Exon 9/11 mutant KIT inhibitor.

In addition, the at least one crystalline form chosen from crystalline forms of Compound (I), pharmaceutically acceptable salts thereof, and solvates of any of the foregoing described herein that can be selective for Exon 17 KIT mutations can be administered with at least one agent active against Exon 9/11 mutations in combination with a third agent that covers mutations that are missed with the two-way combo. The combination of the three agents could inhibit a spectrum of KIT mutations, as well as wild-type KIT in some instances. The agents could be administered simultaneously or in an alternating regimen. They can be administered one at a time, or two agents can be administered together for a period of time; then the third agent can be administered alone for a following period of time. It is believed that such a regimen could slow the development of resistance to the mutant KIT inhibitors.

In some embodiments, the at least one crystalline form chosen from crystalline forms of Compound (I), pharmaceutically acceptable salts thereof, and solvates of any of the foregoing may be used as alone or in combination with imatinib, sunitinib, and/or regorafenib.

In some embodiments, the at least one crystalline form chosen from crystalline forms of Compound (I), pharmaceutically acceptable salts thereof, and solvates of any of the foregoing may be used in conjunction with other treatment modalities such as, for example, surgery or radiation therapy.

Dosing

The effective dose for any particular patient or subject will depend upon a variety of factors including: the disorder being treated and the severity of the disorder; the specific pharmaceutical composition employed; the age, body weight, general health, sex and diet of the patient or subject; the time of administration, route of administration, the duration of the treatment; and like factors well known in the medical arts.

In some embodiments, a therapeutically effective amount of at least one crystalline form chosen from crystalline forms of Compound (I), pharmaceutically acceptable salts thereof, and solvates of any of the foregoing (e.g., crystalline Form A of Compound (I)) is administered to a patient in need thereof. In some embodiments, a therapeutically effective amount of at least one crystalline form chosen from crystalline forms of Compound (I), pharmaceutically acceptable salts thereof, and solvates of any of the foregoing (e.g., crystalline Form A of Compound (I)) is administered to a patient in need thereof once daily.

In some embodiments, the therapeutically effective amount of the at least one crystalline form administered to the patient once daily is an amount ranging from 25 mg to 400 mg (e.g., 25 mg, 30 mg, 40, mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, or 400 mg) of a crystalline form of Compound (I) (e.g., crystalline Form A of Compound (I), crystalline Form B of Compound (I), or crystalline Form O of Compound (I)) or the weight equivalent of a crystalline form of a pharmaceutically acceptable salt thereof (e.g., crystalline Form T of a tosylate salt of Compound (I), crystalline Form Tr of a tartrate salt of Compound (I), or crystalline Form H of a hydrochloride salt of Compound (I)) or the weight equivalent of a crystalline form of a solvate of Compound (I) or a pharmaceutically acceptable salt thereof (e.g., crystalline Form C of Compound (I)).

The disclosure provides improved methods for treating Adv SM in patients in need thereof by administering crystalline forms of Compound (I) and/or a pharmaceutically acceptable salt thereof. In some embodiments, the therapeutically effective amount of the at least one crystalline form administered to the patient once daily is an amount ranging from 200 mg to 300 mg (e.g., 200 mg, 225 mg, 250 mg, or 300 mg) of a crystalline form of Compound (I) (e.g., crystalline Form A of Compound (I), crystalline Form B of Compound (I), or crystalline Form O of Compound (I)) or the weight equivalent of a crystalline form of a pharmaceutically acceptable salt thereof (e.g., crystalline Form T of a tosylate salt of Compound (I), crystalline Form Tr of a tartrate salt of Compound (I), or crystalline Form H of a hydrochloride salt of Compound (I)) or the weight equivalent of a crystalline form of a solvate of Compound (I) or a pharmaceutically acceptable salt thereof (e.g., crystalline Form C of Compound (I)). In some embodiments, the patient is suffering from advanced systemic mastocytosis (e.g., ASM, SM-AHN, or MCL) and the therapeutically effective amount of crystalline Form A of Compound (I) is 200 mg to 300 mg administered once daily. In some embodiments, the patient is suffering from advanced systemic mastocytosis (e.g., ASM, SM-AHN, or MCL) and the therapeutically effective amount of crystalline Form A of Compound (I) is 200 mg administered once daily. In some embodiments, the patient is suffering from advanced systemic mastocytosis (e.g., ASM, SM-AHN, or MCL) and the therapeutically effective amount of crystalline Form A of Compound (I) is 300 mg administered once daily.

The disclosure provides improved methods for treating GIST in patients in need thereof by administering crystalline forms of Compound (I) and/or a pharmaceutically acceptable salt thereof. In some embodiments, the therapeutically effective amount of the at least one crystalline form administered to the patient once daily is an amount ranging from 300 mg to 400 mg (e.g., 325 mg, 350 mg, 375 mg, or 400 mg) of a crystalline form of Compound (I) (e.g., crystalline Form A of Compound (I), crystalline Form B of Compound (I), or crystalline Form O of Compound (I)) or the weight equivalent of a crystalline form of a pharmaceutically acceptable salt thereof (e.g., crystalline Form T of a tosylate salt of Compound (I), crystalline Form Tr of a tartrate salt of Compound (I), or crystalline Form H of a hydrochloride salt of Compound (I)) or the weight equivalent of a crystalline form of a solvate of Compound (I) or a pharmaceutically acceptable salt thereof (e.g., crystalline Form C of Compound (I)). In some embodiments, the patient is suffering from gastrointestinal stromal tumor and the therapeutically effective amount of crystalline Form A of Compound (I) is 300 mg to 400 mg administered once daily. In some embodiments, the patient is suffering from GIST and the therapeutically effective amount of crystalline Form A of Compound (I) is 300 mg administered once daily. In some embodiments, the patient is suffering from GIST and the therapeutically effective amount of crystalline Form A of Compound (I) is 400 mg administered once daily. If 300 mg once daily of crystalline Form A of Compound (I) is well-tolerated by the patient, the dose can be increased to 400 mg once daily. If 300 mg once daily of crystalline Form A of Compound (I) is well-tolerated by the patient for at least two consecutive treatment cycles (28 days each), for at least three consecutive treatment cycles (28 days each), or for at least four consecutive treatment cycles (28 days each), the dose can be increased to 400 mg once daily.

The disclosure provides improved methods for treating indolent systemic mastocytosis (ISM) and smoldering systemic mastocytosis (SSM) in patients in need thereof by administering Compound (I) and/or a pharmaceutically acceptable salt thereof. Specifically, the disclosure provides safe and effective dosing regimens of Compound (I) that can be used for long-term treatment. In one aspect, the ISM or SSM patient in need thereof has moderate-to-severe symptoms.

According to the latest clinical study as shown in the Example 13, it has now been found that 25 mg of Compound (I) dosed once daily in patients with ISM or SSM shows improvement across all three aspects of its clinical profile, including reduction in mast cell burden, improvement of disease symptoms, and improvement in quality of life. Specifically, 25 mg of Compound (I) dosed once daily has a statistically significant reduction in ISM-SAF TSS and each symptom in the total domain score at 16 weeks. Surprisingly, the 25 mg dose provided similar mean improvements in TSS as the higher doses of 50 mg and 100 mg and better tolerability. For example, similar to the 50 mg QD dose and 100 mg QD dose, the 25 mg QD dose shows significant reduction in blood KIT D816V allele fraction. Moreover, 25 mg of Compound (I) dosed once daily in patients has a favorable safety profile in patients with ISM. For example, 95% of patients remain on the clinical study, with no discontinuations for adverse effects (AEs). No grade≥3 AEs occurred in the 25 mg once daily cohort. Patients have improvements in quality of life (QoL), as measured by MC-QoL overall score and all domain scores, at week 16.

The disclosure provides improved methods for treating ISM and SSM in patients in need thereof by administering crystalline forms of Compound (I) and/or a pharmaceutically acceptable salt thereof. In some embodiments, the therapeutically effective amount of the at least one crystalline form administered to the patient once daily is an amount ranging from 25 mg to 100 mg (e.g., 25, 50, or 100 mg) of a crystalline form of Compound (I) (e.g., crystalline Form A of Compound (I), crystalline Form B of Compound (I), or crystalline Form O of Compound (I)) or the weight equivalent of a crystalline form of a pharmaceutically acceptable salt thereof (e.g., crystalline Form T of a tosylate salt of Compound (I), crystalline Form Tr of a tartrate salt of Compound (I), or crystalline Form H of a hydrochloride salt of Compound (I)) or the weight equivalent of a crystalline form of a solvate of Compound (I) or a pharmaceutically acceptable salt thereof (e.g., crystalline Form C of Compound (I)). In some embodiments, the patient is suffering from indolent or smoldering systemic mastocytosis and the therapeutically effective amount of crystalline Form A of Compound (I) is 25 mg to 100 mg administered once daily. In some embodiments, the patient is suffering from indolent or smoldering systemic mastocytosis and the therapeutically effective amount of crystalline Form A of Compound (I) is 25 mg administered once daily. In some embodiments, the patient is suffering from indolent or smoldering systemic mastocytosis and the therapeutically effective amount of crystalline Form A of Compound (I) is 50 mg administered once daily. In some embodiments, the patient is suffering from indolent or smoldering systemic mastocytosis and the therapeutically effective amount of crystalline Form A of Compound (I) is 100 mg administered once daily.

The disclosure provides a method of treating indolent systemic mastocytosis (ISM) or smoldering systemic mastocytosis (SSM) comprising administering to a patient in need thereof an amount of 10 mg to 100 mg of Compound (I) or a pharmaceutically acceptable salt thereof in an amount equivalent to 10 mg to 100 mg of Compound (I), once a day. In some embodiments, the patient in need thereof is administered an amount of 10 mg to 100 mg of Compound (I) once a day. In some embodiments, the patient in need thereof is administered an amount of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg of Compound (I) (or a pharmaceutically acceptable salt thereof in an amount equivalent to 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg of Compound (I)) once a day. In some embodiments, the amount is from 10 mg to 25 mg once a day. In some embodiments, the amount is from 10 mg to 50 mg once a day. In some embodiments, the amount is from 10 mg to 75 mg once a day. In some embodiments, the amount is from 10 mg to 100 mg once a day. In some embodiments, the amount is from 25 mg to 50 mg once a day. In some embodiments, the amount is from 25 mg to 100 mg once a day. In some embodiments, the amount is from 50 mg to 100 mg once a day. In some embodiments, the amount is from 75 mg to 100 mg once a day. In some embodiments, the amount is 10 mg once a day. In some embodiments, the amount is 15 mg once a day. In some embodiments, the amount is 20 mg once a day. In some embodiments, the amount is 25 mg once a day. In some embodiments, the amount is 30 mg once a day. In some embodiments, the amount is 35 mg once a day. In some embodiments, the amount is 35 mg once a day. In some embodiments, the amount is 40 mg once a day. In some embodiments, the amount is 45 mg once a day. In some embodiments, the amount is 50 mg once a day. In some embodiments, the amount is 55 mg once a day. In some embodiments, the amount is 60 mg once a day. In some embodiments, the amount is 65 mg once a day. In some embodiments, the amount is 70 mg once a day. In some embodiments, the amount is 75 mg once a day. In some embodiments, the amount is 80 mg once a day. In some embodiments, the amount is 85 mg once a day. In some embodiments, the amount is 90 mg once a day. In some embodiments, the amount is 95 mg once a day. In some embodiments, the amount is 100 mg once a day.

In some embodiments, the at least one crystalline form chosen from crystalline forms of Compound (I), pharmaceutically acceptable salts thereof, and solvates of any of the foregoing disclosed herein is administered orally. In some embodiments, the at least one crystalline form chosen from crystalline forms of Compound (I), pharmaceutically acceptable salts thereof, and solvates of any of the foregoing disclosed herein is administered until disease progression, unacceptable toxicity, or individual choice.

In clinical trials employing crystalline Form A of Compound (I), adverse effects were categorized by severity into Grades 1-5. Most adverse events reported were Grade 1 or 2, indicating crystalline Form A of Compound (I) is well-tolerated. Patients administered crystalline Form A of Compound (I) did not exhibit the severe dose limiting toxicities observed for other tyrosine kinase inhibitors (TKIs) such as dermatologic, hepatic, and cardiovascular toxicities. Severe dose limiting toxicities for other TKIs may be a result of inhibiting a broad range of kinases.

Pharmaceutical Compositions

The crystalline forms described herein are useful as active pharmaceutical ingredients (APIs) as well as materials for preparing pharmaceutical compositions that incorporate one or more pharmaceutically acceptable excipients and are suitable for administration to human subjets. In some embodiments, these pharmaceutical compositions will be a pharmaceutical product, such as, for example, a solid oral dosage form, such as tablets and/or capsules. In the preparation of these pharmaceutical compositions, the crystalline form of (S)-1-(4-fluorophenyl)-1-(2-(4-(6-(1-methyl-H-pyrazol-4-yl)pyrrolo[2,1-f][1,2,4]triazin-4-yl)piperazin-yl)pyrimidin-5-yl)ethan-1-amine may not be detectable in any sufficient amount. For example, the crystalline form may not be detectable where a crystalline API is contacted with one or more pharmaceutically acceptable excipients in the presence of a solvent, such as, for example, water, in an amount sufficient to promote dissolution of the API, e.g., such that its crystalline character is lost and therefore is absent in the final pharmaceutical product.

In some embodiments, crystalline (S)-1-(4-fluorophenyl)-1-(2-(4-(6-(1-methyl-1H-pyrazol-4-yl)pyrrolo [2,1-f][1,2,4] triazin-4-yl)piperazin-yl)pyrimidin-5-yl)ethan-1-amine may be used in a process to prepare a pharmaceutical composition that, for example, involves spray drying or wet granulation. Where the process involves spray drying or wet granulation, little to no crystalline form will likely be detected in the resulting pharmaceutical composition.

In some embodiments, the present disclosure provides a pharmaceutical composition consisting of at least one crystalline form chosen from crystalline forms of Compound (I), pharmaceutically acceptable salts thereof, and solvates of any of the foregoing.

In some embodiments, the present disclosure provides a pharmaceutical composition comprising at least one crystalline form chosen from crystalline forms of Compound (I), pharmaceutically acceptable salts thereof, and solvates of any of the foregoing. For example, crystalline Form A of Compound (I), crystalline Form B of Compound (I), crystalline Form C of Compound (I), crystalline Form O of Compound (I), crystalline Form T of a tosylate salt of Compound (I), crystalline Form Tr of a tartrate salt of Compound (I), and/or crystalline Form H of a hydrochloride salt of Compound (I) may be formulated in a pharmaceutical composition for administration in any convenient way for use in human or veterinary medicine.

In some embodiments, the present disclosure provides a pharmaceutical composition comprising at least one crystalline form chosen from crystalline forms of Compound (I), pharmaceutically acceptable salts thereof, and solvates of any of the foregoing and at least one additional pharmaceutically acceptable excipient. The term "pharmaceutically acceptable excipient," as used herein, refers to a pharmaceutically acceptable material, composition, and/or vehicle, such as a liquid or solid filler, diluent, excipient, solvent, or encapsulating material. Each excipient must be "pharmaceutically acceptable" in the sense of being compatible with the subject composition and its components and not injurious to the patient. Except insofar as any conventional pharmaceutically acceptable excipient is incompatible with Compound (I) and/or crystalline forms of Compound (I), pharmaceutically acceptable salts thereof, and solvates of any of the foregoing, such as by producing any undesirable biological effect or otherwise interacting in a deleterious manner with any other component(s) of the pharmaceutically acceptable composition, its use is contemplated to be within the scope of this disclosure.

Some non-limiting examples of materials which may serve as pharmaceutically acceptable excipients include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, also discloses additional non-limiting examples of pharmaceutically acceptable excipients, as well as known techniques for preparing and using the same.

Pharmaceutical compositions disclosed herein may be administered orally, parenterally, by inhalation spray, topically, rectally, nasally, buccally, vaginally, or via an implanted reservoir. The term "parenteral," as used herein includes subcutaneous, intravenous, intramuscular, intra-articular, intra-synovial, intrasternal, intrathecal, intrahepatic, intralesional, and intracranial injection or infusion techniques. In some embodiments, the compositions of the disclosure are administered orally, intraperitoneally, or intravenously. Sterile injectable forms of the pharmaceutical compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans, and other emulsifying agents or bioavailability enhancers which are commonly used in the manufacture of pharmaceutically acceptable solid, liquid, or other dosage forms may also be used for the purposes of formulation.

Pharmaceutical compositions disclosed herein may also be orally administered in any orally acceptable dosage form including, but not limited to, capsules, tablets, aqueous suspensions, or solutions. When aqueous suspensions are required for oral use, the active ingredient is typically combined with emulsifying and suspending agents. If desired, certain sweetening, flavoring, or coloring agents may also be added.

Alternatively, pharmaceutical compositions disclosed herein may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax, and polyethylene glycols.

The pharmaceutical compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in at least one excipient. Excipients for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, pharmaceutical compositions disclosed herein can be formulated in a suitable lotion or cream containing the active components suspended or dissolved in at least one pharmaceutically acceptable excipient. Suitable excipients include, but are not limited to, mineral oil, sorbitan monostearate, polysorbate 60, cetyl esters wax, cetearyl alcohol, 2-octyldodecanol, benzyl alcohol, and water.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, the disclosure provides a pharmaceutical composition comprising: at least one pharmaceutically acceptable excipient; and at least one crystalline form chosen from crystalline forms of Compound (I), pharmaceutically acceptable salts thereof, and solvates of any of the foregoing.

In some embodiments, pharmaceutical compositions disclosed herein comprise an intragranular portion and an extragranular portion. In some embodiments, the pharmaceutical compositions disclosed herein comprise at least one filler, at least one disintegrant, and at least one lubricant. As used herein, an "extragranular filler," "extragranular disintegrant," or "extragranular lubricant" refers to a filler, disintegrant, or lubricant, respectively, that comprises an extragranular portion of a pharmaceutical composition.

Fillers suitable for the pharmaceutical compositions disclosed herein are compatible with the other ingredients of the pharmaceutical compositions, i.e., they do not substantially reduce the solubility, the hardness, the chemical stability, the physical stability, or the biological activity of the pharmaceutical compositions. Non-limiting examples of suitable fillers include celluloses, modified celluloses, (e.g. sodium carboxymethyl cellulose, ethyl cellulose hydroxymethyl cellulose, hydroxypropylcellulose), cellulose acetate, microcrystalline cellulose, calcium phosphates, dibasic calcium phosphate, starches (e.g. corn starch, potato starch), sugars (e.g., mannitol, lactose, sucrose, or the like), or any combination thereof. In some embodiments, the filler is microcrystalline cellulose.

In some embodiments, the pharmaceutical composition comprises at least one extragranular filler in an amount of 15 wt % to 20 wt % (e.g., 15 wt %, 15.5 wt %, 16 wt %, 16.5 wt %, 17%, 17.5 wt %, 18 wt %, 18.5 wt %, 19 wt %, 19.5 wt %, or 20 wt %) by weight of the pharmaceutical composition. For example, in some embodiments, the pharmaceutical composition comprises 15 wt % to 20 wt % (e.g., 15 wt %, 15.5 wt %, 16 wt %, 16.5 wt %, 17%, 17.5 wt %, 18 wt %, 18.5 wt %, 19 wt %, 19.5 wt %, or 20 wt %) extragranular microcrystalline cellulose, for example MCC Avicel PH-200, by weight of the pharmaceutical composition. In some embodiments, the pharmaceutical composition comprises 17 wt % extragranular microcrystalline cellulose, for example MCC Avicel PH-200, by weight of the pharmaceutical composition. In some embodiments, the pharmaceutical composition comprises 17 wt % extragranular Avicel PH-200, by weight of the pharmaceutical composition.

Disintegrants suitable for the pharmaceutical compositions disclosed herein can enhance the dispersal of the pharmaceutical compositions and are compatible with the other ingredients of the pharmaceutical compositions, i.e., they do not substantially reduce the chemical stability, the physical stability, the hardness, or the biological activity of the pharmaceutical compositions. Non-limiting examples of suitable disintegrants include croscarmellose sodium, sodium starch glycolate, crospovidone, or any combination thereof. In some embodiments, the disintegrant is croscarmellose sodium. In some embodiments, the disintegrant is Ac-Di-Sol.

In some embodiments, the pharmaceutical compositions disclosed herein comprise extragranular disintegrant in an amount of 2 wt % to 3 wt % (e.g., 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %) by weight of the pharmaceutical composition. For example, in some embodiments, the pharmaceutical compositions comprise 2 wt % to 3 wt % (e.g., 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %) extragranular croscarmellose sodium, e.g., Ac-Di-Sol, by weight of the pharmaceutical composition. In some embodiments, the pharmaceutical compositions comprise 2.5 wt % extragranular croscarmellose sodium, e.g., Ac-Di-Sol, by weight of the pharmaceutical composition. In some embodiments, the pharmaceutical compositions comprise 2.5 wt % extragranular Ac-Di-Sol by weight of the pharmaceutical composition.

In some embodiments, the pharmaceutical compositions disclosed herein comprise a lubricant. A lubricant can prevent adhesion of a mixture component to a surface (e.g., a surface of a mixing bowl, a granulation roll, a compression die, and/or punch). A lubricant can also reduce interparticle friction within the granulate and improve the compression and ejection of compressed pharmaceutical compositions from a granulator and/or die press. A suitable lubricant for the pharmaceutical compositions disclosed herein is compatible with the other ingredients of the pharmaceutical compositions, i.e., they do not substantially reduce the solubility, the hardness, or the biological activity of the pharmaceutical compositions. Non-limiting examples of suitable lubricants include magnesium stearate, sodium stearyl fumarate, calcium stearate, zinc stearate, sodium stearate, stearic acid, aluminum stearate, leucine, glyceryl behenate, hydrogenated vegetable oil, or any combination thereof. In some embodiments, the lubricant is magnesium stearate.

In some embodiments, the pharmaceutical compositions comprise an extragranular lubricant in an amount of 0.25 wt % to 1 wt % (e.g., 0.25 wt %, 0.3 wt %, 0.35 wt %, 0.4 wt %, 0.45 wt %, 0.5 wt %, 0.55 wt %, 0.6 wt %, 0.65 wt %, 0.7 wt %, 0.75 wt %, 0.8 wt %, 0.85 wt %, 0.9 wt %, 0.95 wt %, 1 wt %) by weight of the pharmaceutical composition. For example, in some embodiments, the pharmaceutical compositions comprise 0.25 wt % to 1 wt % (e.g., 0.25 wt %, 0.3 wt %, 0.35 wt %, 0.4 wt %, 0.45 wt %, 0.5 wt %, 0.55 wt %, 0.6 wt %, 0.65 wt %, 0.7 wt %, 0.75 wt %, 0.8 wt %, 0.85 wt %, 0.9 wt %, 0.95 wt %, 1 wt %) extragranular magnesium stearate, by weight of the pharmaceutical composition.

In some embodiments, the pharmaceutical compositions disclosed herein are in the form of a tablet. Tablets disclosed herein can be produced by compacting or compressing an admixture or composition, for example, powder or granules, under pressure to form a stable three-dimensional shape. As used herein, a "tablet" refers to a compressed pharmaceutical dosage unit forms any shape or size, whether coated or uncoated. In some embodiments, tablets disclosed herein comprise an intragranular portion and an extragranular portion.

In some embodiments, methods of preparing the tablets disclosed herein comprise: (a) mixing at least one crystalline form chosen from crystalline forms of Compound (I), pharmaceutically acceptable salts thereof, and solvates of any of the foregoing, at least one first filler, at least one binder, at least one first disintegrant, and at least one first lubricant (intra-granular mixture); (b) granulating the intra-granular mixture (granulated mixture); (c) mixing at least one second filler, at least one second disintegrant, and at least one second lubricant (extra-granular mixture); (d) mixing the granulated mixture and the extra-granular mixture to form a tablet mixture; and (e) compressing the tablet mixture comprising the granulated mixture and the extra-granular mixture into a tablet. Steps (a), (b), and (c) may occur in any order. Any suitable methods known in the art for granulation and compression of pharmaceutical compositions can be used.

Binders suitable for the pharmaceutical compositions, e.g., tablets, disclosed herein can enhance the cohesion and/or tensile strength of the pharmaceutical compositions, e.g., tablets, and are compatible with the other ingredients of the pharmaceutical compositions, i.e., they do not substantially reduce the chemical stability, the physical stability, the hardness, or the biological activity of the pharmaceutical compositions. Non-limiting examples of suitable binders include copovidone, dibasic calcium phosphate, sucrose, corn (maize) starch, microcrystalline cellulose, and modified cellulose (e.g., hydroxymethyl cellulose). In some embodiments, the binder is copovidone. In some embodiments, the binder is Kollidon VA 64 Fine.

In some embodiments, the methods disclosed herein further comprise coating the tablet. Tablets disclosed herein can be coated with a film coating, waxed, and optionally labeled with a logo, other image and/or text using a suitable ink. Suitable film coatings and inks are compatible with the other ingredients of the tablets, e.g., they do not substantially reduce the solubility, the chemical stability, the physical stability, the hardness, or the biological activity of the tablets.

In some embodiments, tablets disclosed herein are coated with a film. In some embodiments, the film comprises at least one colorant and/or pigment. In some embodiments, the film is Opadry II.

In some embodiments, tablets disclosed herein can be coated with a film coating, e.g., Opadry II, and optionally labeled with a logo, other image and/or text using a suitable ink.

In some embodiments, the at least one crystalline form chosen from crystalline forms of Compound (I), pharmaceutically acceptable salts thereof, and solvates of any of the foregoing is in the form of particles.

In some embodiments, tablets described herein comprise granules comprising 30-50 wt % particles of at least one crystalline form of Compound (I) or an equivalent amount of particles of a pharmaceutically acceptable salt thereof or a solvate of any of the foregoing, 30-35 wt % of at least one first filler; 2.5-7.5 wt % of at least one binder; 2-3 wt % of at least one first disintegrant; and 0.25-1 wt % of at least one first lubricant. In some embodiments, the granules comprise the intragranular portion of a tablet disclosed herein.

In some embodiments, the tablet comprises particles of at least one crystalline form of Compound (I) having an average diameter of 10 to 150 microns. In some embodiments, the tablet comprises particles of at least one crystalline form of Compound (I) having an average diameter of 15, 56, 108, or 147 microns. In some embodiments, the tablet comprises crystalline Form A of Compound (I), crystalline Form B of Compound (I), and/or crystalline Form O of Compound (I)) or the weight equivalent of at least one crystalline form of a pharmaceutically acceptable salt thereof (e.g., crystalline Form T of a tosylate salt of Compound (I), crystalline Form Tr of a tartrate salt of Compound (I), and/or crystalline Form H of a hydrochloride salt of Compound (I)) or the weight equivalent of at least one crystalline form of a solvate of Compound (I) or a pharmaceutically acceptable salt thereof (e.g., crystalline Form C of Compound (I)).

All publications and patents mentioned herein are hereby incorporated by reference in their entirety as if each individual publication or patent was specifically and individually indicated to be incorporated by reference.

In the claims, articles such as "a," "an," and "the" may mean at least one than one unless indicated to the contrary or otherwise evident from the context. Claims or descriptions that include "or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which at least one limitation, element, clause, and descriptive term from at least one of the listed claims is introduced into another claim. For example, any claim that is dependent on another claim can be modified to include at least one limitation found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those of ordinary skill in the art will recognize or be able to ascertain using no more than routine experimentation, many equivalents to the specific embodiments of the disclosure described herein. Such equivalents are intended to be encompassed by the following claims.

EXAMPLES

The following examples are intended to be illustrative and are not meant in any way to limit the scope of the disclosure.

The synthetic schemes listed below are meant to provide general guidance in connection with preparing compounds of the present disclosure. One of ordinary skill in the art would understand that the preparations shown can be modified and/or optimized using general knowledge of organic chemistry.

| Abbreviations | |
|---|---|
| % w/w | Percentage weight by weight |
| Approximately | Approx. |
| Celsius | C. |
| Degrees | ° |
| Deionized | DI |
| Differential scanning calorimetry | DSC |
| Dynamic vapor sorption | DVS |
| Equivalents | eq. |
| Gram | g |
| High pressure liquid chromatography | HPLC |
| Karl Fisher Titration | KF |
| Kelvin | K |
| Liters | L |
| Milligrams | mg |
| Milliliters | mL |
| Molar | M |
| Mole | mol. |
| Normal | N |
| Nuclear magnetic resonance | NMR |
| Powder x-ray diffraction | XRPD |
| Relative humidity | RH |
| Thermogravimetric analysis | TGA |
| Volume | vol. |
| Weight | wt. |
| 1,1'-bis(di-tert-butylphosphino)ferrocene | DTBPF |
| 1,1'-ferrocenediyl-bis(diphenylphosphine) | DPPF |
| 2-methyltetrahydrofuran | 2-MeTHF |

| Abbreviations -continued | |
|---|---|
| 2-propanol | IPA |
| Acetonitrile | ACN |
| Ammonium chloride | $NH_4Cl$ |
| Charcoal per weight | CPW |
| Dichloromethane | DCM |
| Dimethyl sulfoxide | DMSO |
| Dipotassium phosphate | $K_2HPO_4$ |
| Ethanol | EtOH |
| Ethyl acetate | AcOEt |
| Hydrochloric acid | HCl |
| Isopropyl acetate | IPAc |
| Lithium hydroxide | LiOH |
| Methanol | MeOH |
| Methylmagnesium chloride | MeMgCl |
| Methyl tertiary-butyl ether | MTBE |
| N-methyl-2-pyrrolidone | NMP |
| N,N-diisopropylethylamine | DIPEA |
| Palladium(II) acetate | $Pd(OAc)_2$ |
| Phosphoryl chloride | $POCl_3$ |
| Potassium hydroxide | KOH |
| Sodium bicarbonate | $NaHCO_3$ |
| Sulfuric acid | $H_2SO_4$ |
| Tetrahydrofuran | THF |
| Tetra-n-butylammonium bromide | TBAB |
| Titanium isopropoxide | $Ti(OiPr)_4$ |
| Trifluoroacetic Acid | TFA |
| Trifluoroethanol | TFE |
| Tripotassium phosphate | $K_3PO_4$ |

General Methods

Optical Microscopy: Optical microscopy was performed using a Zeiss AxioScope A1 equipped with 2.5×, 10×, and 40× objectives and polarizer. Images were captured through a built-in Axiocam 105 digital camera and processed using ZEN 2 (blue edition) software provided by Zeiss.

DVS: Dynamic Vapor Sorption (DVS) was performed using a DVS Intrinsic 1.

The sample was loaded into a sample pan and suspended from a microbalance. A typical sample mass for DVS measurement was 25 mg. Nitrogen gas bubbled through distilled water provided the desired relative humidity. A typical measurement comprised the following steps:

1. Equilibrate at 50% RH
2. 50% to 2%. (50%, 40%, 30%, 20%, 10%, and 2%)
   a. Hold minimum of 5 minutes and maximum of 60 minutes at each humidity.
   The pass criteria was less than 0.002% change;
3. 2% to 95% (2%, 10%, 20%, 30%, 40%, 50%, 60%, 70%, 80%, 90%, 95%)
   a. Hold minimum of 5 minutes and maximum of 60 minutes at each humidity.
   The pass criteria was less than 0.002% change;
4. 95% to 2% (95%, 80%, 70%, 60%, 50%, 40%, 30%, 20%, 10%, 2%)
   a. Hold minimum of 5 minutes and maximum of 60 minutes at each humidity.
   The pass criteria was less than 0.002% change;
5. 2% to 50% (2%, 10%, 20%, 30%, 40%, 50%)
   a. Hold minimum of 5 minutes and maximum of 60 minutes at each humidity.
   The pass criteria was less than 0.002% change.

Thermal Analysis: Thermogravimetric analysis (TGA) and differential scanning calorimetry (DSC) were done using a Mettler Toledo TGA/DSC3+. Samples were weighed in aluminum hermetic pans with pin-holes. The parameters used are shown below.

| Parameters-TGA/DSC3+ | |
|---|---|
| Method | Ramp |
| Sampling Size | 5-10 mg |
| Heating rate | 10.0° C./min |
| Temperature range | 30° C. to 300° C. |

Karl Fisher Titration: Karl Fischer titration for water determination was done using a 785 DMP Titrino and 703 Ti Stand equipped with 6.0338.100 double platinum wire electrodes. Samples were dissolved in HPLC grade or anhydrous methanol and titrated with Hydranal-Composite 5. A typical sample mass for the measurement was 0.03 g to 0.10 g. Hydranal 1 wt. % water standard was used for calibration.

Chloride Content by Ion-Selective Electrode (ISE): Chloride content of samples was determined by a titration method with ion-selective electrode. Titration was carried out using an Accumet AB250 pH/ISE benchtop meter (Fisher Scientific) coupled with an Accumet combination chloride electrode. Microsoft Excel software was used to determine the inflection point of the titration curve.

NMR: Proton and carbon NMR analyses were performed on a Bruker Avance 500 MHz spectrometer. Alternatively, proton NMR was performed on a Bruker Avance 300 MHz spectrometer. Solids were dissolved in 0.75 mL deuterated solvent in a 4 mL vial and transferred to an NMR tube (Wilmad 5 mm thin wall 8" 200 MHz, 506-PP-8). Typical parameters for NMR on a Bruker Avance 300 MHz or 500 MHz spectrometer are listed below.

| Parameters-Bruker Avance 500 MHz | |
|---|---|
| Instrument | Bruker Avance 500 MHz spectrometer |
| Temperature | 300K |
| Probe | 5 mm PABBO BB-1H/D Z-GRD Z113652/0159 |
| Number of scans | 1028 |
| Relaxation delay | 1.000 s |
| Pulse width | 14.00 μs |
| Acquisition time | 0.8107 s |
| Spectrometer frequency | 500.13 Hz |
| Nucleus | $^{13}C$ |

| Parameters-Bruker Avance 300 MHz | |
|---|---|
| Instrument | Bruker Avance 300 MHz spectrometer |
| Temperature | 300K |
| Probe | 5 mm PABBO BB-1H/D Z-GRD Z104275/0170 |
| Number of scans | 16 |
| Relaxation delay | 1.000 s |
| Pulse width | 14.2500 μs |
| Acquisition time | 2.9999 s |
| Spectrometer frequency | 300.15 Hz |
| Nucleus | 1H |

XRPD: X-ray powder diffraction was done using a Rigaku MiniFlex 600. Samples were prepared on Si zero-return wafers. Typical scans were obtained from 2θ of 4 to 30 degrees, with step size 0.05 degrees over five minutes with 40 kV and 15 mA. High resolution scans were obtained from 2θ of 4 to 40 degrees, with step size 0.05 degrees over thirty minutes with 40 kV and 15 mA. Typical parameters for XRPD are listed below.

| Parameters for Reflection Mode | |
|---|---|
| X-ray wavelength | Cu Kα1, 1.54 Å, |
| X-ray tube setting | 40 kV, 15 mA |
| Detector | SC-70 |
| Slit condition | Variable + Fixed Slit System with Kβ filter |
| Scan mode | Continuous |
| Scan range (°2θ) | 4-40 |
| Step size (°2θ) | 0.05 |
| Scan speed (°/min) | 1.25 |
| X-ray wavelength | Cu Kα1, 1.54 Å, |
| X-ray tube setting | 40 kV, 15 mA |
| Detector | SC-70 |
| Slit condition | Variable + Fixed Slit System with Kβ filter |
| Scan mode | Continuous |
| Scan range (°2θ) | 4-30 |
| Step size (°2θ) | 0.05 |
| Scan speed (°/min) | 5.00 |

Example 1: Preparation of Crystalline Form A of Compound (I)

Compound (I) (10.0 g) was dissolved in acetone (17.4 vol) and deionized water (3.2 vol, final ratio: acetone/water 85/15) to obtain a suspension. The suspension was heated to a temperature ranging from 40° C. to 50° C. and stirred at 40° C. to 50° C. for 15 minutes. A clear yellow solution was obtained. Subsequently, a polish filtration was carried out at 40° C. to 50° C. The filter was washed with acetone/water 85/15 (1 vol). The solution was then atmospherically distilled at 55° C. to 65° C. until a volume of approximately 146 mL was reached (14.6 vol, approximately 74 mL distillate). The solution was cooled to 45° C. to 55° C. over 15 minutes. Deionized water (10.5 vol) was then added to the solution at 45° C. to 55° C. over 30 minutes, resulting in a pale yellow suspension. The suspension was cooled to 20° C. to 25° C. over 2.5 hours, then stirred at 20° C. to 25° C. for 3 hours. The product was collected by filtration; the filter cake was displacement-washed twice with acetone/water 1/1 (2 vol each). The wet product was dried under vacuum at 68° C. to 72° C., yielding crystalline Form A of Compound (I) as a pale yellow solid (92% isolated yield).

Crystalline Form A of Compound (I) was analyzed by optical microscopy, XRPD, $^{13}C$ NMR, DVS, DSC, and TGA. XRPD data for crystalline Form A of Compound (I) are in Table 1. An X-ray powder diffractogram for crystalline Form A of Compound (I) is shown in FIG. 2. A DSC thermogram and TGA thermal curve for crystalline Form A of Compound (I) are shown in FIG. 3.

Example 2: Preparation of Crystalline Form B of Compound (I)

Compound (I) was heated and held at 195° C. for 10 minutes, then cooled to room temperature. The resulting solid was isolated by filtration.

Crystalline Form B of Compound (I) was analyzed by optical microscopy, XRPD, $^{13}C$ NMR, DSC, and TGA. XRPD data for crystalline Form B of Compound (I) are in Table 2. An X-ray powder diffractogram for crystalline Form B of Compound (I) is shown in FIG. 4. A DSC thermogram of crystalline Form B of Compound (I) is shown in FIG. 5.

Example 3: Preparation of Crystalline Form C of Compound (I)

Crystalline Form C was prepared by slurrying Compound (I) in methanol or 1:1 THF:water. The resulting solid was isolated by filtration.

Crystalline Form C of Compound (I) was analyzed by optical microscopy, XRPD, $^{13}$C NMR, DVS, DSC, and TGA. XRPD data for crystalline Form C of Compound (I) are in Table 3. An X-ray powder diffractogram for crystalline Form C of Compound (I) is shown in FIG. 6.

Example 4: Preparation of Crystalline Form O of Compound (I)

Crystalline Form O was prepared by stagnant cooling of Compound (I) in THF from room temperature to −20° C. The resulting solid was isolated by filtration.

Crystalline Form O of Compound (I) was analyzed by optical microscopy, XRPD, $^{13}$C NMR, DSC, and TGA. XRPD data for crystalline Form O of Compound (I) are in Table 4. An X-ray powder diffractogram for crystalline Form O of Compound (I) is shown in FIG. 7.

Example 5: Preparation of Crystalline Form T of Tosylate Salt of Compound (I)

Compound (I) (169.7 mg) was weighed into a 4 mL vial with a 10 mm stir bar. Toluenesulfonic acid (75.8 mg, 1.1 equivalents) was weighed into the same vial. 20 vol. (3.39 mL) IPA:H$_2$O (95:5 vol) was added to the vial. The sample froze and was vortexed before stirring at room temperature for 5 minutes. The vial was transferred to a hot plate at 48° C.-50° C. and was left to stir at 600 rpm. The sample went into solution, then precipitated almost immediately as a thick slurry. The vial was transferred to a hot plate at 35° C. to 40° C. after 10 minutes and left to stir (340 rpm) for an hour before being left to stir at room temperature (340 rpm) for 1 hour. The sample was filtered, washed twice with 2 vol. (2×339 µL) IPA:H$_2$O (95:5 vol), and placed under active vacuum at 50° C. to dry. 170.6 mg of salt was collected.

Crystalline Form T of a tosylate salt of Compound (I) was analyzed by optical microscopy, XRPD, $^{13}$C NMR, DSC, TGA, and Karl Fisher (KF) titration for water content. Water content for the crystalline Form T of a tosylate salt of Compound (I) was 1.7 wt. %. XRPD data for crystalline Form T of a tosylate salt of Compound (I) are in Table 5. An X-ray powder diffractogram for crystalline Form T of Compound (I) is shown in FIG. 8.

Example 6: Preparation of Crystalline Form Tr of Tartrate Salt of Compound (I)

Compound (I) (145.2 mg) was weighed into a 4 mL vial with a 10 mm stir bar. Tartaric acid (50.3 mg, 1.1 equivalents) was weighed into the same vial. TFE (450 µL) was added. Because the solid did not dissolve, EtOH (250 µL) was also added. With stirring at room temperature, the slurry thinned slightly. Water (200 µL) was added to fully dissolve the solid, and the vial was left to stir (350 rpm) at room temperature overnight.

The solution remained clear the next day. The cap was removed, and the vial was placed on a hot plate at 35° C. to 40° C. to slowly evaporate with gentle stirring (300 rpm). After 3 hours, all solid had precipitated out of solution, and the vial was placed under active vacuum at 50° C. for 2 hours. 15 vol. (2.18 mL) acetone was added to the vial, and the sample was heated to 45° C. and stirred (400 rpm) for one hour. The temperature was decreased by 5 degrees every hour and left to stir overnight at room temperature. The sample was filtered, washed twice with 2 vol. (2×290 µL) acetone, and placed under active vacuum at 50° C. to dry. 152.1 mg of salt was collected.

Crystalline Form Tr of a tartrate salt of Compound (I) was analyzed by optical microscopy, XRPD, $^{13}$C NMR, DVS, DSC, TGA, and Karl Fisher (KF) titration for water content. Water content for the crystalline Form Tr of a tartrate salt of Compound (I) was 6.4 wt. %. XRPD data for crystalline Form Tr of a tartrate salt of Compound (I) are in Table 6. An X-ray powder diffractogram for crystalline Form Tr of a tartrate salt of Compound (I) is shown in FIG. 9.

Example 7: Preparation of Crystalline Form H of Hydrochloride Salt of Compound (I)

Compound (I) (154.0 mg) was weighed into a 4 mL vial with a 10 mm stir bar. 564 µL (1.1 equivalents) of a concentrated HCl solution in ethanol (5:95 vol.) was added. The sample gummed immediately, and the solid had a slight yellow tint. TFE (450 µL) was added, and the vial was placed on a hot plate at 35° C. to 40° C. to stir for half an hour (340 rpm). Gumming was broken apart with spatula at the 15-minute mark. The sample remained gummed after half an hour, so additional TFE (100 µL) was added and the sample was vortexed to produce a flowable white slurry. The vial was transferred to a stir plate at room temperature, and the sample was stirred for another 45 minutes. The cap was removed from the vial, and the solution was slowly evaporated overnight.

Solution remained the next morning, and the vial was placed back onto a hot plate at 35° C. to 40° C. for 2 hours, prior to being placed under active vacuum in an oven at 50° C. for 2 hours. Once removed, the gummed solid in the vial was broken apart with a spatula and 15 vol. (2.31 mL) acetone was added. The vial was placed on a hot plate at 48° C. and stirred (450 rpm) for one hour, then transferred to a hot plate room temperature (340 rpm) for another 2 hours. The sample was filtered, washed twice with 2 vol. (2×308 µL) acetone, and placed under active vacuum at 50° C. to dry. 138.4 mg of salt was collected.

Crystalline Form H of a hydrochloride salt of Compound (I) was analyzed by optical microscopy, XRPD, $^{13}$C NMR, DVS, DSC, TGA, and Karl Fisher (KF) titration for water content. Water content for the crystalline Form Tr of a tartrate salt of Compound (I) was 3.9 wt. %. XRPD data for crystalline Form H of a hydrochloride salt of Compound (I) are in Table 7. An X-ray powder diffractogram for crystalline Form Tr of a tartrate salt of Compound (I) is shown in FIG. 10.

Example 8: Solubility in Water and Simulated Fluids

Fasted simulated intestinal fluid (FaSSIF) (pH=6.57) was prepared by dissolving NaOH pellets (0.105 g), NaH$_2$PO$_4$·H$_2$O (0.9875 g), and NaCl (1.5475 g) in distilled water (225 mL) and adjusting the pH to 6.57 by adding 1 N NaOH solution and 1 N HCl. Water was then added to a volume of 250 mL to produce phosphate buffer. Biorelevant powder (0.56 g) was dissolved in the phosphate buffer (125 mL), then made up to 250 mL using phosphate buffer. The prepared solution was left standing for 2 hours and then used for solubility measurements.

Fasted simulated gastric fluid (FaSSGF) (pH=1.67) was prepared by dissolving NaCl (0.5 g) in distilled water (225 mL). The pH was adjusted to 1.67 using 1 N HCl, then the solution was made up to 250 mL using distilled water to produce NaCl/HCl solution. Biorelevant powder (0.015 g)

was dissolved in NaCl/HCl solution (125 mL), then made up to 250 mL using NaCl/HCl solution. The prepared solution was ready for use.

Crystalline Forms A and C of Compound (I)

Solubility of crystalline Form A and a mixture of crystalline Form A and crystalline Form C was measured in fasted simulated intestinal fluid (FaSSIF), fasted simulated gastric fluid (FaSSGF), and water at 37° C. Thin slurries were stirred overnight and then supernatant was collected for HPLC analysis. The solubility in FaSSIF for crystalline Form A and the mixture of crystalline Form A and crystalline Form C was 0.03 mg/mL. Solubility was higher in FaSSGF for crystalline Form A and the mixture of crystalline Form A and crystalline Form C at 2.11 mg/mL and 2.72 mg/mL, respectively. Solubility in water at approximately pH 7 was below the detection limit (BDL) for both crystalline Form A and the mixture of crystalline Form A and crystalline Form C. Solubility data is summarized in Table 8 below.

Crystalline Forms of Salts of Compound (I)

Solubility of crystalline Form H of a hydrochloride salt of Compound (I), crystalline Form Tr of a tartrate salt of Compound (I), and crystalline Form T of a tosylate salt of Compound (I) was measured in fasted state simulated intestinal fluid (FaSSIF), fasted state simulated gastric fluid (FaSSGF), and water at 37° C. About 1.5 mL solution was stirred at 37° C. The salt was then added incrementally until a thin slurry was formed, followed by stirring overnight. The solids were allowed to settle, and the pH of the supernatant was taken. Supernatant was recovered for injection to HPLC and solids were recovered for XRPD.

Solubility was determined based on interpolation from a calibration curve prepared using freebase. A linear fit gave an $R^2$ of 0.999.

Solubility of crystalline Form H and crystalline Form Tr were higher in both FaSSIF and water compared to freebase. Solubility in FaSSGF was also higher, but further dilution of samples was necessary. Solubility of crystalline Form Tr was greater than crystalline Form H in FaSSIF (0.27 vs 0.10 mg/mL). Crystalline Form Tr gummed in FaSSIF.

Solids were recovered from the slurries for analysis by XRPD. Crystalline Form H was stable upon slurrying in all solutions. Crystalline Form Tr was stable upon slurrying in water. Crystalline Form Tr converted into crystalline Form H upon slurrying in FaSSGF. Solubility data is summarized in Table 8 below.

TABLE 8

| Crystalline Form | Solubility (mg/mL) | | |
|---|---|---|---|
| | FaSSIF | FaSSGF | Water |
| A | 0.3 (pH 6.5-7) | 2.11 (pH~3) | BDL (pH~7) |
| A + C | 0.3 (pH 6.5-7) | 2.72 (pH 2.5-3) | BDL (pH~7) |
| Tr | 0.27 (pH~5.5) | 4.79 (pH 2.5-3) | 0.84 (pH 4.5-5) |
| H | 0.10 (pH~6) | 4.18 (pH 2-2.5) | 2.86 (pH 5-5.5) |
| T | 0.08 (pH~6) | 1.88 (pH 2-2.5) | 0.34 (pH~6) |

Example 9: Preparation 1 of Compound (I)

Step e: Preparation of tert-Butyl (S,Z)-4-(5-(((tert-butylsulfinyl)imino)(4-fluorophenyl)methyl)-pyrimidin-2-yl)piperazine-1-carboxylate tert-Butyl 4-(5-(4-fluorobenzoyl)pyrimidin-2-yl)piperazine-1-carboxylate (4.0 g, 1 eq.), (S)-(–)-2-methyl-2-propanesulfinamide (1.88 g, 1.5 eq.), Ti(OiPr)$_4$ (4.6 mL, 1.5 eq.), LiOH (0.06 g, 0.25 eq) and 2-MeTHF (32.0 mL, 8 vol.) were mixed and heated to 55° C. The reaction was held 3.5 hours and then cooled to 23° C. A brine solution (8.0 mL, 2 vol.) was added. The mixture was agitated for 2 to 3 hours and filtered through Celite to clarify. Additional brine wash (8.0 mL, 2 vol.) was added and the phases separated. The organic phase was distilled in vacuum and chased with 2-MeTHF (40 mL, 10 vol.) three times. 2-MeTHF (16 mL, 4 vol.) was then added and the mixture was agitated at 22° C. while heptane (48 mL, 12 vol.) was added. After 1 hour, the mixture was filtered to isolate the solid product that was dried under vacuum for 16 hours (75% yield of tert-Butyl (S,Z)-4-(5-(((tert-butylsulfinyl)imino)(4-fluorophenyl) methyl)-pyrimidin-2-yl)piperazine-1-carboxylate).

Step f: Preparation of tert-Butyl 4-(5-((S)-1-(((S)-tert-butylsulfinyl)amino)-1-(4-fluorophenyl)ethyl) pyrimidin-2-yl)piperazine-1-carboxylate 2-MeTHF (32 mL, 8 vol.) was added to tert-Butyl (S,Z)-4-(5-(((tert-butylsulfinyl) imino)-(4-fluorophenyl)methyl)-pyrimidin-2-yl)piperazine-1-carboxylate (4.0 g solid, 1 eq.). The mixture was cooled to −7° C. and MeMgCl (5.45 mL, 2.0 eq.) was added. The mixture was stirred for 2 hours at −7° C. Methanol (4.0 mL, 1 vol.) was added at not more than 0° C. The temperature was increased to 0-5° C. An NH$_4$Cl solution (24 mL, 6 vol.) was added and the biphasic mixture agitated at 20° C. The organic phase was separated from aqueous layer and then washed with water (12 mL, 2 vol.). MeOH (140 mL) was then added and the mixture was vacuum distilled while adding 2-MeTHF (250 mL). Vacuum distillation and 2-MeTHF chases were continued three times, ending with 38.0 g of 10.5% w/w solution of tert-Butyl 4-(5-((S)-1-(((S)-tert-butylsulfinyl)amino)-1-(4-fluorophenyl)ethyl)pyrimidin-2-yl)piperazine-1-carboxylate. The mixture was heated to 52° C. and heptane (46 mL, 11.5 vol.) was added followed by seeds (4 mg, 0.1% w/w). After agitating for 152 minutes at 52° C., the mixture was slowly cooled to 22° C. The solids were filtered and washed with heptane (2×8 mL) and then dried under vacuum for 16 hours. The crude solids (tert-Butyl 4-(5-((S)-1-(((S)-tert-butylsulfinyl)amino)-1-(4-fluorophenyl)ethyl)pyrimidin-2-yl)piperazine-1-carboxylate) (97.8 to 99.8% de) were purified according to the protocol directly below.

Step g: Purification of tert-Butyl-4-(5-((S)-1-(((S)-tert-butylsulfinyl)amino)-1-(4-fluorophenyl)-ethyl) pyrimidin-2-yl)piperazine-1-carboxylate Crude tert-Butyl 4-(5-((S)-1-(((S)-tert-butylsulfinyl) amino)-1-(4-fluorophenyl)-ethyl)pyrimidin-2-yl)piperazine-1-carboxylate (4.0 g) was suspended in heptane (78 mL, 19.5 vol.) and MeOH (2.0 mL, 0.5 vol.) and then heated to 57° C. After 2 hours, the mixture was cooled to 22° C. and agitated 1 h. Filtration with heptane washings (2×2 vol) were performed and the material was dried in vacuum overnight (35% yield of tert-Butyl-4-(5-((S)-1-(((S)-tert-butylsulfinyl) amino)-1-(4-fluorophenyl)-ethyl)pyrimidin-2-yl)piperazine-1-carboxylate over two steps, >99.8% de).

Step b: Preparation of 6-(1-methyl-1H-pyrazol-4-yl) pyrrolo[2,1-f][1,2,4]triazin-4-ol To a solution of 6-bromopyrrolo[1,2-f][1,2,4]triazin-4 (3H)-one (2.50 g, 1 eq.) in NMP (15 mL, 6 vol.) was added 1-methyl-4-(4,4,5,5-tetramethyl-1,3,2-dioxaborolan-2-yl)-1H-pyrazole (6.08 g, 2.5 eq.). TBAB (0.15 g, 4 mol. %), Pd(OAc)$_2$ (0.026 g, 1 mol. %) and DTBPF (0.055 g, 1 mol. %) were added. The mixture was degassed followed by K$_3$PO$_4$ (23.7 g, 6.0 eq) in water (7.5 mL, 3 vol.). Finally, the reaction mixture was heated to 100° C. for 12 hours. The reaction mixture was cooled to 20° C. and water (25 mL, 10 vol.) was added and the mixture agitated at 20° C. for 20 minutes. The mixture was clarified by filtration with washing of the filter with water (2.5 mL, 1 vol.). The filtrate was heated to 57° C. and 6 M HCl (12.5 mL, 5 vol.) was added. The resulting slurry was cooled to 3° C. over 3.5 hours and agitated for 2 hours at this temperature. The product was isolated by filtration and the solids washed with water (2×5 mL), followed by a 1:1 mix of THF and IPA (2×5 mL). The solids were dried, giving 80% yield of 6-(1-methyl-1H-pyrazol-4-yl)pyrrolo[2,1-f][1,2,4]triazin-4-ol.

Step c: Preparation of 4-chloro-6-(1-methyl-1H-pyrazol-4-yl)pyrrolo[2,1-f][1,2,4]triazine 6-(1-methyl-1H-pyrazol-4-yl)pyrrolo[2,1-f][1,2,4]triazin-4-ol (4.0 g, 1 eq.) was suspended in toluene (40 mL, 10 vol.) with DIPEA (3.9 mL, 1.2 eq.). The mixture was heated to 75° C. and POCl$_3$ (3.8 mL, 2.2 eq.) was added. The reaction was further heated to 105° C. for 16 hours. After reaction completion was reached, the reaction was cooled to 22° C. and added to a solution of K$_2$HPO$_4$ (32.5 g, 10 eq.) in water (25.9 mL, 6.5 vol.). The solid was filtered and washed with water (1 vol.) and toluene (1 vol.). The filtered solid was reslurried in DCM (28 mL, 7 vol.) at 22° C. The product solution was mixed with activated charcoal (5%). After charcoal filtration, the solution was concentrated to 2.4 vol. Heptane (7 vol.) was added and the mixture was concentrated to 2.4 volumes. More heptane was added and the mixture was concentrated to 7 volumes and stirred at 0-5° C. overnight. Filtration followed by heptane washes yielded a solid (78% yield of 4-chloro-6-(1-methyl-1H-pyrazol-4-yl)pyrrolo[2,1-f][1,2,4]triazine).

Step d: Preparation of (S)-1-(4-fluorophenyl)-1-(2-(piperazin-1-yl)pyrimidin-5-yl)ethan-1-amine hydrochloride tert-Butyl-4-(5-((S)-1-(((S)-tert-butylsulfinyl)amino)-1-(4-fluorophenyl)-ethyl)pyrimidin-2-yl)piperazine-1-carboxylate (4.0 g, 1 eq.) was mixed with methanol (25.2 mL, 7.5 vol.) in dioxane (10.0 mL, 6.0 eq.) and 4 M HCl. The reaction was heated to 40° C. for 1 hour. After reaction completion was reached, the mixture was cooled to 22° C. and charged with MTBE (34 mL, 10 vol.) over 30 minutes. The mixture was filtered and washed with MTBE (3×10 mL, 3×3 vol.) and dried under vacuum for 15 hours (97.0% yield of (S)-1-(4-fluorophenyl)-1-(2-(piperazin-1-yl)pyrimidin-5-yl)ethan-1-amine hydrochloride).

Step a: Preparation of (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-1-amine (Compound 4-chloro-6-(1-methyl-1H-pyrazol-4-yl)pyrrolo[2,1-f][1,2,4]triazine (3.87 kg, 0.95 eq.) was dissolved in DCM (138.1 kg, 20.0 vol.) followed by the addition of (S)-1-(4-fluorophenyl)-1-(2-(piperazin-1-yl)pyrimidin-5-yl)ethan-1-amine hydrochloride (7.4 kg, 1.0 eq.) and DIPEA (10.0 kg, 4.5 eq). The reaction was heated at reflux temperature for 12 hours. After reaching reaction conversion, the mixture was washed with brine (2×13% NaCl, 2×10 vol.). Concentration at atmospheric pressure until 3.7 volumes was followed by the addition of IPA (61.3 kg) and further concentration under vacuum to 14.5 volumes. The mixture was agitated at less than 25° C. and then IPA (20.4 kg) was again added. Further vacuum distillation to 14.5 volumes was followed by another IPA addition (20.4 kg). The resulting mixture was cooled to 2-8° C. and agitated for 1 hour. The solid product was isolated by filtration and washed with IPA (2×12.2 kg).

The crude solid was dissolved in a mixture of acetone (10.8 vol.) and water (1.9 vol.) at 50° C. Additional water (8.5 vol.) was added over 30 minutes, and the resulting suspension was cooled to 20° C. over 1 hour and agitated at that temperature for 2.5 hours. The resulting solid was isolated by filtration and washing with water/acetone mixture (1:1, 2×2 vol.). The solid was dried to give solid Compound (I) (77% yield of Compound (I)).

Example 10: Preparation 2 of Compound (I)

Step e: Preparation of tert-Butyl (S,Z)-4-(5-(((tert-butylsulfinyl)imino)(4-fluorophenyl)methyl)-pyrimidin-2-yl)piperazine-1-carboxylate tert-Butyl 4-(5-(4-fluorobenzoyl)pyrimidin-2-yl)piperazine-1-carboxylate (20.0 g, 1.0 eq.), (S)-(−)-2-methyl-2-propanesulfinamide (9.43 g, 1.5 eq) and LiOH (0.64 g, 0.5 eq.) were added to a reaction vessel with toluene (160 mL). To this mixture, titanium(IV)isopropoxide (18.42 g, 1.25 eq.) was added and the reaction agitated at 50-60° C. for 1 hour. The reaction was then distilled to remove 80 mL while charging additional toluene (80 mL) at 40-60° C. The reaction mixture was cooled to 20-30° C. and then added to a monosodium citrate solution (80 mL, 30%-w/w citric acid at pH 3-4). The mixture was agitated for 1.5 hours at 45-55° C. and then the phases separated. The organic phase was washed with potassium bicarbonate (40 mL, 25%-w/w aqueous) and the organic phase distilled to remove 40 mL. The product solution was diluted with tetrahydrofuran (30 mL) before being used in the next step directly as a solution (approx. 15% w/w of tert-Butyl (S,Z)-4-(5-(((tert-butylsulfinyl)imino)(4-fluorophenyl)methyl)-pyrimidin-2-yl)piperazine-1-carboxylate).

Step f: Preparation of tert-Butyl 4-(5-((S)-1-(((S)-tert-butylsulfinyl)amino)-1-(4-fluorophenyl)ethyl)pyrimidin-2-yl)piperazine-1-carboxylate by isolation Methyl magnesium chloride (27.8 g, 22%-w/w in THF, 2.0 eq.) was added to the tert-butyl (S,Z)-4-(5-(((tert-butylsulfinyl)imino)(4-fluorophenyl)methyl)-pyrimidin-2-yl)piperazine-1-carboxylate reaction solution in toluene/THF (120 g corresponding to 20 g input material) at 10° C. over 2 to 3 hours. The reaction mixture was allowed to agitate for 1.5 hours to reach reaction completion. The reaction mixture was quenched by the addition of methanol (40 mL) followed by water (10 mL). The mixture was distilled to remove 100-110 mL distillate and then washed with ammonium chloride (80 mL, 20% w/w in water). The organic phase was washed with water (80 mL), diluted with toluene (60 mL), and distilled to remove 60-80 mL distillate. The solution of tert-Butyl 4-(5-((S)-1-(((S)-tert-butylsulfinyl)amino)-1-(4-fluorophenyl)ethyl)pyrimidin-2-yl)piperazine-1-carboxylate at 50-60° C. was charged with n-heptane (80 mL) and then cooled to 42° C., at which time seeds were added (25-50 mg). The solution was held 30 minutes and then cooled to 0-10° C. for 30 minutes. The solids were isolated by filtration, washed with n-heptane and toluene mixture (1:1, 30 mL) followed by n-heptane (30 mL). The product was dried to yield 9 g (40-45%) of crude tert-Butyl 4-(5-((S)-1-(((S)-tert-butylsulfinyl)amino)-1-(4-fluorophenyl)ethyl)pyrimidin-2-yl)piperazine-1-carboxylate (96.4 to 97.2% de).

Recrystallization of tert-Butyl 4-(5-((S)-1-(((S)-tert-butylsulfinyl)amino)-1-(4-fluorophenyl)ethyl)pyrimidin-2-yl)piperazine-1-carboxylate tert-Butyl 4-(5-((S)-1-(((S)-tert-butylsulfinyl)amino)-1-(4-fluorophenyl)ethyl)pyrimidin-2-yl)piperazine-1-carboxylate (10.0 g) was dissolved in isopropanol (100 mL) and heated to 40-60° C., then passed through a clarifying filter with washing/rinsing with isopropanol (20 mL). The resulting solution was vacuum distilled at 40-60° C. to remove 60-70 mL distillate. The mixture was diluted with water (45 mL) at 50-60° C. and then cooled to 40° C., at which time it was seeded with 25-50 mg. The mixture was further cooled to 20-25° C. and water (20 mL) was added. The solids were isolated by filtration, washed with isopropanol/water mixture (1:1, 20 mL) and then slurry washed with isopropanol/water (1:2, 30 mL). Drying yielded 8.5 g (85%) of product of tert-Butyl-4-(5-((S)-1-(((S)-tert-butylsulfinyl)amino)-1-(4-fluorophenyl)ethyl)pyrimidin-2-yl)piperazine-1-carboxylate (>99.8% de).

Step b: Preparation of 6-(1-methyl-1H-pyrazol-4-yl)pyrrolo[2,1-f][1,2,4]triazin-4-ol 6-Bromopyrrolo[1,2-f][1,2,4]triazin-4(3H)-one (10.0 g) was charged to a reaction vessel followed by N-methyl-2-pyrrolidone (40 mL). To this mixture was added, 1-methyl-4-(4,4,5,5-tetramethyl-1,3,2-dioxaborolan-2-yl)-1H-pyrazole (24.4 g, 2.5 eq.), palladium(II)acetate (0.22 g), and 1,1'-bis(di-tert-butylphosphino)ferrocene (0.44 g). The mixture was agitated for 15 minutes. Potassium phosphate (59.66 g in 66 mL water) was added and the reaction mixture was heated to 115° C. for 2 h. The reaction mixture was cooled to 80° C. and added to a mixture of N-acetyl-L-cysteine (1.5 g) and $Na_2EDTA·2H_2O$ (1.5 g) in water (100 mL). The resulting mixture was agitated at 45° C. for 1.5 h and then cooled to 20° C. The organic layer was clarified and diluted with water (100 mL). Hydrochloric acid (10%-w/w) was added to adjust to pH 9.5. The organic solution was then heated to 75° C. and further adjusted with hydrochloric acid (10%-w/w) to pH 6.9. The mixture was cooled to 20° C. and held for 1 hour. The product was collected by filtration and washed twice with water/isopropanol (20 mL, 8:1 v/v) to give 8.2 g of dry product 6-(1-methyl-1H-pyrazol-4-yl)pyrrolo[2,1-f][1,2,4]triazin-4-ol.

Step c: Preparation of 4-chloro-6-(1-methyl-1H-pyrazol-4-yl)pyrrolo[2,1-f][1,2,4]triazine 6-(1-Methyl-1H-pyrazol-4-yl)pyrrolo[2,1-f][1,2,4]triazin-4-ol (15 g), DIPEA (10.36 g, 1.15 eq.), toluene (90 mL), and benzyltriethylammonium chloride (3.97 g, 0.25 eq.) were mixed. $POCl_3$ (21.37 g, 2.0 eq.) was added over 30 minutes. The mixture was then heated to 100° C. The mixture was cooled to 80-90° C. before it was quenched onto a mixture of $K_2HPO_4$ (2.4 g, 0.20 eq.) in 50 mL of deionized water and THF (50 mL) over 25 minutes. During the quench at 40-60° C., the pH was held between pH 7 and pH 9 by addition of KOH (~62 g, 50% aqueous, ~8 eq.). The obtained solution was then heated to 50-60° C. and stirring was continued for 30 minutes before the phases separated. The organic phase was washed twice at 50° C. with 45 mL of deionized water. After phase separation, the organic phase was vacuum distilled to 4 volumes at 60° C. The product precipitated as a yellow solid. Heptane (150 mL) was added and the product was then filtered and washed with heptane (50 mL). After drying under reduced pressure, the product 4-chloro-6-(1-methyl-1H-pyrazol-4-yl)pyrrolo[2,1-f][1,2,4]triazine (12.7 g) was obtained as a yellow powder.

Step a: Preparation of (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-1-amine (Compound (I))

tert-Butyl 4-(5-((S)-1-(((S)-tert-butylsulfinyl)amino)-1-(4-fluorophenyl)ethyl)pyrimidin-2-yl)piperazine-1-carboxylate (7) (9.0 g) was heated to 45-55° C. in acetonitrile (40 mL) with hydrochloric acid (33%, 8.14 g, 4.1 eq.) for 1 hour to afford tert-Butyl-4-(5-((S)-1-(((S)-tert-butylsulfinyl)amino)-1-(4-fluorophenyl)-ethyl)pyrimidin-2-yl)piperazine-1-carboxylate (2).

The mixture was cooled to 20-35° C. and then N,N-diisopropylethylamine (13.9 g, 6.0 eq.) and 4-chloro-6-(1-methyl-1H-pyrazol-4-yl)pyrrolo[2,1-f][1,2,4]triazine (4.0 g, 0.95 eq.) were added followed by methyl tert-butyl ether (20 mL) at 45-55° C. The reaction mixture was agitated at 50-65° C. for 30 minutes. Water (95 mL) was added slowly over 1 hour at 55-65° C. and IPC for pH 7.3-7.7 (adjusted with DIPEA or HCl if needed). The reaction mixture was cooled to 20-30° C. over 1 hour and held 1 hour at temperature. The product was filtered and washed (15 mL ACN displacement followed by 20 mL ACN slurry) to give 6.7 g crude (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-1-amine (Compound (I)).

(S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-1-amine (Compound (I)) (10.0 g) was dissolved in acetone (17.4 vol.) and deionized water (3.2 vol., final ratio: acetone/water 85/15). The suspension was heated to 43-48° C. and stirred at this temperature for 15 minutes. A clear yellow solution was obtained. Subsequently, a polish filtration was carried out at 43-48° C. and the filter washed with acetone/water 85/15 (1 vol.). The yellow solution was then atmospherically distilled at 57-62° C. until a volume of approximately 146 mL was reached (14.6 vol., approx. 74 mL distillate, final ratio: acetone/water 76/24). The solution was cooled to 48-53° C. over 15 minutes. After, deionized water (10.5 vol) was added at 48-53° C. over 30 minutes (final ratio: acetone/water 44/56). A pale yellow suspension was cooled to 20-25° C. over 2.5 hours and stirred at 20-25° C. for 3 hours. The product was collected by filtration and the filter cake was displacement-washed twice with acetone/water 1/1 (2 vol. each). The wet product was dried at 67-72° C. and 35 mbar. Compound (I) was isolated as a pale yellow solid (92% of theory) as crystalline Form A.

Example 11: Preparation 3 of Compound (I)

Step e: Preparation of tert-Butyl (S,Z)-4-(5-(((tert-butylsulfinyl)imino)(4-fluorophenyl)methyl)-pyrimidin-2-yl)piperazine-1-carboxylate tert-Butyl 4-(5-(4-fluorobenzoyl)pyrimidin-2-yl)piperazine-1-carboxylate (500 g, 1 eq.), (S)-(−)-2-methyl-2-propanesulfinamide (1.5 eq.), $Ti(OiPr)_4$ (2.0 eq.), LiOH (0.5 eq.), and toluene (4 L, 8 vol.) were mixed and heated to 60° C. under partial vacuum to remove IPA. The reaction was held for 5 hours and then cooled to 5-10° C. A citrate solution (30%, 4 vol.) was added. Decantation at 40° C. was followed by toluene extraction (1 vol.). The combined organic phases were washed with NaHCO$_3$ aqueous solution. The solution of tert-Butyl (S,Z)-4-(5-(((tert-butylsulfinyl)imino)(4-fluorophenyl)methyl)-pyrimidin-2-yl)piperazine-1-carboxylate was used directly in the next step.

Step f: Preparation of tert-Butyl 4-(5-((S)-1-(((S)-tert-butylsulfinyl)amino)-1-(4-fluorophenyl)ethyl) pyrimidin-2-yl)piperazine-1-carboxylate To the tert-Butyl (S,Z)-4-(5-(((tert-butylsulfinyl)imino)-(4-fluorophenyl)methyl)-pyrimidin-2-yl)piperazine-1-carboxylate reaction solution in toluene (50 g solid, 1 eq.) was added THF (4.2 vol.). At −15° C. to −10° C., MeMgCl (22.5% in THF, 1.5 eq.) was added. The mixture was stirred for 1 hour at −10° C. to −15° C. Additional MeMgCl (22.5% in THF, 0.5 eq.) was added and the mixture was stirred at −10° C. to −15° C. for 5 hours. Methanol (0.26 vol.) was added at −10±5° C. The temperature increased to 21° C. Toluene (4 vol.) was then added. HCl was added at 1.2° C. and the resulting suspension was stirred at room temperature overnight. The suspension was heated to 45° C. to give a biphasic solution. The organic phase was separated from aqueous layer and concentrated. AcOEt (2 vol.) was added and the solution was filtrated under a pad of silica gel (50 g). The silica pad was eluted with ethyl acetate (6×3.6 vol.), and fractions were mixed and concentrated until 1.65 volumes. The suspension of tert-Butyl 4-(5-((S)-1-(((S)-tert-butylsulfinyl)amino)-1-(4-fluorophenyl)ethyl)pyrimidin-2-yl)piperazine-1-carboxylate was heated (69° C.) to give a solution. Heptane (2.6 vol.) was added and the precipitate was stirred for 30 minutes at 30-40° C. and then cooled to 5° C. The yellow precipitate was filtrated and washed with heptane (2×1 vol.). The solid was dried under vacuum (45.4% yield of crude tert-Butyl 4-(5-((S)-1-(((S)-tert-butylsulfinyl)amino)-1-(4-fluorophenyl)ethyl)pyrimidin-2-yl)piperazine-1-carboxylate (94.4% de)).

Recrystallization of tert-Butyl-4-(5-((S)-1-(((S)-tert-butylsulfinyl)amino)-1-(4-fluorophenyl)-ethyl)pyrimidin-2-yl)piperazine-1-carboxylate Crude tert-Butyl 4-(5-((S)-1-(((S)-tert-butylsulfinyl)amino)-1-(4-fluorophenyl)ethyl)pyrimidin-2-yl)piperazine-1-carboxylate was dissolved in AcOEt (0.6 vol.). To this was added heptane (0.3 vol) at reflux temperature. More heptane (1.7 vol.) was added over 32 minutes, followed by cooling to 20-25° C. overnight. Filtration with heptane washings (2×0.5 vol.) was performed and the material was dried in vacuum overnight (88.2% yield of tert-Butyl-4-(5-((S)-1-(((S)-tert-butylsulfinyl)amino)-1-(4-fluorophenyl)-ethyl)pyrimidin-2-yl)piperazine-1-carboxylate, 100% de).

Step b: Preparation of 6-(1-methyl-1H-pyrazol-4-yl) pyrrolo[2,1-f][1,2,4]triazin-4-ol To a solution of 6-bromopyrrolo[1,2-f][1,2,4]triazin-4 (3H)-one (50 g, 1 eq.) in NMP (6 vol.) was added 1-methyl-4-(4,4,5,5-tetramethyl-1,3,2-dioxaborolan-2-yl)-1H-pyrazole (2.5 eq.). The mixture was degassed with nitrogen and then TBAB (0.04 eq.), Pd(OAc)$_2$ (0.01 eq.), and DPPF (0.01 eq.) were added. The mixture was degassed again. Water (3 vol.) was added at once, followed by K$_3$PO$_4$ (6 equivalents) portion-wise. Finally, the reaction mixture was again degassed and heated to 100±2° C. After reaching reaction completion, 10 volumes of water were added and the suspension agitated at 50° C. for 1 hours. At 21° C., the addition of HCl (6 N) adjusted the mixture to pH 6.51. Cooling to −10° C. for 1 hour was followed by filtration with washing of the filter cake with 3.6 volumes of water. The solids were triturated with 5 volumes of IPAc, followed by filtration. Additional trituration in 5 volumes of IPAc was again followed by filtration. A third trituration in 5 volumes of IPAc, was followed by filtration and a final trituration in 5 volumes of water. The solid product was washed with 5 volumes of water and dried under vacuum at 50° C. (70% yield of 6-(1-methyl-1H-pyrazol-4-yl)pyrrolo[2,1-f][1,2,4] triazin-4-ol.

Step c: Preparation of 4-chloro-6-(1-methyl-1H-pyrazol-4-yl)pyrrolo[2,1-f][1,2,4]triazine 6-(1-Methyl-1H-pyrazol-4-yl)pyrrolo[2,1-f][1,2,4]triazin-4-ol (180 g) was suspended in toluene (9.3 vol.) with DIPEA (1.2 eq.). To this mixture was added POCl$_3$ (2.0 eq) at 70-80° C. over 12 minutes. The suspension was heated to 70-80° C. After reaction completion was reached, the reaction was added to a solution of K$_2$HPO$_4$ (13 eq.) in water (11 vol.) at a temperature less than 30° C. The solid was filtered and washed with toluene and water. The filtrate was decanted; the aqueous layer was extracted with DCM. Filtered solid was reslurried in DCM (10 vol.). Organic layers were mixed and stirred with activated charcoal (5%). After charcoal filtration, the solution was concentrated to 2.4 volumes. Heptane (7 vol.) was added and the mixture was concentrated to 2.4 volumes. Additional heptane was added, and the mixture was concentrated to 7 volumes and stirred at 0-5° C. overnight. Filtration followed by heptane washes gave crude solid. A reslurry of wet solid in water (7 vol.) for 3.5 hours was followed by filtration and drying in vacuum (82.8% of 4-chloro-6-(1-methyl-1H-pyrazol-4-yl)pyrrolo[2, 1-f][1,2,4]triazine).

Preparation of (S)-1-(4-fluorophenyl)-1-(2-(piperazin-1-yl)pyrimidin-5-yl)ethan-1-amine hydrochloride tert-Butyl-4-(5-((S)-1-(((S)-tert-butylsulfinyl)amino)-1-(4-fluorophenyl)-ethyl)pyrimidin-2-yl)piperazine-1-carboxylate (50 g, 1 eq.) was mixed with ethanol (7.5 vol.) and concentrated hydrochloric acid (11.2 M, 5.6 eq.). The reaction was heated to reflux temperature. After reaction completion reached, the mixture was concentrated to 5 volumes under atmospheric pressure. Concentration was continued with addition of ethanol to maintain 5 volumes until water content was less than or equal to 3%. Concentration was finally stopped at 2 volumes followed by cooling to 0-5° C. over 30 minutes. Filtration was followed by drying under vacuum to give solid product (92.0% yield of (S)-1-(4-fluorophenyl)-1-(2-(piperazin-1-yl)pyrimidin-5-yl)ethan-1-amine hydrochloride).

Step a: Preparation of (S)-1-(4-fluorophenyl)-1-(2-(4-(6-(1-methyl-1H-pyrazol-4-yl)pyrrolo[2,1-f][1,2, 4]triazin-4-yl)piperazin-1-yl)pyrimidin-5-yl)ethan-1-amine (Compound 4-chloro-6-(1-methyl-1H-pyrazol-4-yl)pyrrolo[2,1-f][1, 2,4]triazine (5.0 g, 1 eq.) was dissolved in DCM (17.6 vol.) followed by the addition of (S)-1-(4-fluorophenyl)-1-(2-(piperazin-1-yl)pyrimidin-5-yl)ethan-1-amine hydrochloride (1.05 eq.) and butane-2,3-diol (5 wt %). DIPEA (4.5 eq.)

was added at a temperature less than or equal to 30° C. over 5 minutes. The reaction was heated at reflux temperature for 5.5 hours. After reaching reaction conversion, the mixture was washed with brine (2×22% NaCl in 2×8.9 vol.) and the organic phase was treated with charcoal (10% CPW) for 2 hours. Concentration at atmospheric pressure until 3.7 volumes was followed by the addition of IPA (26.8 vol.). Further concentration at atmospheric pressure until 18.3 volumes was followed by cooling to 20-25° C. The mixture was agitated for 1.5 hours at 20-25° C. and then filtered, washing with IPA (1.8 vol.). The wet solid was dissolved in a mixture of acetone (23.2 vol.) and water (4.1 vol.) at reflux temperature. Additional water (21.4 vol.) was added at 45-55° C. and the resulting suspension was cooled to 15-25° C. overnight. Cooling to 0-5° C. for 1 hour was followed by filtration and washing with water (2×3.6 vol.) and acetone (3.6 vol.) to give Compound (I) in 79.5% yield.

Example 12: Phase 1 Dose Escalation and Expansion Study of Compound (I) in Advanced GIST Patients: Eligibility criteria for the phase 1 dose escalation and expansion study included provision of written informed consent, age≥18 years, Eastern Cooperative Oncology Group performance status≤2, and adequate end-organ function. The dose escalation part of the trial was open to patients with refractory solid tumors or unresectable GIST; however, only GIST patients were enrolled. Patients with unresectable GIST who had one or more measurable target lesion per modified Response Evaluation Criteria in Solid Tumors version 1.1 (mRECIST 1.1) were eligible for the dose expansion, which included three cohorts: patients with PDGFRA D842V-mutant GIST regardless of prior therapy; patients who progressed following imatinib and one or more other kinase inhibitors; and patients who received only imatinib.

Study Design: The primary endpoints of the phase 1, open-label dose escalation/expansion study were safety and tolerability of Compound (I) administered orally once daily and overall response rate (ORR) for each expansion cohort. Part 1 followed a 3+3 dose-escalation design, starting at 30 mg and continuing until the maximum tolerated dose (MTD) or the recommended phase 2 dose (RP2D) below the MTD was determined. Intrapatient dose escalation was permitted, and additional accrual was allowed to dose levels previously determined tolerable. The part 1 MTD was used to initiate the part 2 expansion. Treatment with Compound (I) was continued until precluded by toxicity, noncompliance, withdrawal of consent, physician decision, progressive disease, death, or closure of the study.

Safety and Response Assessments: Adverse events were evaluated at each visit from the start of study drug administration up to 30 days after the final dose of Compound (I) and were graded according to the National Cancer Institute Common Terminology Criteria for Adverse Events (NCI CTCAE) version 4.03. All patients underwent tumor imaging for response assessment via computed tomography (CT) or magnetic resonance imaging (MRI) at screening, every two cycles through and including cycle 13, then every three months until progression or discontinuation. Target and non-target lesions were identified and assessed per mRECIST 1.1 for GIST by independent, blinded, central radiographic review (BioTelemetry, Inc., Rockville, MD, USA).

Pharmacokinetics: In part 1, serial blood samples were collected pre-dose, and at multiple time points through cycle 4. Parameters were calculated from the plasma concentration-time data using standard non-compartmental methods.

Statistical Methods: The MTD, defined as the highest dose level with ≤1 cycle 1 dose limiting toxicity in six patients, was determined from all part 1 patients who completed cycle 1 and received at least 75% of their prescribed doses or experienced a dose limiting toxicity (DLT) (dose-determining population). The efficacy population included patients who received at least one dose of Compound (I) enrolled in part 1 or part 2 with PDGFRα D842V-mutant GIST who had one or more target lesions and at least one post-baseline disease assessment by central radiology. For the primary endpoint of partial or complete response, a sample size of 31 patients allowed testing the null hypothesis of overall response rate≤10% versus the alternative hypothesis of objective response rate≥35% with 90% power, assuming a 2-sided type I error rate of 0.05. Kaplan-Meier methods were used to estimate duration of response, PFS and OS, including the median with 95% confidence intervals. Estimated duration of response, PFS, and OS rates at 3-, 6-, and 12-months were also calculated.

Results: 46 patients with PDGFRA-mutant (D842V, n=20, N659K, n=1; D842-H845, n=1, DI 842-843V, n=1) or KIT-mutant GIST (n=23) were enrolled in part 1 between October 2015 and January 2017, and the data cut-off was Nov. 16, 2018. Based on early efficacy observations, enrichment enrollment was restricted to patients with PDGFRA D842-mutant GIST. An additional 36 patients with PDGFRA D842V mutant GIST were enrolled in part 2, resulting in a total of 56 patients in the efficacy population (PDGFRA D842V-mutant GIST), and 82 patients in the safety population. In the D842V-mutant GIST population, the median age was 64 years, 41% were men, and 69% were white. Most had metastatic disease (96.4%) with at least 1 target lesion≥5 centimeters (58.6%) and were treated with ≥1 prior kinase inhibitor. Baseline characteristics of the safety and D842V populations were generally similar, except for mutational status and median number of prior kinase inhibitors (2 vs 1). Efficacy results for patients with KIT-mutant GIST will be reported separately.

Safety Profile: Patients enrolled in part 1 (n=46) received doses of 30 to 600 mg of Compound (I) once daily. No cycle-1 dose limiting toxicity was observed at doses of 30 to 400 mg per day. Two patients experienced cycle 1 dose-limiting toxicities (Patient 1: grade 2 hypertension, dermatitis acneiform, and memory impairment; Patient 2: grade 2 hyperbilirubinemia) at 600 mg. Both patients had temporary dose interruption and resumed dosing at 400 mg. 400 mg of Compound (I) was considered the maximum tolerated dose and chosen as the starting dose for Part 2. The Part 2 starting dose was subsequently reduced to 300 mg based on data showing a lower incidence of grade 3 cognitive AEs and a similar frequency of tumor response with Compound (I) exposure achieving predicted therapeutic levels. 300 mg of Compound (I) was therefore considered the recommended phase 2 dose and selected as the starting dose for the remainder of the study.

Most treatment-related adverse events were grade 1 or 2. At the 300 mg dose, the most common Grade 1/2 events were nausea (69%), diarrhea (41%), decreased appetite (38%), and fatigue (38%), were primarily Grade 1 (19, 23%), and resulted in treatment discontinuation in only 2 patients (2%). Intracranial hemorrhage occurred in 2 patients. Both events were Grade 3, non-fatal and improved while at the 400-mg dose, the most common were nausea (71%), vomiting (47%), fatigue (47%), and periorbital edema (47%). Grade 3/4 events, regardless of dose, occurred in 47 (57%) patients, the most common being anemia (30%). Adverse events of special interest included cognitive effects and intracranial bleeding. Cognitive effects occurred in 33 (40%) patients and included memory impairment (n=25, 30%), cognitive disorder (8, 10%), confusional state (7, 9%) and encephalopathy (2, 2%). Cognitive effects or resolved following treatment discontinuation.

A total of 69 (84%) patients required at least one dose reduction or treatment interruption, however median daily dose intensity remained high at 267 mg in the 84 patients who started at 300 mg.

Of the 82 patients enrolled, 44 (54%) discontinued treatment. The most common reasons for treatment discontinuation were disease progression (59%) and adverse events (34%), of which 12% were considered related to Compound (I). There were no treatment-related deaths. Of the PDGFRA D842V population, 19/56 (34%) discontinued treatment. Most common reasons for treatment discontinuation were disease progression (21%) and adverse events (63%), of which 14% were considered related to Compound (I). As of the data cut-off, 46% of all patients and 66% of the PDG-FRA D842V population remain on treatment.

Figure 11:
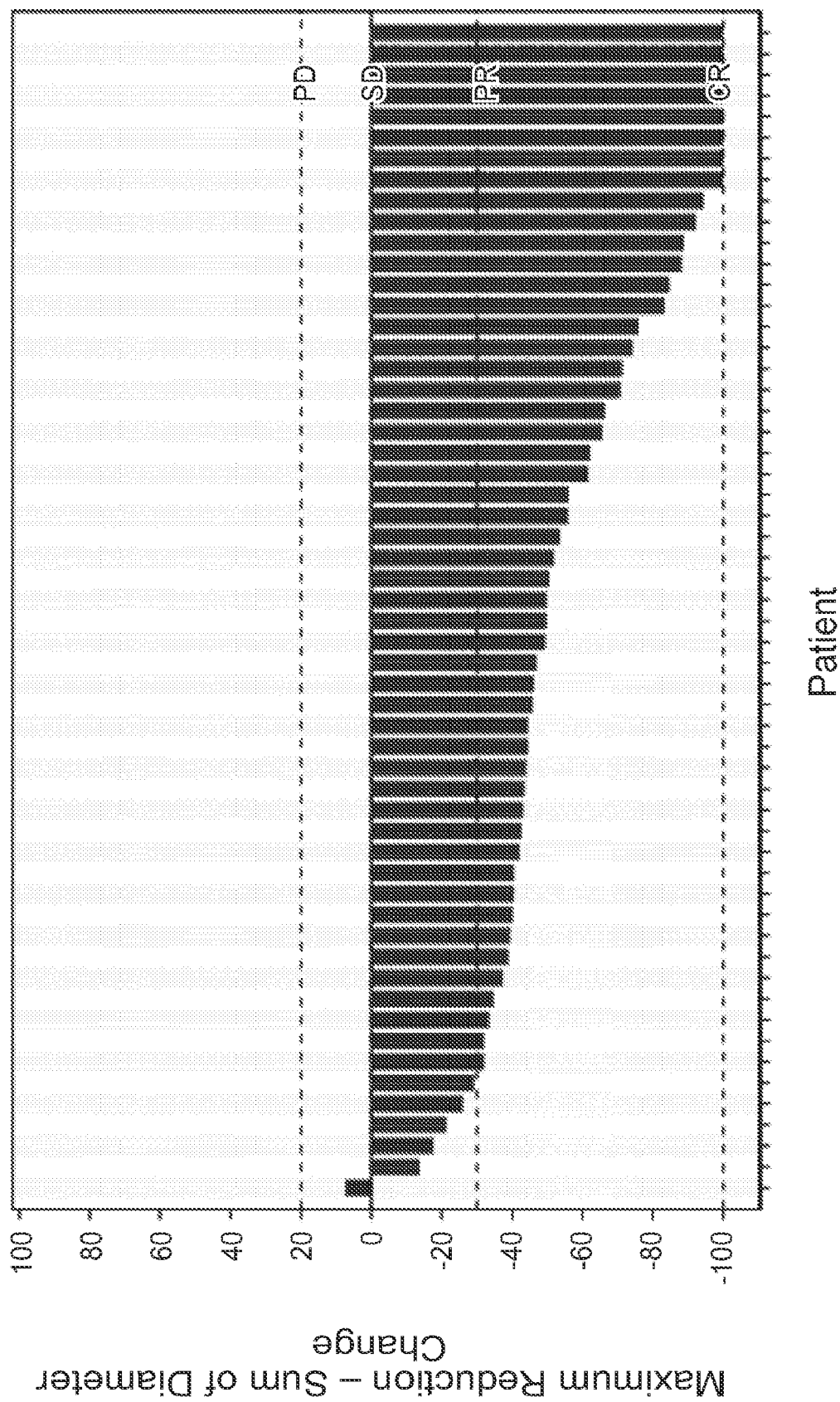
FIG. 11 shows the maximal percentage change in sum of tumor diameters from baseline in patients with PDGFRA D842V mutant GIST treated with Compound (I).

Efficacy: There were 56 response-evaluable patients with PDGFRA D842V-mutant GIST across all dose levels. Confirmed responses per central radiology mRECIST 1.1 assessments were seen in 88% (95% CI: 75.9. 94.8) of patients (complete response: 5/56 [8.9%], partial response: 44/56 [78.6%], and stable disease 7/56 (12.5%) (FIG. 11, Table 9). The clinical benefit rate (CBR), defined as the proportion of patients with a confirmed CR/PR or stable disease lasting for at least 16 weeks from the start of treatment, was 95%. The overall response rate was higher, at 93% (95% CI: 76.5, 99.1), in patients who started treatment at the recommended 300 mg dose (n=28). Median duration of response was not reached; the 12-month duration of response was 70%. Median PFS was not reached; 3-, 6-, and 12-month progression free survival rates were 100%, 94%, and 90%, respectively. OS was estimated to be 100%, 91% and 81% at 6, 12 and 24 months, respectively, with a median follow up of 15.9 months (95% CI: 54, 87%).

TABLE 9

|  | Response, n (%) | |
| --- | --- | --- |
|  | All Doses (n = 56) | 300 mg (n = 28) |
| CR | 5 (8.9) | 1 (3.6) |
| PR | 44 (78.6) | 25 (89.2) |
| ORR (CR + PR) | 49 (87.5) | 26 (92.9) |
|  | 95% CI 75.9, 94.8 | 95% CI 76.5, 99.1 |
| SD | 7 (12.5) | 2 (7.1) |
| CBR (CR + PR + SD) | 53 (94.6) | 27 (96.4) |
|  | 95% CI 85.1, 98.9 | 95% CI 81.7, 99.9 |
| PD | 0 | 0 |

In Part 1, 3 patients with other PDGFRA mutants were enrolled, 1 with an Exon 14 N659K mutation and 2 with other Exon 18 activation loop mutations (D842-H845, n=1, DI 842-843V, n=1). Both patients with activation loop mutations responded, however, the patient with the N659K mutation progressed.

Example 13: ISM and SSM Study of Compound (I)

This is a Phase 2, randomized, double-blind, placebo-controlled study comparing the efficacy and safety of Compound (I)+best supportive care (BSC) with placebo+BSC in patients with ISM and SSM whose symptoms are not adequately controlled by BSC. The study is conducted in three parts. In Part 1, the optimal dose Compound (I) (recommended phase 2 dose (RP2D)) was identified in patients with ISM. In Part 2, patients with ISM and SSM are randomly assigned to the RP2D of Compound (I) identified in Part 1+BSC, or to matching placebo+BSC. In Part 3, patients who have completed treatment in Part 1 or Part 2 of the study participate in a long-term extension, receiving Compound (I) at the RP2D+BSC.

In Part 1, immediately after informed consent was obtained, management of SM symptoms was optimized, and BSC medication doses and schedules for SM symptom management were stabilized, if needed, over four weeks. Within five days after informed consent is obtained, ISM-SAF (ISM Symptom Assessment Form) data collection begins. The number of anaphylactic episodes treated with epinephrine and all concomitant medications received for any indication were collected from the time of informed consent.

Once BSC was optimized (between Day −98 and Day −71) and doses were stable for ≥14 days, ISM-SAF data was collected for an additional 14 days to determine eligibility based on symptom severity i.e., to identify ISM and SSM patients having moderate-to-severe symptoms. Patients not meeting the symptom severity threshold were deemed screen failures and were not eligible for study participation. Patients having moderate-to-severe symptoms and meeting the threshold for symptom severity began other screening procedures, including the following: Bone marrow (BM) biopsy (an archival sample obtained within the preceding 24 weeks or a fresh sample) and skin biopsy of lesional and nonlesional skin (in patients with cutaneous mastocytosis (CM)) were performed for confirmation of SM diagnosis and quantification of mast cells (MCs); patients with CM (maculopapular) had skin photographs taken. Additional procedures include: magnetic resonance imaging/computed tomography scan of the brain; bone densitometry; serum tryptase, KIT D816 mutation testing; routine laboratory testing; ECG; and physical examination. All procedures are completed within a 6-week period before the final 14-day collection of baseline ISM-SAF symptoms is initiated.

Once screening procedures were completed, patients had ISM-SAF data collected for another 2 weeks (14 days) to establish baseline scores, after which patients meeting all eligibility requirements were randomly assigned to treatment and began dosing.

Part 1

In Part 1 of the study, approximately 40 patients were randomly assigned to 1 of 3 doses of Compound (I) or to placebo. Each dose-level cohort and placebo group in Part 1 was composed of 10 patients. The 3 dose levels of Compound (I) were tested in parallel: 25, 50, and 100 mg. Patients, study staff, and the Sponsor were blinded to treatment assignment.

Compound (I) was administered orally, once a day in continuous 28-day cycles. Patients were assessed weekly for the first 4 weeks, then every 4 weeks (until the RP2D was determined) for safety, laboratory monitoring, and quality of life (QoL) assessments. Intensive pharmacokinetic (PK) sampling was performed in all patients. The ISM-SAF was completed once a day. After completion of 12 weeks of treatment, BM and skin biopsy were repeated for MC quantification and skin photographs were taken in patients with baseline CM.

The RP2D was determined based on the efficacy, safety, and PK at each dose level. The primary evaluation of efficacy was the symptom improvement using the ISM-SAF.

The primary criterion for selection of the RP2D was the dose of Compound (I) that produces the maximum reduction in total symptom score (TSS), as assessed using the ISM-SAF at Week 12 compared with Baseline (Day −14 to Day −1). Other measures of efficacy (e.g., change in serum tryptase) are also be taken into consideration. Once Week 12 assessments are completed, patients continue on assigned therapy and dose until the RP2D is determined, at which time they will roll over to Part 3 of the study where they will receive the RP2D of Compound (I).

For each dose level of Compound (I) or placebo, mean change in TSS was calculated as the arithmetic average of the change in TSS in the Intent to Treat (ITT) population. Baseline TSS for each patient is defined as the 14-day average of TSS from C1D-14 to C1D-1. Cycle 4 Day 1 TSS for each patient is defined as the 14-day average of TSS from C3D15 to C3D28. For each patient, the change in TSS was calculated as (C4D1 TSS-Baseline TSS). If a patient was missing more than 7 days of TSS between C1D-14 and C1D-1, the Baseline TSS was considered as missing for the patient. If a patient was missing more than 7 days of TSS between C3D15 and C3D28, the C4D1 TSS was considered as missing for the patient.

Part 2

The screening procedure described above for Part 1 is used for Part 2. In Part 2 of the study, approximately 72 patients are enrolled. Patients are randomly assigned to receive Compound (I) at the RP2D+BSC or matching placebo+BSC. Patients assigned to placebo in Part 2 receive Compound (I), once they roll over into Part 3. Patients, study staff, and the Sponsor are blinded to treatment assignment.

Compound (I) and placebo dosing are administered orally, once a day in continuous 28-day cycles. Compound (I) is administered orally, once a day at 25 mg. Patients are assessed weekly for the first 4 weeks, then every 4 weeks through Week 12 for safety, laboratory monitoring, and QoL assessments. Sparse PK sampling is performed in all patients. The ISM-SAF is completed once a day. After completion of 12 weeks of treatment and the ISM-SAF through Week 12 Day 7, BM and skin biopsy are repeated for MC quantification by the Central Pathology Laboratory and skin photographs are taken in patients with baseline CM. Once all Week 12 assessments are completed, patients roll over into the Part 3 long-term extension. After all patients roll over into Part 3, the primary endpoint of mean change in ISM-SAF TSS from Baseline to Week 12 and other efficacy endpoints is analyzed.

The primary efficacy endpoint for Part 2 is the mean change in ISM-SAF TSS from baseline to cycle 4 day 1 (C4D1). The analysis of mean change in TSS will use the intent-to-treat population primarily and will be performed in the per-protocol population as a sensitivity analysis. Mean change in TSS will be calculated as the arithmetic average of the change in TSS in each treatment group. A 2-sample t-test will be used to compare Compound (I) and placebo.

Part 3

Patients who completed Part 1 roll over to Part 3 of the study, where all patients receive treatment with Compound (I)+BSC at 25 mg QD. Similarly, patients who complete all Part 2 Week 12 study assessments roll over to Part 3 of the study, where receive treatment with Compound (I)+BSC at 25 mg QD. All patients have study visits weekly for 4 weeks, then every 4 weeks for 5 months, and then every 3 months, for a total of 2 years from cycle 1 day 1 (C1D1). Patients still on study after 2 years have visits every 6 months (24 weeks) for a total study duration of 5 years, inclusive of Part 1 and Part 2. The ISM-SAF is completed once a day and QoL assessments performed through Week 52. In patients who had maculopapular CM (cutaneous mastocytosis) at Part 1 or Part 2 baseline, skin photographs are taken at Part 3 baseline (if not obtained within the prior 4 weeks in Part 1 or Part 2) and Weeks 12, 24, 36, and 52. Optional BM and skin biopsies are repeated for mast cell (MC) quantification by the Central Pathology Laboratory at Week 52. Week 12 study assessments for BM and skin biopsies from Part 1 and Part 2 may serve as baseline assessments for Part 3. Assessments performed at the final study visits in Part 1 and Part 2 may serve as baseline assessments for Part 3, if obtained within the preceding 4 weeks. Any procedures required at Part 3 baseline and not performed within 4 weeks of Part 3 Day 1 in Part 1 or Part 2 are performed on Day 1 of Part 3. Patients who choose not to continue on Compound (I) will have an end-of-treatment visit 14 days after last dose of study treatment. Patients may continue on Compound (I) until unacceptable toxicity, death, or patient withdrawal for a maximum of 5 years.

In Part 1, patients received treatment for 12 weeks, then patients continued on assigned therapy and were dosed until the RP2D of 25 mg QD was determined. In Part 2, patients receive treatment for up to 12 weeks. In Part 3, patients receive treatment for up to 5 years, inclusive of Part 1 and Part 2.

In Part 1, the minimum duration of patient participation was approximately 26 weeks. In Part 2, the minimum duration of patient participation is approximately 26 weeks. In Part 3, the minimum duration of patient participation is approximately 8 weeks.

In Part 1, the expected enrollment period was approximately 6 months and the expected duration of this part of the study was approximately 15 months. In Part 2, the expected enrollment period is approximately 9 months and the expected duration of this part of the study is approximately 18 months. The expected duration of Part 3 is approximately 5 years (inclusive of Part 1 and Part 2).

Results of Part 1:

Results from the Phase 2 PIONEER trial of Compound (I) in patients with indolent systemic mastocytosis (SM) showing significant clinical improvements versus placebo, including meaningful benefits across all symptoms assessed. In Part 1 of the PIONEER trial, patients treated with 25 mg once daily (QD) of Compound (I) demonstrated improvements in clinical outcomes from baseline to 16 weeks, with a 31 percent mean reduction in total symptom score (TSS) as measured by the Indolent SM Symptom Assessment Form (ISM-SAF) and deepening activity over time. In addition, the patients treated with 25 mg QD demonstrated robust reductions on objective measures of mast cell burden and improvements in patient-reported quality of life. Compound (I) showed a favorable safety profile supporting chronic dosing in ISM, and all adverse events (AEs) reported in the 25 mg QD dose cohort were Grade 1 or 2. Based on the full Part 1 data, 25 mg QD has been selected as the recommended Part 2 dose (RP2D).

Part 1 of the PIONEER trial was designed to determine the RP2D by evaluating three doses of Compound (I) (25 mg, 50 mg and 100 mg QD) versus placebo. Key eligibility criteria include adults with ISM confirmed by central pathology review of bone marrow biopsy (according to WHO criteria) and moderate-to-severe symptom burden despite best supportive care medicines. Overall, 39 patients were enrolled in Part 1 across four concurrent cohorts, consisting of 10 patients each in the Compound (I) dose cohorts and nine patients in the placebo cohort.

Patient-reported outcomes data were collected using the ISM-SAF, which was designed with input from disease experts, patients and regulatory authorities as a clinical benefit measure to support registration. The ISM-SAF assesses symptoms across the skin domain (spots, itching and flushing) and gastrointestinal domain (abdominal pain, diarrhea and nausea), as well as other key symptoms impacting patients with ISM (brain fog, headache, dizziness, bone pain and fatigue). All results are as of a data cutoff date of Dec. 27, 2019.

The full Part 1 data demonstrate the robust clinical activity and well-tolerated safety profile of Compound (I) at 25 mg QD. Based on these results, 25 mg QD has been selected as the optimal dose to evaluate further for the chronic treatment of ISM.

Baseline Patient Characteristics

Patients had high symptom burden at baseline, with a mean ISM-SAF TSS of 53. Eight patients (21 percent) had a mean ECOG performance status of 2, reflecting the inability to carry out any work activities. Patients received a median of four best supportive care medicines at baseline (range: 2-9). Median serum tryptase was 45 micrograms per liter (the upper limit of normal is 11.4 micrograms per liter). A high sensitivity polymerase chain reaction assay on peripheral blood detected the KIT D816V mutation in 37 patients (95 percent).

Clinical Activity Data

Compound (I) demonstrated clinically meaningful benefits across all measures of mast cell burden, patient-reported symptoms and quality of life. The consistency of results shown across multiple measures of disease support the broad potential of Compound (I) in ISM.

Figure 12:
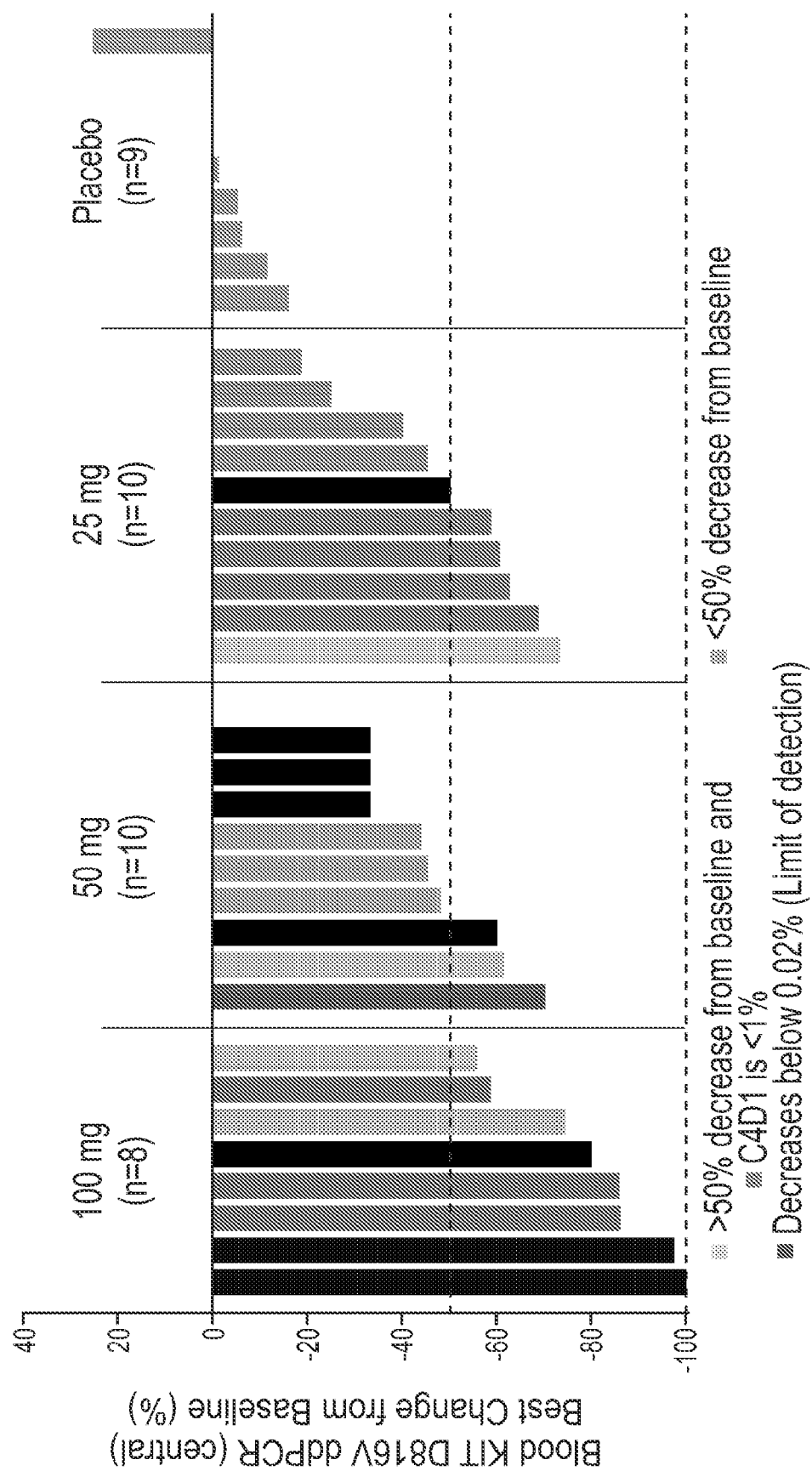
FIG. 12 shows bar graphs representing the effect of 25 mg once daily Compound (I), 50 mg once daily Compound (I), 100 mg once daily Compound (I) and placebo on the KIT D816V allele burden in ISM patients. All Compound (I) dose cohorts showed significant decreases in KIT D816V allele burden.
Figure 13:
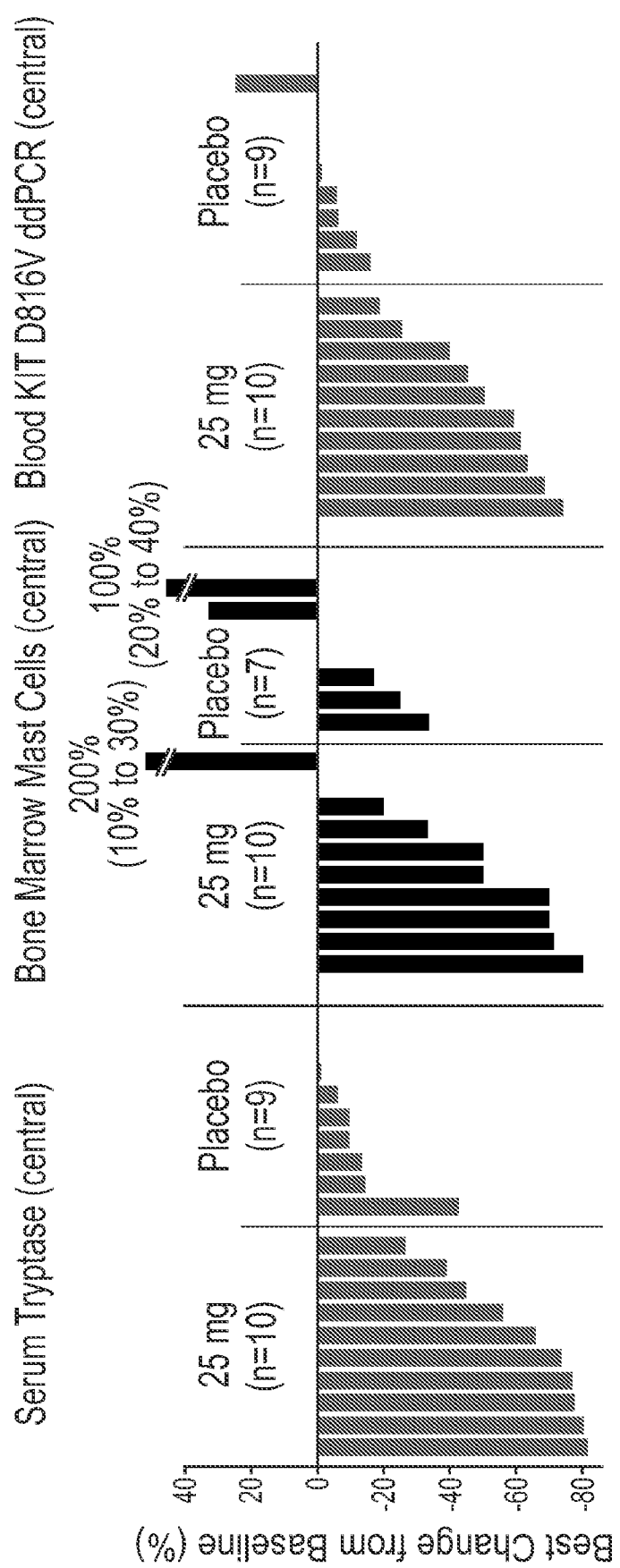
FIG. 13 shows significant reductions in serum tryptase, mast cell burden and KIT D816V allele burden in ISM patients treated with 25 mg once daily dose compared to patients treated with placebo.

Patients in the 25 mg QD dose cohort of Compound (I) showed robust declines in mast cell burden, based on assessments of serum tryptase, bone marrow mast cells and KIT D816V allele burden. See FIGS. 12-13.

Compound (I) showed clinically meaningful reductions in the ISM-SAF TSS, as well as the gastrointestinal domain, skin domain and each individual symptom tested. Improvements continuously deepened over the course of 16 weeks, with the potential for further reductions with additional patient follow-up. Patients in the 25 mg QD dose cohort of Compound (I) demonstrated a similar decline in mean symptom burden as the 50 mg QD dose cohort and the 100 mg QD dose cohort at 16 weeks. See FIGS. 14A-14C. As of the data cutoff date, 37 patients (95 percent) have remained on study with a median follow-up of 18 weeks (range: 1-36 weeks).

| Mean Percent Changes in ISM-SAF at 16 Weeks | | |
|---|---|---|
| | Compound (I), 25 mg QD (n = 9) | Placebo (n = 7) |
| TSS | −31% | −3% |
| Skin domain | −37% | +3% |
| Gastrointestinal domain | −25% | +7% |
| Neurological symptoms | −26% | −8% |

At 16 weeks, patients had a statistically significant reduction in ISM-SAF TSS (p=0.001), with a mean improvement of approximately 30 percent across all Compound (I) dose cohorts compared to approximately 3 percent in the placebo cohort (p=0.001).

Data from the Mastocytosis Quality of Life (MC-QoL) questionnaire, a commonly used patient-reported outcomes tool for mast cell disorders, demonstrate improvements in quality of life for patients receiving Compound (I) and validate the clinical benefits observed with the ISM-SAF. At 16 weeks, seven patients in the 25 mg QD cohort of Compound (I) and six patients in the placebo cohort completed the MC-QoL questionnaire. Patients in the 25 mg QD dose cohort showed a mean reduction of 34 percent in the total MC-QoL score and improvements in all four domains assessed (symptoms, social life functioning, emotions and skin). A 7 percent increase from baseline was observed in the placebo cohort.

Safety Data

As shown in the table below, Compound (I) showed a favorable safety profile supporting chronic dosing in ISM. No patients treated with Compound (I) in the 25 mg QD dose cohort had serious AEs, Grade 3 or higher AEs, or dose modifications. In the placebo cohort, two patients (22 percent) had at least one Grade 3 AE and two patients (22 percent) had dose modifications due to AEs. All doses of Compound (I) were well-tolerated, and no patients discontinued treatment due to AEs as of the data cutoff date.

| Safety Profiles Of All Three Doses Of Compound (I) and Placebo | | | | | | | | |
|---|---|---|---|---|---|---|---|---|
| AE in >15% of placebo or Compound (I) arms | | | Compound (I) | | | | | |
| Preferred term | Placebo n = 9 | | 25 mg n = 10 | | 50 mg n = 10 | | 100 mg n = 10 | |
| % of subjects with ≥1 AE | any grade 89 | grade 3 22 | any grade 100 | grade 3 0 | any grade 80 | grade 3 20 | any grade 90 | grade 3 40 |
| Nausea | 22 | 0 | 10 | 0 | 60 | 10 | 40 | 0 |
| Dizziness | 22 | 0 | 30 | 0 | 30 | 0 | 40 | 0 |
| Headache | 11 | 0 | 30 | 0 | 30 | 10 | 30 | 10 |
| Diarrhea | 11 | 0 | 0 | 0 | 40 | 10 | 30 | 10 |
| Fatigue | 11 | 0 | 40 | 0 | 10 | 0 | 10 | 0 |
| Face edema | 0 | 0 | 10 | 0 | 0 | 0 | 40 | 0 |
| Peripheral edema | 0 | 0 | 10 | 0 | 20 | 0 | 20 | 0 |
| Periorbital edema | 0 | 0 | 0 | 0 | 20 | 0 | 30 | 0 |
| Bone Pain | 22 | 0 | 0 | 0 | 0 | 0 | 0 | 0 |

Example 14: Process for Purifying Compound (I)

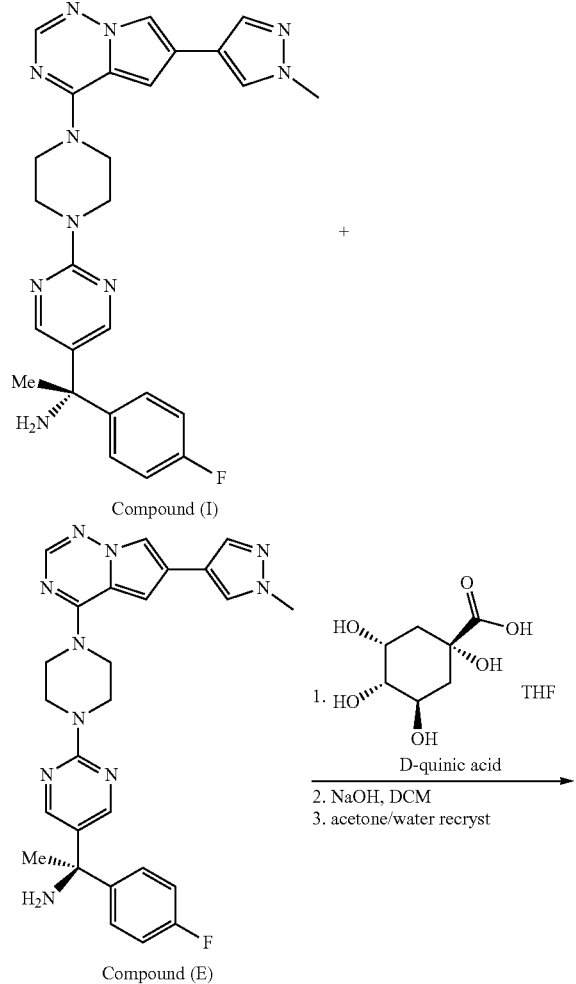

Compound (I) + D-quinic acid (1. THF, 2. NaOH, DCM, 3. acetone/water recryst) → Compound (I)

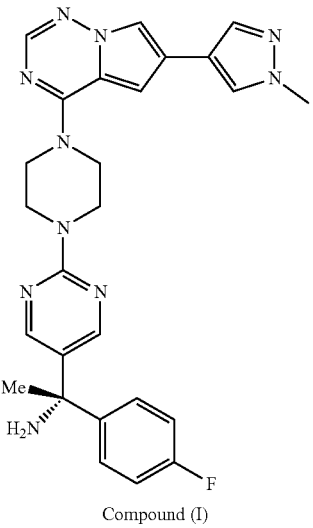

Purification of Compound (I) and its undesired enantiomer (Compound (E)) is difficult. For example, recrystallization in acetone and water of Compound (I) does not remove Compound (E). An investigation of several acids was necessary in order to find a process for removing the undesired enantiomer. Studies summarized in Table 10 were carried out on 500 mg scales each and D-quinic acid was determined to be the best acid for purifying Compound (I).

TABLE 10

| Corresponding acid | Solvent | % of undesired enantiomer | Yield |
| --- | --- | --- | --- |
| D(+)-camphoric acid; 1.0 eq | Acetone; 10.0 vol | 3.86% | — |
| L(−)-malic acid; 1.0 eq | Acetone; 30.0 vol | 4.23% | — |
| D-Quinic acid; 1.0 eq | Acetone; 40.0 vol | 0.86% | 87% |
| Di-p-anisoyl-D-tartaric acid; 1.0 eq | Acetone; 30.0 vol | 2.14% | — |
| S-tropic acid; 1.0 eq | Acetone; 10.0 vol | 5.95% | — |
| L(+)-ascorbic acid; 1.0 eq | Acetone; 10.0 vol | 5.73% | — |
| S-2-pyrrolidone-5-carboxylic acid; 1.0 eq | Acetone; 10.0 vol | 2.23% | — |
| (+)-Dibenzoyl-D-tartaric acid; 1.0 eq | Acetone; 10.0 vol | | — |
| (−)-Dibenzoyl-L-tararic acid; 1.0 eq | Acetone; 25.0 vol | 4.49% | — |
| (−)Di-p-toluoyl-L-tartaric acid; 1.0 eq | Acetone; 10.0 vol | 4.17% | — |
| D(−)-tartaric acid; 1.0 eq | Acetone; 10.0 vol | 5.04% | — |
| S(+)-mandelic acid; 1.0 eq | Acetone; 10.0 vol | 1.10% | 66.4% |
| D-quinic acid; 1.0 eq | EtOH; 20.0 vol | 3.86% | 95.3% |
| D-quinic acid; 1.0 eq | iPA; 10.0 vol | 4.55% | 95.3% |
| D-quinic acid; 1.0 eq | AcOEt; 10.0 vol | 5.41% | 85.9% |
| D-quinic acid; 1.0 eq | THF; 20.0 vol | 0.38% | 73.6% |
| S-mandelic acid; 1.0 eq | EtOH; 20.0 vol | 1.7% | 76.8% |
| S-mandelic acid; 1.0 eq* | iPA; 20.0 vol | — | — |

TABLE 10-continued

| Corresponding acid | Solvent | % of undesired enantiomer | Yield |
|---|---|---|---|
| S-mandelic acid; 1.0 eq | AcOEt; 20.0 vol | 1.44% | 84.52% |
| S-mandelic acid; 1.0 eq** | THF; 10.0 vol | 0.53% | 47% |

"—" means not determined
*bad filtration
**solution at 50° C. and precipitate at 20° C.

Specifically, to a suspension of Compound (I) (25.0 g, 1 equiv) and 5% Compound (E) in tetrahydrofuran (375 mL) was added D-quinic acid (1.5 equiv). The suspension was refluxed for 1h, water was added (5.5 equiv) and then cooled to 15-25° C. The solid was isolated by filtration and solids washed with tetrahydrofuran (2×50 mL). The THF and water recrystallization may be repeated to improve enantiomeric excess, if needed.

The isolated solid Compound (I) quinic acid salt was suspended in dichloromethane (250 mL) and water (125 mL) and NaOH (6.0 equiv) added. The organic layer was separated and washed with water (2×150 mL). With distillation, acetone was used to replace the dichloromethane finishing at a target volume of 5 mL/g of input Compound (I). Crude Compound (I) was isolated by filtration free of the undesired enantiomer and was recrystallized using acetone and water as described in Example 9 (step a). Compound (I) was isolated in approximately 65% yield with no detectable quinic acid present and ≤0.55% w/w enantiomer (Compound (E)).

The invention claimed is:

1. A method of treating systemic mastocytosis comprising administering to a patient in need thereof a therapeutically effective amount of crystalline Form A of Compound (I):

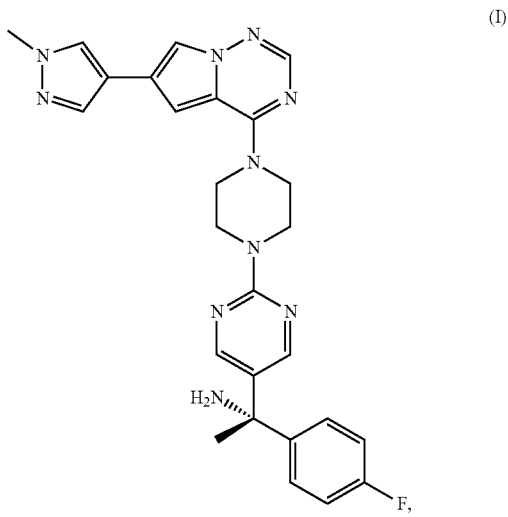 [SMILES: Cn1cc(-c2cc3c(N4CCN(c5ncc([C@@](C)(N)c6ccc(F)cc6)cn5)CC4)ncnn3c2)cn1]

(I)

characterized by an X-ray powder diffractogram which comprises at least three peaks at 2θ angles chosen from 11.5±0.2, 15.4±0.2, 16.7±0.2, 20.0±0.2, and 21.6±0.2.

2. The method of claim 1, wherein the crystalline Form A of Compound (I) is characterized by an X-ray powder diffractogram which comprises at least seven peaks at 2θ angles chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2.

3. The method of claim 1, wherein the crystalline Form A of Compound (I) is characterized by an X-ray powder diffractogram which comprises at least eight peaks at 2θ angles chosen from 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2.

4. The method of claim 1, wherein the crystalline Form A of Compound (I) is characterized by an X-ray powder diffractogram which comprises peaks at 2θ angles of 11.5±0.2, 15.4±0.2, 16.7±0.2, 18.1±0.2, 20.0±0.2, 21.6±0.2, 23.1±0.2, 23.9±0.2, 25.9±0.2, and 30.7±0.2.

5. The method of claim 1, wherein the crystalline Form A of Compound (I) is characterized by an X-ray powder diffractogram which comprises peaks at 2θ angles of 11.5±0.2, 15.4±0.2, 16.7±0.2, 20.0±0.2, and 21.6±0.2.

6. The method of claim 1, wherein the crystalline Form A of Compound (I) is characterized by a DSC thermogram having an endothermic event with a signal at a temperature ranging from 194° C. to 195° C. or an onset temperature of 193° C.

7. The method of claim 1, wherein the systemic mastocytosis is smoldering systemic mastocytosis (SSM).

8. The method of claim 1, wherein the systemic mastocytosis is advanced systemic mastocytosis (AdvSM).

9. The method of claim 8, wherein 200 mg of Crystalline Form A of Compound (I) is administered to the patient once daily.

10. The method of claim 1, wherein the systemic mastocytosis is selected from aggressive systemic mastocytosis (ASM), systemic mastocytosis associated with hematological non-mast cell lineage disease (SM-AHN), and mast cell leukemia (MCL).

11. The method of claim 1, wherein the systemic mastocytosis is indolent systemic mastocytosis (ISM).

12. The method of claim 1, wherein the patient has a mutation in Exon 17 in KIT.

13. The method of claim 12, wherein the patient has a D816 mutation in KIT in Exon 17.

14. The method of claim 13, wherein the D816 mutation is D816V.

* * * * *